(12) United States Patent
Pradeep et al.

(10) Patent No.: US 11,704,681 B2
(45) Date of Patent: Jul. 18, 2023

(54) NEUROLOGICAL PROFILES FOR MARKET MATCHING AND STIMULUS PRESENTATION

(71) Applicant: The Nielsen Company (US), LLC, New York, NY (US)

(72) Inventors: Anantha Pradeep, Berkeley, CA (US); Robert T. Knight, Berkeley, CA (US); Ramachandran Gurumoorthy, Berkeley, CA (US)

(73) Assignee: Nielsen Consumer LLC, Chicago, IL (US)

( * ) Notice: Subject to any disclaimer, the term of this patent is extended or adjusted under 35 U.S.C. 154(b) by 512 days.

(21) Appl. No.: 16/561,980

(22) Filed: Sep. 5, 2019

(65) Prior Publication Data

US 2020/0211033 A1    Jul. 2, 2020

Related U.S. Application Data

(63) Continuation of application No. 12/410,380, filed on Mar. 24, 2009, now abandoned.

(51) Int. Cl.
  *G06Q 30/02*         (2023.01)
  *G06Q 30/0202*       (2023.01)
  (Continued)

(52) U.S. Cl.
  CPC ............. *G06Q 30/02* (2013.01); *G06Q 10/08* (2013.01); *G06Q 30/0202* (2013.01);
  (Continued)

(58) Field of Classification Search
  CPC .... G06Q 30/02; G06Q 10/08; G06Q 30/0202; A61B 5/378; A61B 5/7278; A61B 5/7207
  (Continued)

(56) References Cited

U.S. PATENT DOCUMENTS 2,549,836 A    4/1951  McIntyre et al.
3,490,439 A    1/1970  Rolston
(Continued)

FOREIGN PATENT DOCUMENTS

EP    1087618    3/2001
EP    1609418    12/2005
(Continued)

OTHER PUBLICATIONS

Where psychophysiology meets the media; Lang et al.; 2009 (Year: 2009).*

(Continued)

*Primary Examiner* — Timothy Padot
*Assistant Examiner* — Francis Z. Santiago Merced
(74) *Attorney, Agent, or Firm* — Hanley, Flight & Zimmerman, LLC

(57) ABSTRACT

A neurological profile associated with introversion/extroversion levels, simultaneous visual element processing capability, and/or dynamism processing capability, etc., is determined to select market categories and stimulus material targeted to the particular neurological profile. The neurological profile is determined using information such as user input, user activity, social and environmental factors, genetic and developmental factors, and/or neuro-response data. The neurological profile can be matched with corresponding neurological profile templates to select market categories and stimulus material.

20 Claims, 7 Drawing Sheets

(51) Int. Cl.
   *G06Q 10/08* (2023.01)
   *A61B 5/378* (2021.01)
   *A61B 5/00* (2006.01)

(52) U.S. Cl.
   CPC ............ *A61B 5/378* (2021.01); *A61B 5/7207* (2013.01); *A61B 5/7278* (2013.01)

(58) Field of Classification Search
   USPC ...................................................... 705/7.29
   See application file for complete search history.

(56) References Cited

U.S. PATENT DOCUMENTS

| | | |
|---|---|---|
| 3,572,322 A | 3/1971 | Wade |
| 3,735,753 A | 5/1973 | Pisarski |
| 3,880,144 A | 4/1975 | Coursin et al. |
| 3,901,215 A | 8/1975 | John |
| 3,998,213 A | 12/1976 | Price |
| 4,075,657 A | 2/1978 | Weinblatt |
| 4,145,122 A | 3/1979 | Rinard et al. |
| 4,149,716 A | 4/1979 | Scudder |
| 4,201,224 A | 5/1980 | John |
| 4,279,258 A | 7/1981 | John |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,613,951 A | 9/1986 | Chu |
| 4,626,904 A | 12/1986 | Lurie |
| 4,632,122 A | 12/1986 | Johansson et al. |
| 4,683,892 A | 8/1987 | Johansson et al. |
| 4,686,999 A | 8/1987 | Snyder et al. |
| 4,695,879 A | 9/1987 | Weinblatt |
| 4,736,751 A | 4/1988 | Gevins et al. |
| 4,800,888 A | 1/1989 | Itil et al. |
| 4,802,484 A | 2/1989 | Friedman et al. |
| 4,846,190 A | 7/1989 | John |
| 4,859,050 A | 8/1989 | Borah et al. |
| 4,870,579 A | 9/1989 | Hey |
| 4,885,687 A | 12/1989 | Carey |
| 4,894,777 A | 1/1990 | Negishi et al. |
| 4,913,160 A | 4/1990 | John |
| 4,967,038 A | 10/1990 | Gevins et al. |
| 4,955,388 A | 11/1990 | Silberstein |
| 4,973,149 A | 11/1990 | Hutchinson |
| 4,987,903 A | 1/1991 | Keppel et al. |
| 5,003,986 A | 4/1991 | Finitzo et al. |
| 5,010,891 A | 4/1991 | Chamoun |
| 5,038,782 A | 8/1991 | Gevins et al. |
| 5,052,401 A | 10/1991 | Sherwin |
| 5,083,571 A | 1/1992 | Prichep |
| RE34,015 E | 8/1992 | Duffy |
| 5,137,027 A | 8/1992 | Rosenfeld |
| 5,213,338 A | 5/1993 | Brotz |
| 5,226,177 A | 7/1993 | Nickerson |
| 5,243,517 A | 9/1993 | Schmidt et al. |
| 5,273,037 A | 12/1993 | Itil et al. |
| 5,291,888 A | 3/1994 | Tucker |
| 5,293,867 A | 3/1994 | Oommen |
| 5,295,491 A | 3/1994 | Gevins |
| 5,331,544 A | 7/1994 | Lu et al. |
| 5,339,826 A | 8/1994 | Schmidt et al. |
| 5,345,281 A | 9/1994 | Taboada et al. |
| 5,357,957 A | 10/1994 | Itil et al. |
| 5,363,858 A | 11/1994 | Farwell |
| 5,392,788 A | 2/1995 | Hudspeth |
| 5,406,956 A | 4/1995 | Farwell |
| 5,410,609 A | 4/1995 | Kado et al. |
| 5,436,830 A | 7/1995 | Zaltman |
| 5,447,166 A | 9/1995 | Gevins |
| 5,450,855 A | 9/1995 | Rosenfeld |
| 5,474,082 A | 12/1995 | Junker |
| 5,479,934 A | 1/1996 | Imran |
| 5,513,649 A | 5/1996 | Gevins et al. |
| 5,518,007 A | 5/1996 | Becker |
| 5,537,618 A | 7/1996 | Boulton et al. |
| 5,550,928 A | 8/1996 | Lu et al. |
| 5,617,855 A | 4/1997 | Waletzky et al. |
| 5,655,534 A | 8/1997 | Ilmoniemi |
| 5,676,138 A | 10/1997 | Zawilinski |
| 5,676,148 A | 10/1997 | Koo et al. |
| 5,687,322 A | 11/1997 | Deaton et al. |
| 5,720,619 A | 2/1998 | Fisslinger |
| 5,724,987 A | 3/1998 | Gevins et al. |
| 5,726,701 A | 3/1998 | Needham |
| 5,729,205 A | 3/1998 | Kwon |
| 5,736,986 A | 4/1998 | Sever, Jr. |
| 5,740,035 A | 4/1998 | Cohen et al. |
| 5,762,611 A | 6/1998 | Lewis et al. |
| 5,771,897 A | 6/1998 | Zufrin |
| 5,774,591 A | 6/1998 | Black et al. |
| 5,787,187 A | 7/1998 | Bouchard et al. |
| 5,800,351 A | 9/1998 | Mann |
| 5,802,208 A | 9/1998 | Podilchuk et al. |
| 5,802,220 A | 9/1998 | Black et al. |
| 5,812,642 A | 9/1998 | Leroy |
| 5,817,029 A | 10/1998 | Gevins et al. |
| 5,842,199 A | 11/1998 | Miller et al. |
| 5,848,399 A | 12/1998 | Burke |
| 5,892,566 A | 4/1999 | Bullwinkel |
| 5,945,863 A | 8/1999 | Coy |
| 5,961,332 A | 10/1999 | Joao |
| 5,974,262 A | 10/1999 | Fuller et al. |
| 5,983,129 A | 11/1999 | Cowan et al. |
| 5,995,868 A | 11/1999 | Dorfmeister et al. |
| 6,001,065 A | 12/1999 | DeVito |
| 6,016,475 A | 1/2000 | Miller et al. |
| 6,021,346 A | 2/2000 | Ryu et al. |
| 6,032,129 A | 2/2000 | Greef et al. |
| 6,052,619 A | 4/2000 | John |
| 6,088,040 A | 7/2000 | Oda et al. |
| 6,099,319 A * | 8/2000 | Zaltman ............ A61B 5/16 434/362 |
| 6,120,440 A | 9/2000 | Goknar |
| 6,128,521 A | 10/2000 | Marro et al. |
| 6,154,669 A | 11/2000 | Hunter et al. |
| 6,155,927 A | 12/2000 | Levasseur et al. |
| 6,161,030 A | 12/2000 | Levendowski et al. |
| 6,170,018 B1 | 1/2001 | Voll et al. |
| 6,171,239 B1 | 1/2001 | Humphrey |
| 6,173,260 B1 | 1/2001 | Slaney |
| 6,175,753 B1 | 1/2001 | Menkes et al. |
| 6,182,113 B1 | 1/2001 | Narayanaswami |
| 6,190,314 B1 | 2/2001 | Ark et al. |
| 6,212,502 B1 | 4/2001 | Ball et al. |
| 6,228,038 B1 | 5/2001 | Claessens |
| 6,236,885 B1 | 5/2001 | Hunter et al. |
| 6,236,975 B1 | 5/2001 | Boe et al. |
| 6,254,536 B1 | 7/2001 | DeVito |
| 6,280,198 B1 | 8/2001 | Calhoun et al. |
| 6,286,005 B1 | 9/2001 | Cannon |
| 6,289,234 B1 | 9/2001 | Mueller |
| 6,292,688 B1 | 9/2001 | Patton |
| 6,299,308 B1 | 10/2001 | Voronka et al. |
| 6,301,492 B1 | 10/2001 | Zonenshayn |
| 6,301,493 B1 | 10/2001 | Marro et al. |
| 6,315,569 B1 | 11/2001 | Zaltman |
| 6,330,470 B1 | 12/2001 | Tucker et al. |
| 6,334,778 B1 | 1/2002 | Brown |
| 6,358,201 B1 | 3/2002 | Childre et al. |
| 6,370,513 B1 | 4/2002 | Kolawa et al. |
| 6,374,143 B1 | 4/2002 | Berrang et al. |
| 6,381,481 B1 | 4/2002 | Levendowski et al. |
| 6,398,643 B1 | 6/2002 | Knowles et al. |
| 6,422,999 B1 | 7/2002 | Hill |
| 6,434,419 B1 | 8/2002 | Gevins et al. |
| 6,435,878 B1 | 8/2002 | Reynolds et al. |
| 6,453,194 B1 | 9/2002 | Hill |
| 6,453,241 B1 | 9/2002 | Bassett, Jr. et al. |
| 6,487,444 B2 | 11/2002 | Mimura |
| 6,488,617 B1 | 12/2002 | Katz |
| 6,510,333 B1 | 1/2003 | Licata et al. |
| 6,510,340 B1 | 1/2003 | Jordan |

(56) References Cited

U.S. PATENT DOCUMENTS

| | | |
|---|---|---|
| 6,520,905 B1 | 2/2003 | Surve et al. |
| 6,545,685 B1 | 4/2003 | Dorbie |
| 6,575,902 B1 | 6/2003 | Burton |
| 6,577,329 B1 | 6/2003 | Flickner et al. |
| 6,585,521 B1 | 7/2003 | Obrador |
| 6,594,521 B2 | 7/2003 | Tucker |
| 6,598,006 B1 | 7/2003 | Honda et al. |
| 6,609,024 B1 | 8/2003 | Ryu et al. |
| 6,648,822 B2 | 11/2003 | Hamamoto et al. |
| 6,652,283 B1 | 11/2003 | Van Schaack et al. |
| 6,654,626 B2 | 11/2003 | Devlin et al. |
| 6,662,052 B1 | 12/2003 | Sarwal et al. |
| 6,665,560 B2 | 12/2003 | Becker et al. |
| 6,678,685 B2 | 1/2004 | McGill et al. |
| 6,688,890 B2 | 2/2004 | von Buegner |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopenathan et al. |
| 6,788,882 B1 | 9/2004 | Geer et al. |
| 6,792,304 B1 | 9/2004 | Silberstein |
| 6,842,877 B2 | 1/2005 | Robarts et al. |
| 6,850,252 B1 | 2/2005 | Hoffberg |
| 6,852,875 B2 | 2/2005 | Prakash |
| 6,888,457 B2 | 5/2005 | Wilkinson et al. |
| 6,904,408 B1 | 6/2005 | McCarthy et al. |
| 6,950,698 B2 | 9/2005 | Sarkela et al. |
| 6,958,710 B2 | 10/2005 | Zhang et al. |
| 6,973,342 B1 | 12/2005 | Swanson |
| 6,993,380 B1 | 1/2006 | Modarres |
| 7,020,508 B2 | 3/2006 | Stivoric et al. |
| 7,043,056 B2 | 5/2006 | Edwards et al. |
| 7,047,550 B1 | 5/2006 | Yasukawa et al. |
| 7,113,916 B1 | 9/2006 | Hill |
| 7,120,880 B1 | 10/2006 | Dryer et al. |
| 7,130,673 B2 | 10/2006 | Tolvanen-Laakso et al. |
| 7,150,715 B2 | 12/2006 | Collura et al. |
| 7,164,967 B2 | 1/2007 | Etienne-Cummings et al. |
| 7,177,675 B2 | 2/2007 | Suffin et al. |
| 7,222,071 B2 | 5/2007 | Neuhauser et al. |
| 7,246,081 B2 | 7/2007 | Hill |
| 7,249,708 B2 | 7/2007 | McConnell et al. |
| 7,272,982 B2 | 9/2007 | Neuhauser et al. |
| 7,286,871 B2 | 10/2007 | Cohen |
| 7,340,060 B2 | 3/2008 | Tomkins et al. |
| 7,359,894 B1 | 4/2008 | Liebman et al. |
| 7,391,835 B1 | 6/2008 | Gross et al. |
| 7,394,385 B2 | 7/2008 | Franco, Jr. et al. |
| 7,408,460 B2 | 8/2008 | Crystal et al. |
| 7,420,464 B2 | 9/2008 | Fitzgerald et al. |
| 7,443,292 B2 | 10/2008 | Jensen et al. |
| 7,460,827 B2 | 12/2008 | Schuster et al. |
| 7,463,143 B2 | 12/2008 | Forr et al. |
| 7,463,144 B2 | 12/2008 | Crystal et al. |
| 7,471,987 B2 | 12/2008 | Crystal et al. |
| 7,483,835 B2 | 1/2009 | Neuhauser et al. |
| 7,483,844 B2 | 1/2009 | Takakura et al. |
| 7,496,400 B2 | 2/2009 | Hoskonen et al. |
| 7,548,774 B2 | 6/2009 | Kurtz et al. |
| 7,551,952 B2 | 6/2009 | Gevins et al. |
| 7,592,908 B2 | 9/2009 | Zhang et al. |
| 7,614,066 B2 | 11/2009 | Urdang et al. |
| 7,623,823 B2 | 11/2009 | Zito et al. |
| 7,630,757 B2 | 12/2009 | Dorfmeister et al. |
| 7,636,456 B2 | 12/2009 | Collins et al. |
| 7,641,341 B2 | 1/2010 | Weinblatt |
| 7,650,793 B2 | 1/2010 | Jensen et al. |
| 7,658,327 B2 | 2/2010 | Tuchman et al. |
| 7,689,272 B2 | 3/2010 | Farwell |
| 7,697,979 B2 | 4/2010 | Martinerie et al. |
| 7,698,238 B2 | 4/2010 | Barletta et al. |
| 7,720,351 B2 | 5/2010 | Levitan |
| 7,729,755 B2 | 6/2010 | Laken |
| 7,765,564 B2 | 7/2010 | Deng |
| 7,774,052 B2 | 8/2010 | Burton et al. |
| 7,797,186 B2 | 9/2010 | Dybus |
| 7,809,420 B2 | 10/2010 | Hannula et al. |
| 7,840,248 B2 | 11/2010 | Fuchs et al. |
| 7,840,250 B2 | 11/2010 | Tucker |
| 7,844,484 B2 | 11/2010 | Arnett et al. |
| 7,865,394 B1 | 1/2011 | Calloway et al. |
| 7,892,764 B2 | 2/2011 | Xiong et al. |
| 7,895,075 B2 | 2/2011 | Gettys et al. |
| 7,895,625 B1 | 2/2011 | Bryan et al. |
| 7,908,133 B2 | 3/2011 | Neuhauser |
| 7,917,366 B1 | 3/2011 | Levanon et al. |
| 7,930,199 B1 | 4/2011 | Hill |
| 7,962,315 B2 | 6/2011 | Jensen et al. |
| 7,974,889 B2 | 7/2011 | Raimbeault |
| 7,988,557 B2 | 8/2011 | Soderland |
| 8,014,847 B2 | 9/2011 | Shastri et al. |
| 8,027,518 B2 | 9/2011 | Baker et al. |
| 8,055,722 B2 | 11/2011 | Hille |
| 8,060,795 B2 | 11/2011 | Bakekolo et al. |
| 8,065,203 B1 | 11/2011 | Chien et al. |
| 8,069,125 B2 | 11/2011 | Jung et al. |
| 8,073,707 B2 | 12/2011 | Teller et al. |
| 8,079,054 B1 | 12/2011 | Dhawan et al. |
| 8,082,215 B2 | 12/2011 | Jung et al. |
| 8,086,563 B2 | 12/2011 | Jung et al. |
| 8,098,152 B2 | 1/2012 | Zhang et al. |
| 8,099,315 B2 | 1/2012 | Amento et al. |
| 8,103,328 B2 | 1/2012 | Turner et al. |
| 8,126,220 B2 | 2/2012 | Greig |
| 8,135,606 B2 | 3/2012 | Dupree |
| 8,151,298 B2 | 4/2012 | Begeja et al. |
| 8,165,916 B2 | 4/2012 | Hoffberg et al. |
| 8,196,168 B1 | 6/2012 | Bryan et al. |
| 8,200,775 B2 | 6/2012 | Moore |
| 8,209,224 B2 | 6/2012 | Pradeep et al. |
| 8,219,438 B1 | 7/2012 | Moon et al. |
| 8,229,469 B2 | 7/2012 | Zhang et al. |
| 8,235,725 B1 | 8/2012 | Hill |
| 8,255,267 B2 | 8/2012 | Breiter |
| 8,270,814 B2 | 9/2012 | Pradeep et al. |
| 8,296,172 B2 | 10/2012 | Marci et al. |
| 8,300,526 B2 | 10/2012 | Saito et al. |
| 8,326,002 B2 | 12/2012 | Hill |
| 8,327,395 B2 | 12/2012 | Lee et al. |
| 8,332,883 B2 | 12/2012 | Lee et al. |
| 8,335,715 B2 | 12/2012 | Pradeep et al. |
| 8,381,244 B2 | 2/2013 | King et al. |
| 8,386,312 B2 | 2/2013 | Pradeep et al. |
| 8,386,313 B2 | 2/2013 | Pradeep et al. |
| 8,388,165 B2 | 3/2013 | Zhang |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,396,744 B2 | 3/2013 | Pradeep et al. |
| 8,473,345 B2 | 6/2013 | Pradeep et al. |
| 8,484,081 B2 | 7/2013 | Pradeep et al. |
| 8,484,801 B2 | 7/2013 | Pradeep et al. |
| 8,494,610 B2 | 7/2013 | Pradeep et al. |
| 8,494,905 B2 | 7/2013 | Pradeep et al. |
| 8,533,042 B2 | 9/2013 | Pradeep et al. |
| 8,548,852 B2 | 10/2013 | Pradeep et al. |
| 8,561,095 B2 | 10/2013 | Dimitrova et al. |
| 8,600,100 B2 | 12/2013 | Hill |
| 8,635,105 B2 | 1/2014 | Pradeep et al. |
| 8,655,428 B2 | 2/2014 | Pradeep et al. |
| 8,655,437 B2 | 2/2014 | Pradeep et al. |
| 8,709,054 B2 | 4/2014 | Lowry et al. |
| 8,762,202 B2 | 6/2014 | Pradeep et al. |
| 8,764,652 B2 | 7/2014 | Lee et al. |
| 8,788,372 B2 | 7/2014 | Kettner et al. |
| 8,793,715 B1 | 7/2014 | Weitzenfeld et al. |
| 9,021,515 B2 | 4/2015 | Lee et al. |
| 9,336,535 B2 | 5/2016 | Pradeep et al. |
| 9,560,984 B2 | 2/2017 | Pradeep et al. |
| 9,886,981 B2 | 2/2018 | Pradeep et al. |
| 9,894,399 B2 | 2/2018 | Lee et al. |
| 10,068,248 B2 | 9/2018 | Knight et al. |

(56) References Cited

U.S. PATENT DOCUMENTS

| | | |
|---|---|---|
| 10,127,572 B2 | 11/2018 | Pradeep et al. |
| 10,140,628 B2 | 11/2018 | Pradeep et al. |
| 10,269,036 B2 | 4/2019 | Knight et al. |
| 10,580,031 B2 | 3/2020 | Pradeep et al. |
| 10,679,241 B2 | 6/2020 | Pradeep et al. |
| 10,733,625 B2 | 8/2020 | Pradeep et al. |
| 10,937,051 B2 | 3/2021 | Pradeep et al. |
| 2001/0013009 A1 | 8/2001 | Greening et al. |
| 2001/0020236 A1 | 9/2001 | Cannon |
| 2001/0029468 A1 | 10/2001 | Yamaguchi et al. |
| 2001/0032140 A1 | 10/2001 | Hoffman |
| 2001/0056225 A1 | 12/2001 | DeVito |
| 2002/0053076 A1 | 5/2002 | Landesmann |
| 2002/0055857 A1 | 5/2002 | Mault |
| 2002/0056087 A1 | 5/2002 | Berezowski et al. |
| 2002/0056124 A1 | 5/2002 | Hay |
| 2002/0059577 A1 | 5/2002 | Lu et al. |
| 2002/0065826 A1 | 5/2002 | Bell et al. |
| 2002/0072952 A1 | 6/2002 | Hamzy et al. |
| 2002/0077534 A1 | 6/2002 | DuRousseau |
| 2002/0082902 A1 | 6/2002 | Ando et al. |
| 2002/0103429 A1 | 8/2002 | deCharms |
| 2002/0111796 A1 | 8/2002 | Nemoto |
| 2002/0116042 A1 | 8/2002 | Boling |
| 2002/0143627 A1 | 10/2002 | Barsade et al. |
| 2002/0155878 A1 | 10/2002 | Lert, Jr. et al. |
| 2002/0156842 A1 | 10/2002 | Signes et al. |
| 2002/0169665 A1 | 11/2002 | Hughes et al. |
| 2002/0178440 A1 | 11/2002 | Agnihotri et al. |
| 2002/0188216 A1 | 12/2002 | Kayyali et al. |
| 2002/0188217 A1 | 12/2002 | Farwell |
| 2002/0193670 A1 | 12/2002 | Garfield et al. |
| 2003/0013981 A1 | 1/2003 | Gevins et al. |
| 2003/0036955 A1 | 2/2003 | Tanaka et al. |
| 2003/0037333 A1 | 2/2003 | Ghashghai et al. |
| 2003/0044050 A1 | 3/2003 | Clark et al. |
| 2003/0059750 A1 | 3/2003 | Bindler et al. |
| 2003/0063222 A1 | 4/2003 | Creed et al. |
| 2003/0065524 A1 | 4/2003 | Giacchetti et al. |
| 2003/0073921 A1 | 4/2003 | Sohmer et al. |
| 2003/0081834 A1 | 5/2003 | Philomin et al. |
| 2003/0093792 A1 | 5/2003 | Labeeb et al. |
| 2003/0100998 A2 | 5/2003 | Brunner et al. |
| 2003/0104865 A1 | 6/2003 | Itkis et al. |
| 2003/0118975 A1 | 6/2003 | Stamm et al. |
| 2003/0131351 A1 | 7/2003 | Shapira |
| 2003/0149344 A1 | 8/2003 | Nizan |
| 2003/0165270 A1 | 9/2003 | Endrikhovski et al. |
| 2003/0177488 A1 | 9/2003 | Smith et al. |
| 2003/0204412 A1 | 10/2003 | Brier |
| 2003/0208754 A1 | 11/2003 | Sridhar et al. |
| 2003/0233278 A1 | 12/2003 | Marshall |
| 2004/0001616 A1 | 1/2004 | Gutta et al. |
| 2004/0005143 A1 | 1/2004 | Tsuru et al. |
| 2004/0013398 A1 | 1/2004 | Miura et al. |
| 2004/0015608 A1 | 1/2004 | Ellis et al. |
| 2004/0055448 A1 | 3/2004 | Byon |
| 2004/0068431 A1 | 4/2004 | Smith et al. |
| 2004/0073129 A1 | 4/2004 | Caldwell et al. |
| 2004/0088289 A1 | 5/2004 | Xu et al. |
| 2004/0092809 A1 | 5/2004 | DeCharms |
| 2004/0098298 A1 | 5/2004 | Yin |
| 2004/0101212 A1 | 5/2004 | Fedorovskaya et al. |
| 2004/0133081 A1 | 7/2004 | Teller et al. |
| 2004/0187167 A1 | 9/2004 | Maguire et al. |
| 2004/0193068 A1 | 9/2004 | Burton et al. |
| 2004/0210159 A1 | 10/2004 | Kibar |
| 2004/0219184 A1 | 11/2004 | Brown et al. |
| 2004/0220483 A1 | 11/2004 | Yeo et al. |
| 2004/0236623 A1 | 11/2004 | Gopalakrishnan |
| 2005/0010475 A1 | 1/2005 | Perkowski et al. |
| 2005/0041951 A1 | 2/2005 | Inoue et al. |
| 2005/0043646 A1 | 2/2005 | Viirre et al. |
| 2005/0060312 A1 | 3/2005 | Curtiss et al. |
| 2005/0062637 A1 | 3/2005 | El Zabadani et al. |
| 2005/0071462 A1 | 3/2005 | Bodin et al. |
| 2005/0071865 A1 | 3/2005 | Martins |
| 2005/0076359 A1 | 4/2005 | Pierson et al. |
| 2005/0079474 A1 | 4/2005 | Lowe |
| 2005/0097594 A1 | 5/2005 | O'Donnell et al. |
| 2005/0107716 A1 | 5/2005 | Eaton et al. |
| 2005/0108092 A1 | 5/2005 | Campbell et al. |
| 2005/0113649 A1 | 5/2005 | Bergantino |
| 2005/0132401 A1 | 6/2005 | Boccon-Gibod et al. |
| 2005/0143629 A1 | 6/2005 | Farwell |
| 2005/0149964 A1 | 7/2005 | Thomas et al. |
| 2005/0154290 A1 | 7/2005 | Langleben |
| 2005/0165766 A1 | 7/2005 | Szabo |
| 2005/0177058 A1 | 8/2005 | Sobell |
| 2005/0197590 A1 | 9/2005 | Osorio et al. |
| 2005/0203798 A1 | 9/2005 | Jensen et al. |
| 2005/0216071 A1 | 9/2005 | Devlin et al. |
| 2005/0216243 A1 | 9/2005 | Graham et al. |
| 2005/0223237 A1* | 10/2005 | Barletta ............ H04N 21/4402 348/E5.002 |
| 2005/0227233 A1 | 10/2005 | Buxton et al. |
| 2005/0240956 A1 | 10/2005 | Smith et al. |
| 2005/0246002 A1 | 11/2005 | Martinez |
| 2005/0256905 A1 | 11/2005 | Gruhl et al. |
| 2005/0261980 A1 | 11/2005 | Hadi |
| 2005/0267798 A1 | 12/2005 | Panara |
| 2005/0272017 A1 | 12/2005 | Neuhauser et al. |
| 2005/0273017 A1 | 12/2005 | Gordon |
| 2005/0273802 A1 | 12/2005 | Crystal et al. |
| 2005/0288954 A1 | 12/2005 | McCarthy et al. |
| 2005/0289582 A1 | 12/2005 | Tavares et al. |
| 2006/0003732 A1 | 1/2006 | Neuhauser et al. |
| 2006/0009702 A1 | 1/2006 | Iwaki et al. |
| 2006/0010470 A1 | 1/2006 | Kurosaki et al. |
| 2006/0035707 A1 | 2/2006 | Nguyen et al. |
| 2006/0041548 A1 | 2/2006 | Parsons et al. |
| 2006/0042483 A1 | 3/2006 | Work et al. |
| 2006/0053110 A1 | 3/2006 | McDonald et al. |
| 2006/0069663 A1 | 3/2006 | Adar et al. |
| 2006/0093998 A1 | 5/2006 | Vertegaal |
| 2006/0094934 A1 | 5/2006 | Shirai et al. |
| 2006/0111044 A1 | 5/2006 | Keller |
| 2006/0111644 A1 | 5/2006 | Guttag et al. |
| 2006/0129458 A1 | 6/2006 | Maggio |
| 2006/0149337 A1 | 7/2006 | John |
| 2006/0167376 A1 | 7/2006 | Viirre et al. |
| 2006/0168613 A1 | 7/2006 | Wood et al. |
| 2006/0168630 A1 | 7/2006 | Davies |
| 2006/0176289 A1 | 8/2006 | Horn |
| 2006/0189883 A1* | 8/2006 | Pomfrett ............ A61B 5/0536 600/547 |
| 2006/0189886 A1 | 8/2006 | Jones et al. |
| 2006/0190822 A1 | 8/2006 | Basson et al. |
| 2006/0218046 A1 | 9/2006 | Carfi et al. |
| 2006/0256133 A1 | 11/2006 | Rosenberg |
| 2006/0257834 A1 | 11/2006 | Lee et al. |
| 2006/0259360 A1 | 11/2006 | Flinn et al. |
| 2006/0259371 A1 | 11/2006 | Perrier et al. |
| 2006/0293921 A1 | 12/2006 | McCarthy et al. |
| 2007/0005752 A1 | 1/2007 | Chawla et al. |
| 2007/0016096 A1 | 1/2007 | McNabb |
| 2007/0038516 A1 | 2/2007 | Apple et al. |
| 2007/0048707 A1 | 3/2007 | Caamano et al. |
| 2007/0050256 A1 | 3/2007 | Walker et al. |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066874 A1 | 3/2007 | Cook |
| 2007/0066915 A1 | 3/2007 | Frei et al. |
| 2007/0066916 A1 | 3/2007 | Lemos |
| 2007/0067007 A1 | 3/2007 | Schulman et al. |
| 2007/0067305 A1 | 3/2007 | Ives |
| 2007/0078700 A1 | 4/2007 | Lenzmann et al. |
| 2007/0078706 A1 | 4/2007 | Datta et al. |
| 2007/0079331 A1 | 4/2007 | Datta et al. |
| 2007/0101360 A1 | 5/2007 | Gutta et al. |
| 2007/0106170 A1 | 5/2007 | Dunseath, Jr. et al. |
| 2007/0112460 A1 | 5/2007 | Kiselik |
| 2007/0135727 A1 | 6/2007 | Virtanen et al. |

(56) References Cited

U.S. PATENT DOCUMENTS

| | | |
|---|---|---|
| 2007/0135728 A1 | 6/2007 | Snyder et al. |
| 2007/0136753 A1 | 6/2007 | Bovenschulte et al. |
| 2007/0150281 A1* | 6/2007 | Hoff .................... G06Q 30/02 704/270 |
| 2007/0150916 A1 | 6/2007 | Begole et al. |
| 2007/0209047 A1 | 9/2007 | Hallberg et al. |
| 2007/0214471 A1 | 9/2007 | Rosenberg |
| 2007/0225585 A1 | 9/2007 | Washbon et al. |
| 2007/0225674 A1 | 9/2007 | Molnar et al. |
| 2007/0226760 A1 | 9/2007 | Neuhauser et al. |
| 2007/0235716 A1 | 10/2007 | Delic et al. |
| 2007/0238945 A1 | 10/2007 | Delic et al. |
| 2007/0244977 A1 | 10/2007 | Atkins |
| 2007/0250846 A1 | 10/2007 | Swix et al. |
| 2007/0250901 A1 | 10/2007 | McIntire et al. |
| 2007/0265507 A1 | 11/2007 | de Lemos |
| 2007/0282566 A1 | 12/2007 | Whitlow et al. |
| 2007/0294132 A1 | 12/2007 | Zhang et al. |
| 2007/0294705 A1 | 12/2007 | Gopalakrishnan et al. |
| 2007/0294706 A1 | 12/2007 | Neuhauser et al. |
| 2008/0001600 A1 | 1/2008 | deCharms |
| 2008/0004940 A1 | 1/2008 | Rolleston Phillips |
| 2008/0010110 A1 | 1/2008 | Neuhauser et al. |
| 2008/0024725 A1 | 1/2008 | Todd |
| 2008/0027345 A1 | 1/2008 | Kumada et al. |
| 2008/0040740 A1 | 2/2008 | Plotnick et al. |
| 2008/0043013 A1 | 2/2008 | Gruttadauria et al. |
| 2008/0059997 A1 | 3/2008 | Plotnick et al. |
| 2008/0065468 A1 | 3/2008 | Berg et al. |
| 2008/0065721 A1 | 3/2008 | Cragun |
| 2008/0081961 A1 | 4/2008 | Westbrook et al. |
| 2008/0082019 A1 | 4/2008 | Ludving et al. |
| 2008/0086356 A1 | 4/2008 | Glassman et al. |
| 2008/0091463 A1 | 4/2008 | Shakamuri |
| 2008/0091512 A1 | 4/2008 | Marci et al. |
| 2008/0097854 A1 | 4/2008 | Young |
| 2008/0109840 A1 | 5/2008 | Walter et al. |
| 2008/0125110 A1 | 5/2008 | Ritter |
| 2008/0133724 A1 | 6/2008 | Clark |
| 2008/0147448 A1 | 6/2008 | Tunick et al. |
| 2008/0147742 A1 | 6/2008 | Allen |
| 2008/0152300 A1 | 6/2008 | Knee et al. |
| 2008/0162182 A1 | 7/2008 | Cazares et al. |
| 2008/0177197 A1 | 7/2008 | Lee et al. |
| 2008/0195471 A1 | 8/2008 | Dube et al. |
| 2008/0204273 A1 | 8/2008 | Crystal et al. |
| 2008/0208072 A1 | 8/2008 | Fadem et al. |
| 2008/0214902 A1 | 9/2008 | Lee et al. |
| 2008/0218472 A1 | 9/2008 | Breen et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0228077 A1 | 9/2008 | Wilk et al. |
| 2008/0249865 A1 | 10/2008 | Angell et al. |
| 2008/0255949 A1 | 10/2008 | Genco et al. |
| 2008/0263458 A1 | 10/2008 | Altberg et al. |
| 2008/0295126 A1 | 11/2008 | Lee et al. |
| 2008/0306398 A1 | 12/2008 | Uchiyama et al. |
| 2009/0018996 A1 | 1/2009 | Hunt et al. |
| 2009/0024049 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0024747 A1 | 1/2009 | Moses et al. |
| 2009/0025023 A1 | 1/2009 | Pradeep et al. |
| 2009/0025024 A1 | 1/2009 | Beser et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030762 A1 | 1/2009 | Lee et al. |
| 2009/0030780 A1 | 1/2009 | York et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0037575 A1 | 2/2009 | Crystal et al. |
| 2009/0060240 A1 | 3/2009 | Coughlan et al. |
| 2009/0062629 A1 | 3/2009 | Pradeep et al. |
| 2009/0062679 A1 | 3/2009 | Tan et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0069652 A1 | 3/2009 | Lee et al. |
| 2009/0070798 A1 | 3/2009 | Lee et al. |
| 2009/0082643 A1 | 3/2009 | Pradeep et al. |
| 2009/0082689 A1 | 3/2009 | Guttag et al. |
| 2009/0082692 A1 | 3/2009 | Hale et al. |
| 2009/0083129 A1 | 3/2009 | Pradeep et al. |
| 2009/0088610 A1 | 4/2009 | Lee et al. |
| 2009/0089830 A1 | 4/2009 | Chandratillake et al. |
| 2009/0094286 A1 | 4/2009 | Lee et al. |
| 2009/0094627 A1 | 4/2009 | Lee et al. |
| 2009/0094628 A1 | 4/2009 | Lee et al. |
| 2009/0094629 A1 | 4/2009 | Lee et al. |
| 2009/0097689 A1 | 4/2009 | Prest et al. |
| 2009/0098524 A1 | 4/2009 | Walton |
| 2009/0099873 A1 | 4/2009 | Kurple |
| 2009/0112077 A1 | 4/2009 | Nguyen et al. |
| 2009/0112117 A1 | 4/2009 | Rewari |
| 2009/0119154 A1 | 5/2009 | Jung et al. |
| 2009/0131764 A1 | 5/2009 | Lee et al. |
| 2009/0132441 A1 | 5/2009 | Muller et al. |
| 2009/0133047 A1 | 5/2009 | Lee et al. |
| 2009/0138356 A1 | 5/2009 | Pomplun |
| 2009/0144780 A1 | 6/2009 | Toebes et al. |
| 2009/0150919 A1 | 6/2009 | Lee et al. |
| 2009/0150920 A1 | 6/2009 | Jones |
| 2009/0153328 A1 | 6/2009 | Otani et al. |
| 2009/0156907 A1 | 6/2009 | Jung et al. |
| 2009/0156955 A1 | 6/2009 | Jung et al. |
| 2009/0158308 A1 | 6/2009 | Weitzenfeld et al. |
| 2009/0163777 A1 | 6/2009 | Jung et al. |
| 2009/0164132 A1 | 6/2009 | Jung et al. |
| 2009/0024447 A1 | 7/2009 | Pradeep et al. |
| 2009/0171164 A1 | 7/2009 | Jung et al. |
| 2009/0187467 A1 | 7/2009 | Fang et al. |
| 2009/0195392 A1 | 8/2009 | Zalewski |
| 2009/0214060 A1 | 8/2009 | Chuang et al. |
| 2009/0216611 A1 | 8/2009 | Leonard et al. |
| 2009/0221928 A1 | 9/2009 | Einav et al. |
| 2009/0248484 A1 | 10/2009 | Surendran et al. |
| 2009/0248496 A1 | 10/2009 | Hueter et al. |
| 2009/0248594 A1 | 10/2009 | Castleman et al. |
| 2009/0249223 A1 | 10/2009 | Barsook et al. |
| 2009/0253996 A1 | 10/2009 | Lee et al. |
| 2009/0259137 A1 | 10/2009 | Delic et al. |
| 2009/0259509 A1 | 10/2009 | Landvater |
| 2009/0271294 A1 | 10/2009 | Hadi |
| 2009/0287108 A1 | 11/2009 | Levy |
| 2009/0292587 A1 | 11/2009 | Fitzgerald |
| 2009/0300672 A1 | 12/2009 | Van Gulik |
| 2009/0305006 A1 | 12/2009 | Steffen |
| 2009/0318773 A1 | 12/2009 | Jung et al. |
| 2009/0318826 A1 | 12/2009 | Green et al. |
| 2009/0327068 A1 | 12/2009 | Pradeep et al. |
| 2009/0328089 A1 | 12/2009 | Pradeep et al. |
| 2009/0328122 A1 | 12/2009 | Amento et al. |
| 2010/0004977 A1 | 1/2010 | Marci et al. |
| 2010/0022821 A1 | 1/2010 | Dubi et al. |
| 2010/0030578 A1 | 2/2010 | Siddique et al. |
| 2010/0041962 A1 | 2/2010 | Causevic et al. |
| 2010/0042012 A1 | 2/2010 | Alhussiny |
| 2010/0060300 A1 | 3/2010 | Muller et al. |
| 2010/0063881 A1 | 3/2010 | Ghosh et al. |
| 2010/0094702 A1 | 4/2010 | Silberstein |
| 2010/0121716 A1 | 5/2010 | Golan |
| 2010/0125219 A1 | 5/2010 | Harris et al. |
| 2010/0145176 A1 | 6/2010 | Himes |
| 2010/0145215 A1 | 6/2010 | Pradeep et al. |
| 2010/0145217 A1 | 6/2010 | Otto et al. |
| 2010/0153175 A1 | 6/2010 | Pearson et al. |
| 2010/0169153 A1 | 7/2010 | Hwacinski et al. |

(56) References Cited

U.S. PATENT DOCUMENTS

| | | |
|---|---|---|
| 2010/0169162 A1 | 7/2010 | Anderson et al. |
| 2010/0179881 A1 | 7/2010 | Wiederstein |
| 2010/0180029 A1 | 7/2010 | Fourman |
| 2010/0183279 A1 | 7/2010 | Pradeep et al. |
| 2010/0186031 A1 | 7/2010 | Pradeep et al. |
| 2010/0186032 A1 | 7/2010 | Pradeep et al. |
| 2010/0198042 A1 | 8/2010 | Popescu et al. |
| 2010/0211439 A1 | 8/2010 | Marci et al. |
| 2010/0214318 A1 | 8/2010 | Pradeep et al. |
| 2010/0215289 A1 | 8/2010 | Pradeep et al. |
| 2010/0218208 A1 | 8/2010 | Holden |
| 2010/0223094 A1 | 9/2010 | Cumming et al. |
| 2010/0228604 A1 | 9/2010 | Desai et al. |
| 2010/0228614 A1 | 9/2010 | Zhang et al. |
| 2010/0234752 A1 | 9/2010 | Sullivan et al. |
| 2010/0241580 A1 | 9/2010 | Schleier-Smith |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0250347 A1 | 9/2010 | Rainier et al. |
| 2010/0250458 A1 | 9/2010 | Ho |
| 2010/0257052 A1 | 10/2010 | Zito et al. |
| 2010/0263005 A1 | 10/2010 | White |
| 2010/0268540 A1 | 10/2010 | Arshi et al. |
| 2010/0268573 A1 | 10/2010 | Jain et al. |
| 2010/0268720 A1 | 10/2010 | Spivack et al. |
| 2010/0269127 A1 | 10/2010 | Krug |
| 2010/0274152 A1 | 10/2010 | McPeck et al. |
| 2010/0274153 A1 | 10/2010 | Tucker et al. |
| 2010/0287152 A1 | 11/2010 | Hauser |
| 2010/0292998 A1 | 11/2010 | Bodlaender et al. |
| 2010/0306030 A1 | 12/2010 | Mawani |
| 2010/0306120 A1 | 12/2010 | Ciptawilangga |
| 2010/0317988 A1 | 12/2010 | Terada et al. |
| 2010/0318507 A1 | 12/2010 | Grant et al. |
| 2010/0325660 A1 | 12/2010 | Holden |
| 2010/0331661 A1 | 12/2010 | Nakagawa |
| 2010/0332319 A1 | 12/2010 | Etchegoyen |
| 2010/0332331 A1 | 12/2010 | Etchegoyen |
| 2011/0004089 A1 | 1/2011 | Chou |
| 2011/0015503 A1 | 1/2011 | Joffe et al. |
| 2011/0020778 A1 | 1/2011 | Forbes |
| 2011/0022459 A1 | 1/2011 | Milanese et al. |
| 2011/0022965 A1 | 1/2011 | Lawrence et al. |
| 2011/0040155 A1 | 2/2011 | Guzak et al. |
| 2011/0040202 A1 | 2/2011 | Luo et al. |
| 2011/0043759 A1 | 2/2011 | Bushinsky |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047035 A1 | 2/2011 | Gidwani et al. |
| 2011/0047121 A1 | 2/2011 | Pradeep et al. |
| 2011/0059422 A1 | 3/2011 | Masaoka |
| 2011/0071874 A1 | 3/2011 | Schneersohn et al. |
| 2011/0076942 A1 | 3/2011 | Taveau et al. |
| 2011/0084795 A1 | 4/2011 | Fukuyori |
| 2011/0085700 A1 | 4/2011 | Lee |
| 2011/0098593 A1 | 4/2011 | Low et al. |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0119130 A1 | 5/2011 | Agan et al. |
| 2011/0131274 A1 | 6/2011 | Hille |
| 2011/0144519 A1 | 6/2011 | Causevic |
| 2011/0153390 A1 | 6/2011 | Harris |
| 2011/0153391 A1 | 6/2011 | Tenbrock |
| 2011/0208515 A1 | 8/2011 | Neuhauser |
| 2011/0224569 A1 | 9/2011 | Isenhart et al. |
| 2011/0237923 A1 | 9/2011 | Picht et al. |
| 2011/0237971 A1 | 9/2011 | Pradeep et al. |
| 2011/0248729 A2 | 10/2011 | Mueller et al. |
| 2011/0257502 A1 | 10/2011 | Lee |
| 2011/0257937 A1 | 10/2011 | Lee |
| 2011/0270620 A1 | 11/2011 | Pradeep et al. |
| 2011/0276504 A1 | 11/2011 | Pradeep et al. |
| 2011/0282231 A1 | 11/2011 | Pradeep et al. |
| 2011/0282232 A1 | 11/2011 | Pradeep et al. |
| 2011/0282749 A1 | 11/2011 | Pradeep et al. |
| 2011/0298706 A1 | 12/2011 | Mann |
| 2011/0319975 A1 | 12/2011 | Ho et al. |
| 2012/0002848 A1 | 1/2012 | Hill |
| 2012/0004899 A1 | 1/2012 | Arshi |
| 2012/0022391 A1 | 1/2012 | Leuthardt |
| 2012/0036004 A1 | 2/2012 | Pradeep et al. |
| 2012/0036005 A1 | 2/2012 | Pradeep et al. |
| 2012/0046993 A1 | 2/2012 | Hill |
| 2012/0054018 A1 | 3/2012 | Pradeep et al. |
| 2012/0072289 A1 | 3/2012 | Pradeep et al. |
| 2012/0083668 A1 | 4/2012 | Pradeep et al. |
| 2012/0084139 A1 | 4/2012 | Pradeep et al. |
| 2012/0108995 A1 | 5/2012 | Pradeep et al. |
| 2012/0114305 A1 | 5/2012 | Holden |
| 2012/0130800 A1 | 5/2012 | Pradeep et al. |
| 2012/0173701 A1 | 7/2012 | Tenbrock |
| 2012/0203363 A1 | 8/2012 | McKenna et al. |
| 2012/0203559 A1 | 8/2012 | McKenna et al. |
| 2012/0239407 A1 | 9/2012 | Lynch et al. |
| 2012/0245978 A1 | 9/2012 | Jain et al. |
| 2012/0284112 A1 | 11/2012 | Pradeep et al. |
| 2012/0284332 A1 | 11/2012 | Pradeep et al. |
| 2012/0290409 A1 | 11/2012 | Pradeep et al. |
| 2013/0022948 A1 | 1/2013 | Angell et al. |
| 2013/0024272 A1 | 1/2013 | Pradeep et al. |
| 2013/0046577 A1 | 2/2013 | Marci et al. |
| 2013/0094722 A1 | 4/2013 | Hill |
| 2013/0097715 A1 | 4/2013 | Fourman |
| 2013/0124365 A1 | 5/2013 | Pradeep |
| 2013/0124623 A1 | 5/2013 | Munter |
| 2013/0152506 A1 | 6/2013 | Pradeep |
| 2013/0166373 A1 | 6/2013 | Pradeep et al. |
| 2013/0185140 A1 | 7/2013 | Pradeep et al. |
| 2013/0185141 A1 | 7/2013 | Pradeep et al. |
| 2013/0185142 A1 | 7/2013 | Pradeep et al. |
| 2013/0185144 A1 | 7/2013 | Pradeep et al. |
| 2013/0185145 A1 | 7/2013 | Pradeep et al. |
| 2013/0268279 A1 | 10/2013 | Srinivasan et al. |
| 2013/0304540 A1 | 11/2013 | Pradeep et al. |
| 2013/0332259 A1 | 12/2013 | Pradeep et al. |
| 2014/0162225 A1 | 6/2014 | Hill |
| 2014/0244345 A1 | 8/2014 | Sollis et al. |
| 2017/0039591 A1 | 2/2017 | Knight et al. |
| 2018/0247332 A1 | 8/2018 | Pradeep et al. |
| 2018/0341977 A1 | 11/2018 | Knight et al. |
| 2019/0005532 A1 | 1/2019 | Pradeep et al. |
| 2019/0034958 A1 | 1/2019 | Pradeep et al. |
| 2019/0034959 A1 | 1/2019 | Pradeep et al. |
| 2019/0139078 A1 | 5/2019 | Pradeep et al. |
| 2019/0156352 A1 | 5/2019 | Pradeep et al. |
| 2019/0220888 A1 | 7/2019 | Knight et al. |
| 2019/0282153 A1 | 9/2019 | Pradeep et al. |
| 2020/0005339 A1 | 1/2020 | Pradeep et al. |
| 2020/0163571 A1 | 5/2020 | Pradeep et al. |
| 2020/0234329 A1 | 7/2020 | Pradeep et al. |
| 2020/0258116 A1 | 8/2020 | Pradeep et al. |
| 2020/0351250 A1* | 11/2020 | Redmond .......... H04N 21/2223 |
| 2020/0364741 A1 | 11/2020 | Pradeep et al. |
| 2020/0397330 A1* | 12/2020 | Kobayashi ............. A61B 5/369 |

FOREIGN PATENT DOCUMENTS

| | | |
|---|---|---|
| GB | 1374658 | 11/1974 |
| GB | 2221759 | 2/1990 |
| JP | 2001147944 | 5/2001 |
| JP | 2005-160805 | 12/2003 |
| JP | 2005051654 | 2/2005 |
| JP | 2006006355 | 1/2006 |
| JP | 2006227994 | 8/2006 |
| JP | 2006-305334 | 11/2006 |
| JP | 2007310454 | 11/2007 |
| KR | 200422399 | 7/2006 |
| WO | 95-018565 | 7/1995 |

(56) References Cited

FOREIGN PATENT DOCUMENTS

| WO | 1997-017774 | 5/1997 |
|---|---|---|
| WO | 1997-040745 | 11/1997 |
| WO | 1997-041673 | 11/1997 |
| WO | 02-100241 | 12/2002 |
| WO | 02-102238 | 12/2002 |
| WO | 2004-049225 | 6/2004 |
| WO | 2006-009771 | 1/2006 |
| WO | 2008030831 | 3/2008 |
| WO | 2008055078 | 5/2008 |
| WO | 2008-064431 | 6/2008 |
| WO | 2008072739 | 6/2008 |
| WO | 2008-077178 | 7/2008 |
| WO | 2008-109694 | 9/2008 |
| WO | 2008-109699 | 9/2008 |
| WO | 2008-121651 | 10/2008 |
| WO | 2008-137579 | 11/2008 |
| WO | 2008-137581 | 11/2008 |
| WO | 2008-141340 | 11/2008 |
| WO | 2008-154410 | 12/2008 |
| WO | 2009-018374 | 2/2009 |
| WO | 2009-052833 | 4/2009 |

OTHER PUBLICATIONS

Hearing Notice issued by the Indian Patent Office in connection with Indian Patent Application No. 6145/CHENP/2009, on Mar. 12, 2020, 2 pages.
Notice of Allowance, issued by the United States Patent and Trademark Office in connection with U.S. Appl. No. 16/183,131, dated Mar. 24, 2020, 8 pages.
Non-Final Office Action, issued by the United States Patent and Trademark Office in connection with U.S. Appl. No. 16/151,044, dated Apr. 2, 2020, 5 pages.
Non-Final Office Action, issued by the United States Patent and Trademark Office in connection with U.S. Appl. No. 16/151,050, dated Apr. 6, 2020, 13 pages.
Final Office Action, issued by the United States Patent and Trademark Office in connection with U.S. Appl. No. 12/546,586, dated Jul. 24, 2020, 14 pages.
Non-Final Office Action, issued by the United States Patent and Trademark Office in connection with U.S. Appl. No. 16/193,930, dated Jul. 27, 2020, 12 pages.
Non-Final Office Action, issued by the United States Patent and Trademark Office in connection with U.S. Appl. No. 16/421,864, dated Aug. 13, 2020, 24 pages.
Final Office Action, issued by the United States Patent and Trademark Office in connection with U.S. Appl. No. 16/151,050, dated Oct. 7, 2020, 5 pages.
Notice of Allowance, issued by the United States Patent and Trademark Office in connection with U.S. Appl. No. 16/151,044, dated Oct. 9, 2020, 8 pages.
Non-Final Office Action, issued by the United States Patent and Trademark Office in connection with U.S. Appl. No. 16/790,160, dated Oct. 29, 2020, 5 pages.
Notice of Allowance, issued by the United States Patent and Trademark Office in connection with U.S. Appl. No. 16/193,930, dated Nov. 18, 2020, 8 pages.
Kim et al., "Design for an Interactive Television Advertising System," Proceedings for the 39th Hawaii International Conference on System Sciences (2006), 9 pages.
Notice of Allowance, issued by the United States Patent and Trademark Office in connection with U.S. Appl. No. 12/546,586, dated Dec. 9, 2020, 8 pages.
Notice of Allowance, issued by the United States Patent and Trademark Office in connection with U.S. Appl. No. 16/151,050, dated Jan. 22, 2021, 8 pages.
Final Office Action, issued by the United States Patent and Trademark Office in connection with U.S. Appl. No. 16/421,864, dated Jan. 25, 2021, 26 pages.

Notice of Allowance, issued by the United States Patent and Trademark Office in connection with U.S. Appl. No. 16/790,160, dated Feb. 22, 2021, 9 pages.
Non-Final Office Action, issued by the United States Patent and Trademark Office in connection with U.S. Appl. No. 16/692,511, dated Feb. 24, 2021, 12 pages.
"One to One Interactive and Innerscope Research Release Preliminary Biomeasures Study Results," PR Newswire, Feb. 28, 2007, 4 pages.
Non-Final Office Action, issued by the United States Patent and Trademark Office in connection with U.S. Appl. No. 16/360,282, dated Mar. 18, 2021, 7 pages.
Non-Final Office Action, issued by the United States Patent and Trademark Office in connection with U.S. Appl. No. 16/421,864, dated Apr. 22, 2021, 18 pages.
Final Rejection, issued by the United States Patent and Trademark Office in connection with U.S. Appl. No. 12/056,211, dated Jul. 8, 2011, 16 pages.
Office Action, issued by the United States Patent and Trademark Office in connection with U.S. Appl. No. 12/056,211, dated Jan. 7, 2011, 19 pages.
Office Action issued by the United States Patent and Trademark Office in connection with U.S. Appl. No. 12/056,221, dated Apr. 15, 2011, 24 pages.
Final Rejection, issued by the United States Patent and Trademark Office in connection with U.S. Appl. No. 12/113,863, dated Jun. 9, 2011, 12 pages.
Office Action, issued by the United States Patent and Trademark Office in connection with U.S. Appl. No. 12/113,863, dated Dec. 27, 2010, 15 pages.
Final Rejection, issued by the United States Patent and Trademark Office in connection with U.S. Appl. No. 12/113,870, dated Apr. 21, 2011, 10 pages.
Office Action, issued by the United States Patent and Trademark Office in connection with U.S. Appl. No. 12/113,870, dated Dec. 3, 2010, 12 pages.
Office Action, issued by the United States Patent and Trademark Office in connection with U.S. Appl. No. 12/122,240, dated Jun. 10, 2011, 12 pages.
Final Rejection, issued by the United States Patent and Trademark Office in connection with U.S. Appl. No. 12/122,262, dated May 26, 2011, 15 pages.
Office Action, issued by the United States Patent and Trademark Office in connection with U.S. Appl. No. 12/122,262, dated Dec. 9, 2010, 13 pages.
Final Rejection, issued by the United States Patent and Trademark Office in connection with U.S. Appl. No. 12/135,066, dated Jan. 21, 2011, 16 pages.
Office Action, issued by the United States Patent and Trademark Office in connection with U.S. Appl. No. 12/135,066, dated Oct. 28, 2010, 14 pages.
Notice of Panel Decision from Pre-Appeal Brief Review, issued by the United States Patent and Trademark Office in connection with U.S. Appl. No. 12/135,066, on May 31, 2011, 2 pages.
Office Action, issued by the United States Patent and Trademark Office in connection with U.S. Appl. No. 12/135,074, dated Dec. 23, 2010, 14 pages.
Final Rejection, issued by the United States Patent and Trademark Office in connection with U.S. Appl. No. 12/135,074, dated Jun. 9, 2011, 10 pages.
Final Rejection, issued by the United States Patent and Trademark Office in connection with U.S. Appl. No. 12/182,874, dated Jul. 7, 2011, 14 pages.
Office Action, issued by the United States Patent and Trademark Office in connection with U.S. Appl. No. 12/182,874, dated Dec. 27, 2010, 17 pages.
Office Action, issued by the United States Patent and Trademark Office in connection with U.S. Appl. No. 12/199,557, dated Dec. 27, 2010, 14 pages.
Final Rejection, issued by the United States Patent and Trademark Office in connection with U.S. Appl. No. 12/199,557, dated Jun. 9, 2011, 12 pages.

(56) References Cited

OTHER PUBLICATIONS

Final Rejection, issued by the United States Patent and Trademark Office in connection with U.S. Appl. No. 12/199,583, dated Jun. 21, 2011, 14 pages.
Office Action, issued by the United States Patent and Trademark Office in connection with U.S. Appl. No. 12/199,583, dated Dec. 27, 2010, 17 pages.
Final Rejection, issued by the United States Patent and Trademark Office in connection with U.S. Appl. No. 12/199,596, dated Jun. 14, 2011, 13 pages.
Office Action, issued by the United States Patent and Trademark Office in connection with U.S. Appl. No. 12/199,596, dated Dec. 27, 2010, 17 pages.
Final Rejection, issued by the United States Patent and Trademark Office in connection with U.S. Appl. No. 12/200,813, dated Jul. 6, 2011, 13 pages.
Office Action, issued by the United States Patent and Trademark Office in connection with U.S. Appl. No. 12/200,813, dated Dec. 27, 2010, 14 pages.
Office Action, issued by the United States Patent and Trademark Office in connection with U.S. Appl. No. 12/234,372, dated Jun. 7, 2011, 10 pages.
Final Rejection, issued by the United States Patent and Trademark Office in connection with U.S. Appl. No. 12/135,069, dated Feb. 17, 2011, 32 pages.
Office Action, issued by the United States Patent and Trademark Office in connection with U.S. Appl. No. 12/135,069, dated Oct. 29, 2010, 21 pages.
Office Action, issued by the United States Patent and Trademark Office in connection with U.S. Appl. No. 12/357,315, dated May 4, 2011, 9 pages.
Office Action, issued by the United States Patent and Trademark Office in connection with U.S. Appl. No. 12/410,380, dated Jun. 7, 2011, 9 pages.
Office Action, issued by the United States Patent and Trademark Office in connection with U.S. Appl. No. 12/413,297, dated Jul. 18, 2011, 9 pages.
Office Action, issued by the United States Patent and Trademark Office in connection with U.S. Appl. No. 12/608,685,dated Jul. 12, 2011, 15 pages.
Office Action, issued by the United States Patent and Trademark Office in connection with U.S. Appl. No. 12/056,190,dated Aug. 10, 2011, 28 pages.
Office Action, issued by the United States Patent and Trademark Office in connection with U.S. Appl. No. 12/357,322,dated Aug. 23, 2011, 12 pages.
Office Action, issued by the United States Patent and Trademark Office in connection with U.S. Appl. No. 12/135,069,dated Aug. 26, 2011, 33 pages.
Restriction Requirement, issued by the United States Patent and Trademark Office in connection with U.S. Appl. No. 12/122,253,dated Sep. 2, 2011, 7 pages.
Office Action, issued by the United States Patent and Trademark Office in connection with U.S. Appl. No. 12/410,372, dated Sep. 12, 2011, 12 pages.
Restriction Requirement, issued by the United States Patent and Trademark Office in connection with U.S. Appl. No. 12/182,851, dated Sep. 12, 2011, 7 pages.
Office Action, issued by the United States Patent and Trademark Office in connection with U.S. Appl. No. 12/135,066, dated Sep. 29, 2011, 37 pages.
Restriction Requirement, issued by the United States Patent and Trademark Office in connection with U.S. Appl. No. 12/056,225, dated Oct. 3, 2011, 6 pages.
Office Action, issued by the United States Patent and Trademark Office in connection with U.S. Appl. No. 12/234,388, dated Oct. 12, 2011, 27 pages.
Office Action, issued by the United States Patent and Trademark Office in connection with U.S. Appl. No. 12/234,372, dated Oct. 13, 2011, 22 pages.
Office Action, issued by the United States Patent and Trademark Office in connection with U.S. Appl. No. 12/410,380, dated Oct. 19, 2011, 21 pages.
Office Action, issued by the United States Patent and Trademark Office in connection with U.S. Appl. No. 12/357,315, dated Oct. 26, 2011, 41 pages.
Office Action, issued by the United States Patent and Trademark Office in connection with U.S. Appl. No. 12/122,240, dated Oct. 27, 2011, 39 pages.
Final Rejection, issued by the United States Patent and Trademark Office in connection with U.S. Appl. No. 12/056,221, dated Nov. 28, 2011, 44 pages.
Office Action, issued by the United States Patent and Trademark Office in connection with U.S. Appl. No. 12/608,660, dated Dec. 7, 2011, 8 pages.
Office Action, issued by the United States Patent and Trademark Office in connection with U.S. Appl. No. 12/113,863, dated Dec. 22, 2011, 17 pages.
Office Action, issued by the United States Patent and Trademark Office in connection with U.S. Appl. No. 12/122,262, dated Dec. 22, 2011, 17 pages.
Office Action, issued by the United States Patent and Trademark Office in connection with U.S. Appl. No. 12/135,074, dated Dec. 22, 2011, 16 pages.
Office Action, issued by the United States Patent and Trademark Office in connection with U.S. Appl. No. 12/199,557, dated Dec. 22, 2011, 17 pages.
Office Action, issued by the United States Patent and Trademark Office in connection with U.S. Appl. No. 12/199,596, dated Dec. 22, 2011, 15 pages.
Office Action, issued by the United States Patent and Trademark Office in connection with U.S. Appl. No. 12/200,813, dated Dec. 22, 2011, 18 pages.
Office Action, issued by the United States Patent and Trademark Office in connection with U.S. Appl. No. 12/199,583, dated Dec. 29, 2011, 18 pages.
Final Rejection, issued by the United States Patent and Trademark Office in connection with U.S. Appl. No. 12/410,372, dated Jan. 3, 2012, 10 pages.
Final Rejection, issued by the United States Patent and Trademark Office in connection with U.S. Appl. No. 12/413,297, dated Jan. 4, 2012, 10 pages.
Office Action, issued by the United States Patent and Trademark Office in connection with U.S. Appl. No. 12/544,921, dated Jan. 9, 2012, 13 pages.
Office Action, issued by the United States Patent and Trademark Office in connection with U.S. Appl. No. 12/357,302, dated Jan. 17, 2012, 11 pages.
Office Action, issued by the United States Patent and Trademark Office in connection with U.S. Appl. No. 12/056,225, dated Jan. 20, 2012, 12 pages.
Final Rejection, issued by the United States Patent and Trademark Office in connection with U.S. Appl. No. 12/135,066, dated Jan. 24, 2012, 12 pages.
Office Action, issued by the United States Patent and Trademark Office in connection with U.S. Appl. No. 12/546,586, dated Feb. 1, 2012, 17 pages.
Restriction Requirement, issued by the United States Patent and Trademark Office in connection with U.S. Appl. No. 12/544,958, dated Feb. 10, 2012, 6 pages.
Final Rejection, issued by the United States Patent and Trademark Office in connection with U.S. Appl. No. 12/135,069, dated Feb. 14, 2012, 36 pages.
Final Rejection, issued by the United States Patent and Trademark Office in connection with U.S. Appl. No. 12/357,322, dated Feb. 14, 2012, 14 pages.
Office Action, issued by the United States Patent and Trademark Office in connection with U.S. Appl. No. 12/056,211, dated Feb. 16, 2012, 16 pages.
Final Rejection, issued by the United States Patent and Trademark Office in connection with U.S. Appl. No. 12/056,190, dated Feb. 17, 2012, 22 pages.

(56) References Cited

OTHER PUBLICATIONS

Office Action, issued by the United States Patent and Trademark Office in connection with U.S. Appl. No. 12/122,253, dated Feb. 17, 2012, 20 pages.
Office Action, issued by the United States Patent and Trademark Office in connection with U.S. Appl. No. 12/182,874, dated Feb. 17, 2012, 15 pages.
Office Action, issued by the United States Patent and Trademark Office in connection with U.S. Appl. No. 12/868,531, dated Mar. 1, 2012, 7 pages.
Office Action, issued by the United States Patent and Trademark Office in connection with U.S. Appl. No. 12/182,851, dated Mar. 14, 2012, 17 pages.
Office Action, issued by the United States Patent and Trademark Office in connection with U.S. Appl. No. 12/608,685, dated Mar. 29, 2012, 17 pages.
Office Action, issued by the United States Patent and Trademark Office in connection with U.S. Appl. No. 12/846,242, dated Mar. 29, 2012, 16 pages.
Office Action, issued by the United States Patent and Trademark Office in connection with U.S. Appl. No. 12/234,388, dated Apr. 6, 2012, 6 pages.
Office Action, issued by the United States Patent and Trademark Office in connection with U.S. Appl. No. 12/357,315, dated Apr. 9, 2012, 17 pages.
Office Action, issued by the United States Patent and Trademark Office in connection with U.S. Appl. No. 12/544,958, dated May 2, 2012, 15 pages.
Notice of Allowance, issued by the United States Patent and Trademark Office in connection with U.S. Appl. No. 12/357,302, dated May 7, 2012, 11 pages.
Notice of Allowance, issued by the United States Patent and Trademark Office in connection with U.S. Appl. No. 12/868,531, dated May 8, 2012, 11 pages.
Notice of Allowance, issued by the United States Patent and Trademark Office in connection with U.S. Appl. No. 12/608,696, dated May 15, 2012, 6 pages.
Restriction Requirement, issued by the United States Patent and Trademark Office in connection with U.S. Appl. No. 12/545,455, dated Jun. 13, 2012, 5 pages.
Office Action, issued by the United States Patent and Trademark Office in connection with U.S. Appl. No. 12/056,225, dated Jun. 15, 2012, 9 pages.
Office Action, issued by the United States Patent and Trademark Office in connection with U.S. Appl. No. 12/544,934, dated Jun. 18, 2012, 11 pages.
Office Action, issued by the United States Patent and Trademark Office in connection with U.S. Appl. No. 12/135,066, dated Jun. 21, 2012, 10 pages.
Final Rejection, issued by the United States Patent and Trademark Office in connection with U.S. Appl. No. 12/608,660, dated Jul. 10, 2012, 14 pages.
Final Rejection, issued by the United States Patent and Trademark Office in connection with U.S. Appl. No. 12/608,685, dated Jul. 30, 2012, 15 pages.
Examiner's Answer, issued by the United States Patent and Trademark Office in connection with U.S. Appl. No. 12/410,372, dated Aug. 3, 2012, 8 pages.
Examiner's Answer, issued by the United States Patent and Trademark Office in connection with U.S. Appl. No. 12/410,380, dated Jun. 8, 2012, 12 pages.
Examiner's Answer, issued by the United States Patent and Trademark Office in connection with U.S. Appl. No. 12/234,372, dated May 23, 2012, 11 pages.
Advisory Action, issued by the United States Patent and Trademark Office in connection with U.S. Appl. No. 12/234,388, dated Aug. 28, 2012, 3 pages.
Office Action, issued by the United States Patent and Trademark Office in connection with U.S. Appl. No. 12/545,455, dated Aug. 29, 2012, 11 pages.
Office Action, issued by the United States Patent and Trademark Office in connection with U.S. Appl. No. 12/778,828, dated Aug. 30, 2012, 9 pages.
Office Action, issued by the United States Patent and Trademark Office in connection with U.S. Appl. No. 12/778,810, dated Aug. 31, 2012, 12 pages.
Notice of Allowance, issued by the United States Patent and Trademark Office in connection with U.S. Appl. No. 12/056,190, dated Sep. 17, 2012, 11 pages.
Notice of Allowance, issued by the United States Patent and Trademark Office in connection with U.S. Appl. No. 12/122,262, dated Sep. 17, 2012, 11 pages.
Final Rejection, issued by the United States Patent and Trademark Office in connection with U.S. Appl. No. 12/122,253, dated Sep. 17, 2012, 17 pages.
Examiner's Answer, issued by the United States Patent and Trademark Office in connection with U.S. Appl. No. 12/413,297, dated Sep. 18, 2012, 18 pages.
Final Rejection, issued by the United States Patent and Trademark Office in connection with U.S. Appl. No. 12/546,586, dated Sep. 18, 2012, 17 pages.
Notice of Allowance, issued by the United States Patent and Trademark Office in connection with U.S. Appl. No. 12/056,211, dated Sep. 19, 2012, 10 pages.
Notice of Allowance, issued by the United States Patent and Trademark Office in connection with U.S. Appl. No. 12/135,074, dated Sep. 19, 2012, 10 pages.
Notice of Allowance, issued by the United States Patent and Trademark Office in connection with U.S. Appl. No. 12/853,213, dated Sep. 7, 2012, 9 pages.
Notice of Allowance, issued by the United States Patent and Trademark Office in connection with U.S. Appl. No. 12/199,583, dated Sep. 26, 2012, 14 pages.
Notice of Allowance, issued by the United States Patent and Trademark Office in connection with U.S. Appl. No. 12/199,596, dated Sep. 27, 2012, 14 pages.
Notice of Allowance, issued by the United States Patent and Trademark Office in connection with U.S. Appl. No. 12/199,557, dated Sep. 28, 2012, 12 pages.
Notice of Allowance, issued by the United States Patent and Trademark Office in connection with U.S. Appl. No. 12/113,863, dated Oct. 1, 2012, 12 pages.
Office Action, issued by the United States Patent and Trademark Office in connection with U.S. Appl. No. 13/444,149, dated Oct. 4, 2012, 9 pages.
Final Office Action, issued by the United States Patent and Trademark Office in connection with U.S. Appl. No. 12/182,851, dated Oct. 4, 2012, 14 pages.
Office Action, issued by the United States Patent and Trademark Office in connection with U.S. Appl. No. 12/234,388, dated Oct. 5, 2012, 6 pages.
Notice of Allowance, issued by the United States Patent and Trademark Office in connection with U.S. Appl. No. 12/853,197, dated Oct. 16, 2012, 5 pages.
Notice of Allowance, issued by the United States Patent and Trademark Office in connection with U.S. Appl. No. 12/868,531, dated Oct. 22, 2012, 5 pages.
Final Office Action, issued by the United States Patent and Trademark Office in connection with U.S. Appl. No. 12/846,242, dated Nov. 29, 2012, 14 pages.
Notice of Allowance, issued by the United States Patent and Trademark Office in connection with U.S. Appl. No. 12/200,813, dated Oct. 30, 2012, 5 pages.
Notice of Allowance, issued by the United States Patent and Trademark Office in connection with U.S. Appl. No. 12/056,190, dated Nov. 2, 2012, 5 pages.
Restriction Requirement, issued by the United States Patent and Trademark Office in connection with U.S. Appl. No. 12/056,225, dated Nov. 2, 2012, 5 pages.
Final Office Action, issued by the United States Patent and Trademark Office in connection with U.S. Appl. No. 12/135,066, dated Nov. 13, 2012, 9 pages.

(56) References Cited

OTHER PUBLICATIONS

Notice of Allowance, issued by the United States Patent and Trademark Office in connection with U.S. Appl. No. 12/113,863, dated Nov. 16, 2012, 5 pages.
Notice of Allowance, issued by the United States Patent and Trademark Office in connection with U.S. Appl. No. 12/056,211, dated Nov. 21, 2012, 5 pages.
Notice of Allowance, issued by the United States Patent and Trademark Office in connection with U.S. Appl. No. 12/868,531, dated Nov. 23, 2012, 5 pages.
Office Action, issued by the United States Patent and Trademark Office in connection with U.S. Appl. No. 12/913,102, on Dec. 7, 2012, 7 pages.
Final Office Action, issued by the United States Patent and Trademark Office in connection with U.S. Appl. No. 12/544,958, dated Dec. 10, 2012, 16 pages.
Notice of Allowance, issued by the United States Patent and Trademark Office in connection with U.S. Appl. No. 12/853,197, dated Dec. 20, 2012, 5 pages.
Notice of Allowance, issued by the United States Patent and Trademark Office in connection with U.S. Appl. No. 12/056,190, dated Dec. 21, 2012, 14 pages.
Notice of Allowance, issued by the United States Patent and Trademark Office in connection with U.S. Appl. No. 12/056,211, dated Dec. 21, 2012, 10 pages.
Notice of Allowance, issued by the United States Patent and Trademark Office in connection with U.S. Appl. No. 12/122,262, dated Dec. 21, 2012, 19 pages.
Notice of Allowance, issued by the United States Patent and Trademark Office in connection with U.S. Appl. No. 12/135,074, dated Dec. 21, 2012, 12 pages.
Notice of Allowance, issued by the United States Patent and Trademark Office in connection with U.S. Appl. No. 12/199,557, dated Dec. 21, 2012, 14 pages.
Notice of Allowance, issued by the United States Patent and Trademark Office in connection with U.S. Appl. No. 12/199,596, dated Dec. 21, 2012, 17 pages.
Notice of Allowance, issued by the United States Patent and Trademark Office in connection with U.S. Appl. No. 12/200,813, dated Dec. 21, 2012, 9 pages.
Notice of Allowance, issued by the United States Patent and Trademark Office in connection with U.S. Appl. No. 12/853,213, dated Dec. 21, 2012, 10 pages.
Notice of Allowance, issued by the United States Patent and Trademark Office in connection with U.S. Appl. No. 12/868,531, dated Dec. 26, 2012, 2 pages.
Notice of Allowance, issued by the United States Patent and Trademark Office in connection with U.S. Appl. No. 12/113,863, dated Dec. 31, 2012, 5 pages.
Notice of Allowance, issued by the United States Patent and Trademark Office in connection with U.S. Appl. No. 12/199,583, dated Dec. 31, 2012, 10 pages.
Final Office Action, issued by the United States Patent and Trademark Office in connection with U.S. Appl. No. 12/182,874, dated Jan. 4, 2013, 17 pages.
Notice of Allowance, issued by the United States Patent and Trademark Office in connection with U.S. Appl. No. 12/199,583, dated Jan. 11, 2013, 11 pages.
Final Office Action, issued by the United States Patent and Trademark Office in connection with U.S. Appl. No. 12/056,225, dated Jan. 11, 2013, 11 pages.
Recertified IDS and Interview Summary, issued by the United States Patent and Trademark Office in connection with U.S. Appl. No. 12/853,197, dated Jan. 16, 2013, 6 pages.
Notice of Allowance, issued by the United States Patent and Trademark Office in connection with U.S. Appl. No. 12/199,557, dated Jan. 29, 2013, 17 pages.
Notice of Allowance, issued by the United States Patent and Trademark Office in connection with U.S. Appl. No. 12/853,197, on Jan. 29, 2013, 11 pages.

Notice of Allowance, issued by the United States Patent and Trademark Office in connection with U.S. Appl. No. 12/056,190, dated Jan. 31, 2013, 5 pages.
Notice of Allowance, issued by the United States Patent and Trademark Office in connection with U.S. Appl. No. 12/113,863, dated Jan. 31, 2013, 5 pages.
Notice of Allowance, issued by the United States Patent and Trademark Office in connection with U.S. Appl. No. 12/135,074, dated Jan. 31, 2013, 10 pages.
Notice of Allowance, issued by the United States Patent and Trademark Office in connection with U.S. Appl. No. 12/199,583, dated Feb. 1, 2013, 11 pages.
Notice of Allowance, issued by the United States Patent and Trademark Office in connection with U.S. Appl. No. 12/200,813, dated Feb. 1, 2013, 5pages.
Notice of Allowance, issued by the United States Patent and Trademark Office in connection with U.S. Appl. No. 12/056,211, dated Feb. 4, 2013, 5 pages.
Notice of Allowance, issued by the United States Patent and Trademark Office in connection with U.S. Appl. No. 12/122,262, dated Feb. 5, 2013, 15 pages.
Notice of Allowance, issued by the United States Patent and Trademark Office in connection with U.S. Appl. No. 12/868,531, dated Feb. 5, 2013, 8 pages.
Notice of Allowance, issued by the United States Patent and Trademark Office in connection with U.S. Appl. No. 12/853,213, dated Feb. 5, 2013, 10 pages.
Notice of Allowance, issued by the United States Patent and Trademark Office in connection with U.S. Appl. No. 12/234,388, dated Feb. 15, 2013, 9 pages.
Notice of Allowance, issued by the United States Patent and Trademark Office in connection with U.S. Appl. No. 12/056,190, dated Feb. 14, 2013, 5 pages.
Notice of Allowance, issued by the United States Patent and Trademark Office in connection with U.S. Appl. No. 12/200,813, dated Sep. 20, 2012, 11 pages.
Notice of Allowance, issued by the United States Patent and Trademark Office in connection with U.S. Appl. No. 12/182,874, dated Apr. 16, 2013, 10 pages.
Notice of Allowance, issued by the United States Patent and Trademark Office in connection with U.S. Appl. No. 12/182,874, dated Apr. 22, 2013, 11 pages.
International Preliminary Report on Patentability, issued by the International Bureau of WIPO in connection with International Application No. PCT/US08/058264, dated Sep. 29, 2009, 1 page.
International Search Report, issued by the International Searching Authority in connection with International Application No. PCT/US08/058264, dated Aug. 1, 2008, 2 pages.
Written Opinion, issued by the International Searching Authority in connection with International Application No. PCT/US08/058264, dated Aug. 1, 2008, 5 pages.
International Preliminary Report on Patentability, issued by the International Bureau of WIPO in connection with International Application No. PCT/US08/062273, dated Nov. 3, 2009, 1 page.
International Search Report, issued by the International Searching Authority in connection with International Application No. PCT/US08/062273, dated Sep. 5, 2008, 2 pages.
Written Opinion, issued by the International Searching Authority in connection with International Application No. PCT/US08/062273, dated Sep. 5, 2008, 4 pages.
International Search Report, issued by the International Searching Authority in connection with International Application No. PCT/US08/062275, dated Sep. 22, 2008, 2 pages.
Written Opinion, issued by the International Searching Authority in connection with International Application No. PCT/US08/062275, dated Sep. 22, 2008, 6 pages.
International Preliminary Report on Patentability, issued by the International Bureau of WIPO in connection with International Application No. PCT/US08/063984, dated Nov. 17, 2009, 1 page.
International Search Report, issued by the International Searching Authority in connection with International Application No. PCT/US08/063984, dated Sep. 29, 2008, 3 pages.

(56) References Cited

OTHER PUBLICATIONS

Written Opinion, issued by the International Searching Authority in connection with International Application No. PCT/US08/063984, dated Sep. 29, 2008, 4 pages.
International Preliminary Report on Patentability, issued by the International Bureau of WIPO in connection with International Application No. PCT/US08/063989, dated Nov. 17, 2009, 1 page.
International Search Report, issued by the International Searching Authority in connection with International Application No. PCT/US08/063989, dated Jul. 17, 2008, 2 pages.
Written Opinion, issued by the International Searching Authority in connection with International Application No. PCT/US08/063989, dated Jul. 17, 2008, 4 pages.
International Preliminary Report on Patentability, issued by the International Bureau of WIPO in connection with International Application No. PCT/US08/066166, dated Dec. 7, 2009, 1 page.
International Search Report, issued by the International Searching Authority in connection with International Application No. PCT/US08/066166, dated Aug. 25, 2008, 2 pages.
Written Opinion, issued by the International Searching Authority in connection with International Application No. PCT/US08/066166, dated Aug. 25, 2008, 6 pages.
International Preliminary Report on Patentability, issued by the International Bureau of WIPO in connection with International Application No. PCT/US08/071639, dated Feb. 2, 2010, 1 page.
Written Opinion, issued by the International Searching Authority in connection with International Application No. PCT/US08/071639, dated Oct. 22, 2008, 4 pages.
International Preliminary Report on Patentability, issued by the International Bureau of WIPO in connection with International Application No. PCT/US08/074467, dated Mar. 2, 2010, 1 page.
International Search Report, issued by the International Searching Authority in connection with International Application No. PCT/US08/074467, dated Nov. 17, 2008, 2 pages.
Written Opinion, issued by the International Searching Authority in connection with International Application No. PCT/US08/074467, dated Nov. 17, 2008, 4 pages.
International Preliminary Report of Patentability, issued by the International Bureau in connection with International Application No. PCT/US10/021535, dated Jul. 26, 2011, 1 page.
International Search Report, issued by the International Searching Authority in connection with International Application No. PCT/US10/021535, dated Mar. 23, 2010, 3 pages.
Written Opinion, issued by the International Searching Authority in connection with International Application No. PCT/US10/021535, dated Mar. 23, 2010, 4 pages.
International Preliminary Report of Patentability, issued by the International Bureau in connection with International Application No. PCT/US09/065368, dated Jun. 23, 2011, 2 pages.
International Search Report, issued by the International Searching Authority in connection with International Application No. PCT/US09/065368, dated Jan. 21, 2010, 3 pages.
Written Opinion, issued by the International Searching Authority in connection with International Application No. PCT/US09/065368, dated Jan. 21, 2010, 7 pages.
International Preliminary Report on Patentability, issued by the International Bureau of WIPO in connection with International Application No. PCT/US08/062275, dated Nov. 3, 2009, 1 page.
International Search Report, issued by the International Searching Authority in connection with International Application No. PCT/US08/071639, dated Oct. 22, 2008, 3 pages.
Extended European Search Report, issued by the European Patent Office in connection with European Application No. 08744383.4-2221/2130146, dated Jul. 27, 2011, 6 pages.
Extended European Search Report, issued by the European Patent Office in connection with European Application No. 10173095.0-2221, dated Dec. 17, 2010, 3 pages.
Extended European Search Report, issued by the European Patent Office in connection with European Application No. 10189294.1-2221, dated Mar. 21, 2011, 7 pages.

First Office Action, issued by the State Intellectual Property Office of P.R. China in connection with Patent Application No. 200880104982.1, dated Jan. 25, 2011, 15 pages (includes English translation).
English Translation of First Office Action, issued by the State Intellectual Property Office of P.R. China in connection with Patent Application No. 2008801015007, dated May 25, 2011, 8 pages.
English Translation of First Office Action, issued by the State Intellectual Property Office of P.R. China in connection with Patent Application No. 200880019166.0, dated Jul. 22, 2011, 16 pages.
English Translation of Decision of Rejection, issued by the State Intellectual Property Office of P.R. China in connection with Patent Application No. 200880104982.1, dated Sep. 23, 2011, 10 pages.
Extended European Search Report, issued by the European Patent Office in connection with European Application No. 11006934.1-2221, dated Oct. 25, 2011, 5 pages.
English Translation of First Office Action, issued by the State Intellectual Property Office of P.R. China in connection with Patent Application No. 20080017883.X, dated Nov. 30, 2011, 16 pages.
English Translation of Office Action, issued by the Israel Patent Office in connection with Patent Application No. 203176, dated Feb. 21, 2012, 2 pages.
English Translation of Office Action, issued by the Israel Patent Office in connection with Patent Application No. 203177, dated Mar. 1, 2012, 2 pages.
English Translation of Second Office Action, issued by the State Intellectual Property Office of P.R. China in connection with Patent Application No. 200880101500.7, dated Apr. 5, 2012, 5 pages.
English Translation of Second Office Action, issued by the State Intellectual Property Office of P.R. China in connection with Patent Application No. 200880019166.0, dated Jun. 5, 2012, 8 pages.
English Translation of Second Office Action, issued by the State Intellectual Property Office of P.R. China in connection with Patent Application No. 200880104982.1, dated Jun. 29, 2012, 5 pages.
English Translation of Second Office Action, issued by the State Intellectual Property Office of P.R. China in connection with Patent Application No. 200880017883.X, dated Aug. 10, 2012, 9 pages.
English Translation of Office Action, issued by the Israel Patent Office in connection with Patent Application No. 203176, dated Sep. 27, 2012, 1 page.
English Translation of Office Action, issued by the Israel Patent Office in connection with Patent Application No. 203177, dated Sep. 27, 2012, 1 page.
English Translation of Office Action, issued by the Japanese Patent Office in connection with Patent Application No. 2010-506646, dated Oct. 23, 2012, 3 pages.
English Translation of Third Office Action, issued by the State Intellectual Property Office of P.R. China in connection with Patent Application No. 200880101500.7, dated Nov. 21, 2012, 5 pages.
English Translation of Office Action, issued by the Israeli Patent Office in connection with Patent Application No. 201187, dated Nov. 27, 2012, 2 pages.
Extended European Search Report, issued by the European Patent Office in connection with European Application No. 08796890.5-2319/2170161, dated Dec. 7, 2012, 9 pages.
Notification to Grant Patent Right for Invention, issued by the State Intellectual Property Office of P.R. China in connection with Patent Application No. 200880104982.1, dated Jan. 14, 2013, 4 pages (includes English translation).
Extended European Search Report, issued by the European Patent Office in connection with European Application No. 08770372.4-1265/2152155, dated Feb. 6, 2013, 7 pages.
English Translation of Third Office Action, issued by the State Intellectual Property Office of P.R. China in connection with Patent Application No. 200880017883.X, dated Mar. 18, 2013, 8 pages.
English translation of Notification to Grant Patent Right for Invention, issued by the State Intellectual Property Office of P.R. China in connection with Patent Application No. 200880101500.7, dated Apr. 3, 2013, 2 pages.
Aaker et al., "Warmth in Advertising: Measurement, Impact, and Sequence Effects," Journal of Consumer Research, vol. 12, No. 4, pp. 365-381, (Mar. 1986), 18 pages.

(56) References Cited

OTHER PUBLICATIONS

Allen et al., "A Method for Removing Imaging Artifact from Continuous EEG Recorded during Functional MRI," Neuroimage, vol. 12, 230-239, (Aug. 2000), 12 pages.

Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.

Ambler et al., "Ads on the Brain: A Neuro-Imaging Comparison of Cognitive and Affective Advertising Stimuli," London Business School, Centre for Marketing Working Paper, No. 00-902, (Mar. 2000), 23 pages.

Bagozzi et al., "The Role of Emotions in Marketing," Journal of the Academy of Marketing Science, vol. 27, No. 2, pp. 184-206, Academy of Marketing Science (1999), 23 pages.

Barcelo, et al., "Prefrontal modulation of visual processing in humans," Nature Neuroscience, vol. 3, No. 4, Nature America, http//neurosci.nature.com, (Apr. 2000), 5 pages.

Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.

Belch et al., "Psychophysiological and cognitive Responses to Sex in Advertising," Advances in Consumer Research, vol. 9, pp. 424-427, (1982), 6 pages.

Bimler et al., "Categorical perception of facial expressions of emotion: Evidence from multidimensional scaling," Cognition and Emotion, vol. 15(5), pp. 633-658 (Sep. 2001), 26 pages.

Blakeslee, "If You Have a 'Buy Button' in Your Brain, What Pushes It?" The New York Times, www.nytimes.com, (Oct. 19, 2004), 3 pages.

Braeutigam, "Neuroeconomics—From neural systems to economic behavior," Brain Research Bulletin, vol. 67, pp. 355-360, Elsevier, (2005), 6 pages.

Buschman, et al., "Top-Down versus Bottom-Up Control of Attention in the Prefrontal and posterior Parietal Cortices," Science, vol. 315, www.sciencemag.org/cgi/content/full/315/5820/1860, American Association for the Advancement of Science, (2007), 4 pages.

Canolty, et al., "High Gamma Power Is Phase-Locked to Theta Oscillations in Human Neocortex," Science, vol. 313, www.sciencemag.org, (Sep. 15, 2006), 3 pages.

Clemons, "Resonance Marketing in the Age of the Truly Informed Consumer: Creating Profits through Differentiation and Delight," Wharton Information Strategy & Economics Blog 2, available at http://opim.wharton.upenn.edu/~clemons/blogs/resonanceblog.pdf, (Mar. 28, 2007), 8 pages.

Clifford, "Billboards That Look Back," The New York Times, NYTimes.com, available at http://www.nytimes.com/2008/05/31/business/media/31billboard.html, (May 31, 2008), 4 pages.

Crawford et al., "Self-generated happy and sad emotions in low and highly hypnotizable persons during waking and hypnosis: laterality and regional EEG activity differences," International Journal of Psychophysiology, vol. 24, pp. 239-266, (Dec. 1996), 28 pages.

Davidson, et al., "The functional neuroanatomy of emotion and affective style," Trends in Cognitive Sciences, vol. 3, No. 1, (Jan. 1999), 11 pages.

De Gelder et al., "Categorical Perception of Facial Expressions: Categories and their Internal Structure," Cognition and Emotion, vol. 11(1), pp. 1-23 (1997), 23 pages.

D'Esposito, "From cognitive to neural models of working memory," Phil. Trans. R. Soc. B, doi: 10.1098/rstb.2007.2086, (Mar. 30, 2007), 12 pages.

Desmet, "Measuring Emotions: Development and Application of an Instrument to Measure Emotional Responses to Products," to be published in Funology: From Usability to Enjoyment, pp. 1-13, Kluwer Academic Publishers, (Blythe et al., eds., 2004), 13 pages.

Dien, et al., "Application of Repeated Measures ANOVA to High-Density ERP Datasets: A Review and Tutorial," in Event-Related Potentials: A Methods Handbook pp. 57-82, (Todd C. Handy, ed., 2005), 14 pages.

Edgar, et al., "Digital Filters in ERP Research," in Event-Related Potentials: A Methods Handbook pp. 85-113, (Todd C. Handy, ed., 2005), 15 pages.

EEG Protocols, "Protocols for EEG Recording," retrieved from the Internet on Aug. 23, 2011, http://www.q-metrx.com/EEGrecordingProtocols.pdf, (Nov. 13, 2007), 3 pages.

Engel et al., "Dynamic Predictions: Oscillations and Synchrony in Top-down Processing," Nature Reviews: Neuroscience, vol. 2, pp. 704-716, Macmillian Magazines Ltd., (Oct. 2001), 13 pages.

Filler, "MR Neurography and Diffusion Tensor Imaging: Origins, History & Clinical Impact of the first 50,000 Cases With an Assessment of Efficacy and Utility in a Prospective 5,000 Patient Study Group," Institute for Nerve Medicine, (Nov. 7, 2008), 56 pages.

Friedman, et al., "Event-Related Potential (ERP) Studies of Memory Encoding and Retrieval: A Selective Review," Microscopy Research and Technique 51:6-22, Wiley-Liss, Inc. (2000), 23 pages.

Fries, "A mechanism for cognitive dynamics: neuronal communication through neuronal coherence," Trends in Cognitive Sciences, vol. 9, No. 10, pp. 474-480, Elsevier B.V. www.sciencedirect.com, (Oct. 2005), 7 pages.

Gaillard, "Problems and Paradigms in ERP Research," Biological Psychology, Elsevier Science Publisher B.V. (1988), 10 pages.

Gargiulo et al., "A Mobile EEG System With Dry Electrodes," (Nov. 2008), 4 pages.

Gazzaley et al., "Top-down Enhancement and Suppression of Magnitude and Speed of Neural Activity," Journal of Cognitive Neuroscience, vol. 17, No. 3, pp. 507-517, Massachusetts Institute of Technology, (2005), 11 pages.

Griss et al., "Characterization of micromachined spiked biopotential electrodes", Biomedical Engineering, IEEE Transactions (Jun. 2002), 8 pages.

Haq, "This Is Your Brain on Advertising," BusinessWeek, Market Research, (Oct. 8, 2007), 4 pages.

Hartikainen et al., Manuscript Draft of "Emotionally arousing stimuli compete with attention to left hemispace," NeuroReport, (Sep. 8, 2007), 26 pages.

Hazlett, et al., "Emotional Response to Television Commercials: Facial EMG vs. Self-Report," Journal of Advertising Research, (Apr. 1999), 17 pages.

Herrmann, et al., "Mechanisms of human attention: event-related potentials and oscillations," Neuroscience and Biobehavioral Reviews, pp. 465-476, Elsevier Science Ltd., www.elsvevier.com/locate/neubiorev, (2001), 12 pages.

Hopf, et al., "Neural Sources of Focused Attention in Visual Search," Cerebral Cortex, 10:1233-1241, Oxford University Press, (Dec. 2000), 9 pages.

Jung et al., "Analysis and Visualization of Single-Trial Event-Related Potentials," Human Brain Mapping vol. 14, 166-185 (2001), 20 pages.

Kay et al., "Identifying natural images from human brain activity," Nature, vol. 452, pp. 352-356, Nature Publishing Group, (Mar. 20, 2008), 5 pages.

Kishiyama, et al., "Socioeconomic Disparities Affect Prefrontal Function in Children," Journal of Cognitive Neuroscience pp. 1106-1115, Massachusetts Institute of Technology, (2008), 10 pages.

Klimesch, "EEG alpha and theta oscillations reflect cognitive and memory performance a review and analysis," Brain Research Reviews, vol. 29, 169-195, (1999), 27 pages.

Knight, "Contribution of human hippocampal region to novelty detection," Nature, vol. 383, www.nature.com, (Sep. 19, 1996), 4 pages.

Knight, "Consciousness Unchained: Ethical Issues and the Vegetative and minimally Conscious State," The American Journal of Bioethics, 8:9, 1-2, http://dx.doi.org/10.1080/15265160802414524, (Sep. 1, 2008), 3 pages.

Knight, et al., "Prefrontal cortex regulates inhibition and excitation in distributed neural networks," Acta Psychologica vol. 101, pp. 159-178, Elsevier (1999), 20 pages.

Knight, "Decreased Response to Novel Stimuli after Prefrontal Lesions in Man," Electroencephalography and Clinical Neurophysiology, vol. 59, pp. 9-20, Elsevier Scientific Publishers Ireland, Ltd., (1984), 12 pages.

(56) References Cited

OTHER PUBLICATIONS

Krakow et al., "Methodology: EEG-correlated fMRI," Functional Imaging in the Epilepsies, (Lippincott Williams & Wilkins, 2000), 17 pages.
Krugman, "Brain Wave Measures of Media Involvement," Journal of Advertising Research vol. 11, 3-9 (Feb. 1971), 7 pages.
Lachaux et al., "Measuring Phase Synchrony in Brain Signals," Human Brain Mapping 8 (1999), 194-208, 15 pages.
Lee et al., "What is 'neuromarketing'? A discussion and agenda for future research," International Journal of Psychophysiology, vol. 63, pp. 199-204, Elsevier (2006), 6 pages.
Lekakos, "Personalized Advertising Services Through Hybrid Recommendation Methods: The Case of Digital Interactive Television," Department of Informatics, Cyprus University, (2004), 11 pages.
Luck, et al., "The speed of visual attention in schizophrenia: Electrophysiological and behavioral evidence," Schizophrenia Research, pp. 174-195, Elsevier B.V. www.sciencedirect.com, (2006), 22 pages.
Lui et al., "Marketing Strategies in Virtual Worlds," The Data Base for Advances in Information Systems, vol. 38, No. 4, pp. 77-80, (Nov. 2007), 4 pages.
Makeig, et al., "Mining event-related brain dynamics," Trends in Cognitive Sciences, vol. 8, No. 5, (May 2004), www.sciencedirect.com, 7 pages.
Makeig, et al., "Dynamic Brain Sources of Visual Evoked Responses," Science, vol. 295, www.sciencemag.org, (Jan. 25, 2002), 5 pages.
The Mathworks, Inc., "Matlab Data Analysis: Version 7," p. 4-19 (2005), 3 pages.
Miltner, et al., "Coherence of gamma-band EEG activity as a basis for associative learning," Nature, vol. 397, www.nature.com, (Feb. 4, 1999), 3 pages.
Mosby's Dictionary of Medicine, Nursing, & Health Professions, 2009, Mosby, Inc., Definition of Alpha Wave, 1 page.
Mosby's Dictionary of Medicine, Nursing, & Health Professions, 2009, Mosby, Inc., Definition of Beta Wave, 1 page.
Neurofocus—Neuroscientific Analysis for Audience Engagement, accessed on Jan. 8, 2010 at http://web.archive.org/web/20080621114525/www.neurofocus.com/BrandImage.htm, (2008), 2 pages.
Newell et al., "Categorical perception of familiar objects," Cognition, vol. 85, Issue 2, pp. 113-143 (Sep. 2002), 31 pages.
Nielsen, "Neuroinformatics in Functional Neuroimaging," Informatics and Mathematical Modeling, Technical University of Denmark, (Aug. 30, 2002), 241 pages.
Oberman et al., "EEG evidence for mirror neuron activity during the observation of human and robot actions: Toward an analysis of the human qualities of interactive robots," Neurocomputing 70 (2007) 2194-2203, 10 pages.
Osborne, "Embedded Watermarking for image Verification in Telemedicine," Thesis submitted for the degree of Doctor of Philosophy, Electrical and Electronic Engineering, University of Adelaide (2005), 219 pages.
Padgett et al., "Categorical Perception in Facial Emotion Classification," In Proceedings of the 18th Annual Conference of the Cognitive Science Society, pp. 249-253 (1996), 5 pages.
Page et al., "Cognitive Neuroscience, Marketing and Research," Congress 2006—Foresight—The Predictive Power of Research Conference Papers, Esomar Publications, (Sep. 17, 2006), 25 pages.
Paller, et al., "Validating neural correlates of familiarity," Trends in Cognitive Sciences, vol. 11, No. 6, www.sciencedirect.com, (May 2, 2007), 8 pages.
Palva et al., "Phase Synchrony Among Neuronal Oscillations in the Human Cortex," Journal of Neuroscience 25 (2005), 3962-3972, 11 pages.
Picton, et al., "Guidelines for using human event-related potentials to study cognition: Recording standards and publication criteria," Psychophysiology, pp. 127-152, Society for Psychophysiological Research, (2000), 26 pages.
Rizzolatti et al., "The Mirror-Neuron System," Annu. Rev. Neurosci., vol. 27, pp. 169-192, (Mar. 5, 2004), 30 pages.
Ruchkin et al., "Modality-specific processing streams in verbal working memory: evidence from spatio-temporal patterns of brain activity," Cognitive Brain Research, vol. 6, pp. 95-113, Elsevier, (1997), 19 pages.
Rugg, et al., "Event-related potentials and recognition memory," Trends in Cognitive Sciences, vol. 11, No. 6, www.sciencedirect.com, (May 3, 2007), 7 pages.
Rugg, et al., "The ERP and cognitive psychology: conceptual issues," (Sep. 1996), 7 pages.
"User monitoring," Sapien Systems, available at http://web.archive.org/web/20030818043339/http:/www.sapiensystems.com/eyetracking.html, (Aug. 18, 2003), 1 page.
Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.
Spencer, "Averaging, Detection, and Classification of Single-Trial ERPs," in Event-Related Potentials: A Methods Handbook, pp. 209-227, (Todd C. Handy, ed., 2005), 10 pages.
Arousal in Sport, in Encyclopedia of Applied Psychology, vol. 1, p. 159, retrieved from Google Books, (Spielberger, ed., Elsevier Academic Press, 2004), 1 page.
Srinivasan, "High-Resolution EEG: Theory and Practice," in Event-Related Potentials: A Methods Handbook, pp. 167-188, (Todd C. Handy, ed., 2005), 12 pages.
Sullivan et al., "A brain-machine interface using dry-contact, low-noise EEG sensors," In Proceedings of the 2008 IEEE International Symposium on Circuits and Systems, (May 18, 2008), 4 pages.
Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, (Mar. 2007), 5 pages.
Swick, et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.
Taheri, et al., "A dry electrode for EEG recording," Electroencephalography and clinical Neurophysiology, pp. 376-383, Elsevier Science Ireland Ltd. (1994), 8 pages.
Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.
Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.
Woldorf, "Distortion of ERP averages due to overlap from temporally adjacent ERPs: Analysis and correction," Psychophysiology, Society for Psychophysiological Research, Cambridge University Press (1993), 22 pages.
Woodman, et al., "Serial Deployment of Attention During Visual Search," Journal of Experimental Psychology: Human Perception and Performance, vol. 29, No. 1, pp. 121-138, American Physiological Association (2003), 18 pages.
Yamaguchi, et al., "Rapid-Prefrontal-Hippocampal Habituation to Novel Events," The Journal of Neuroscience, pp. 5356-5363, Society for Neuroscience, (Apr. 29, 2004), 8 pages.
Yuval-Greenberg, et al., "Transient Induced Gamma-Bands Response in EEG as a Manifestation of Miniature Saccades," Neuron, vol. 58, pp. 429-441, Elsevier Inc. (May 8, 2008), 13 pages.
Ziegenfuss, "Neuromarketing: Advertising Ethical & Medical Technology," The Brownstone Journal, vol. XII, Boston University, pp. 69-73, (May 2005), 9 pages.
Zyga, "A Baseball Cap That Can Read Your Mind," PhysOrg.com, located at www.physorg.com/news130152277.html, (May 16, 2008), 11 pages.
Non-Final Office Action, issued by the United States Patent and Trademark Office in connection with U.S. Appl. No. 12/546,586, dated Apr. 25, 2013, 34 pages.

(56) References Cited

OTHER PUBLICATIONS

Non-Final Office Action, issued by the United States Patent and Trademark Office in connection with U.S. Appl. No. 13/444,149, dated May 2, 2013, 27 pages.
Notice of Allowance, issued by the United States Patent and Trademark Office in connection with U.S. Appl. No. 12/056,190, dated May 8, 2013, 4 pages.
Notice of Allowance, issued by the United States Patent and Trademark Office in connection with U.S. Appl. No. 12/056,211, dated May 8, 2013, 5 pages.
Notice of Allowance, issued by the United States Patent and Trademark Office in connection with U.S. Appl. No. 12/135,074, dated May 8, 2013, 5 pages.
Notice of Allowance, issued by the United States Patent and Trademark Office in connection with U.S. Appl. No. 12/199,596, dated May 8, 2013, 7 pages.
Notice of Allowance, issued by the United States Patent and Trademark Office in connection with U.S. Appl. No. 13/569,711, dated May 14, 2013, 6 pages.
Notice of Allowance, issued by the United States Patent and Trademark Office in connection with U.S. Appl. No. 12/182,874, dated May 17, 2013, 6 pages.
Final Office Action, issued by the United States Patent and Trademark Office in connection with U.S. Appl. No. 12/778,828, dated May 23, 2013, 25 pages.
Office Communication to Applicant, issued by the United States Patent and Trademark Office in connection with U.S. Appl. No. 12/234,388, dated May 24, 2013, 2 pages.
Non-Final Office Action, issued by the United States Patent and Trademark Office in connection with U.S. Appl. No. 12/884,034, dated May 28, 2013, 12 pages.
Notice of Allowance, issued by the United States Patent and Trademark Office in connection with U.S. Appl. No. 12/135,074, dated May 31, 2013, 5 pages.
Notice of Allowance, issued by the United States Patent and Trademark Office in connection with U.S. Appl. No. 12/056,211, dated Jun. 3, 2013, 5 pages.
Notice of Allowance, issued by the United States Patent and Trademark Office in connection with U.S. Appl. No. 12/199,596, dated Jun. 3, 2013, 5 pages.
Notice of Allowance, issued by the United States Patent and Trademark Office in connection with U.S. Appl. No. 12/199,596, dated Jun. 11, 2013, 7 pages.
Notice of Allowance, issued by the United States Patent and Trademark Office in connection with U.S. Appl. No. 12/545,455, dated Jun. 11, 2013, 9 pages.
Notice of Allowance, issued by the United States Patent and Trademark Office in connection with U.S. Appl. No. 12/056,190, dated Jun. 13, 2013, 5 pages.
Office Communication to Applicant, issued by the United States Patent and Trademark Office in connection with U.S. Appl. No. 12/234,388, dated Jun. 13, 2013, 2 pages.
Notice of Allowance, issued by the United States Patent and Trademark Office in connection with U.S. Appl. No. 12/135,074, dated Jun. 21, 2013, 5 pages.
Non-Final Office Action, issued by the United States Patent and Trademark Office in connection with U.S. Appl. No. 13/105,774, dated Jun. 26, 2013, 10 pages.
English Translation of Office Action, issued by the Israeli Patent Office in connection with Patent Application No. 203176, dated Apr. 23, 2013, 1 page.
English Translation of Notice Prior to Allowance, issued by the Israeli Patent Office in connection with Patent Application No. 203176, dated Jun. 30, 2013, 1 page.
Enghoff, Sigurd, Thesis: "Moving ICA and Time-Frequency Analysis in Event-Related EEG Studies of Selective Attention," Technical University of Denmark, (Dec. 1999), 54 pages.
Zhang, P., "Will You Use Animation on Your Web Pages?" Doing Business on the Internet: Opportunities and Pitfalls, C. Romm and F. Sudweeks (eds.), Spring-Verlag (1999), 17 pages.
Notice of Allowance, issued by the United States Patent and Trademark Office in connection with U.S. Appl. No. 12/182,874, dated Jul. 29, 2013, 6 pages.
Office Action, issued by the United States Patent and Trademark Office in connection with U.S. Appl. No. 12/546,586, dated Sep. 12, 2013, 13 pages.
Notice of Allowance, issued by the United States Patent and Trademark Office in connection with U.S. Appl. No. 12/199,596, dated Sep. 13, 2013, 7 pages.
Office Action, issued by the United States Patent and Trademark Office in connection with U.S. Appl. No. 12/113,870, dated Sep. 17, 2013, 11 pages.
Notice of Allowance, issued by the United States Patent and Trademark Office in connection with U.S. Appl. No. 12/778,828, dated Oct. 8, 2013, 11 pages.
English Translation of Office Action, issued by the Japanese Patent Office in connection with Patent Application No. 2010-523112, on Jul. 30, 2013, 2 pages.
Decision to Grant Patent, issued by the Japanese Patent Office in connection with Patent Application No. 2010-506646, dated Aug. 6, 2013, 4 pages (includes English translation).
English Translation of Decision on Rejection, issued by the Chinese Patent Office in connection with Patent Application No. 200880017883.X, dated Aug. 5, 2013, 13 pages.
Final Office Action, issued by the United States Patent and Trademark Office in connection with U.S. Appl. No. 12/884,034, dated Oct. 23, 2013, 17 pages.
Notice of Allowance, issued by the United States Patent and Trademark Office in connection with U.S. Appl. No. 12/199,596, dated Nov. 6, 2013, 7 pages.
Final Office Action, issued by the United States Patent and Trademark Office in connection with U.S. Appl. No. 13/444,149, dated Nov. 19, 2013, 11 pages.
Non-Final Office Action, issued by the United States Patent and Trademark Office in connection with U.S. Appl. No. 12/122,253, dated Dec. 3, 2013, 16 pages.
Notice of Allowance, issued by the United States Patent and Trademark Office in connection with U.S. Appl. No. 12/199,596, dated Dec. 23, 2013, 7 pages.
Final Office Action, issued by the United States Patent and Trademark Office in connection with U.S. Appl. No. 13/105,774, dated Jan. 16, 2014, 11 pages.
English Translation of Office Action, issued by the Japanese Patent Office in connection with Patent Application No. 2010-520159, dated Oct. 1, 2013, 2 pages.
Extended European Search Report, issued by the European Patent Office in connection with European Application No. 08798799.6-1657/2180825, dated Nov. 4, 2013, 9 pages.
Coan et al., "Voluntary Facial Expression and Hemispheric Asymmetry Over the Frontal Cortex," Psycophysiology (Nov. 2001), 912-924, 14 pages.
Duchowski, "A Breadth-First Survey of Eye-tracking Applications," Beahavior Research Methods, Instruments, and Computers (Nov. 2002), 455-470, 16 pages.
Heo et al., "Wait! Why is it Not Moving? Attractive and Distractive Ocular Responses to Web Ads," Paper presented to AEJMC, (Aug. 2001) Washington, DC, available at http://www.psu.edu/dept/medialab/researchpage/newabstracts/wait.html, 3 pages.
Rothschild et al., "Predicting Memory for Components of TV Commercials from EEG," Journal of Consumer Research (Mar. 1990), p. 472-478, 8 pages.
Beaver, John D., et al., "Individual Differences in Reward Drive Predict Neural Responses to Images of Food", J. of Neuroscience, (May 10, 2006), 5160-5166, 7 pages.
Tapert, Susan F., et al., "Neural Response to Alcohol Stimuli in Adolescents With Alcohol Use Disorder", Arch Gen Psychiatry (Jul. 2003), 727-735, 9 pages.
Shandlen, Michael N. et al., "A Computational Analysis of the Relationship between Neuronal and Behavioral Responses to Visual Motion", The Journal of Neuroscience, (Feb. 15, 1996) 1486-1510, 25 pages.

(56) References Cited

OTHER PUBLICATIONS

Office Action, issued by the United States Patent and Trademark Office in connection with U.S. Appl. No. 13/730,541, dated Jan. 30, 2014, 12 pages.
Office Action, issued by the United States Patent and Trademark Office in connection with U.S. Appl. No. 13/730,550, dated Jan. 31, 2014, 5 pages.
Office Action, issued by the United States Patent and Trademark Office in connection with U.S. Appl. No. 13/965,805, dated Feb. 3, 2014, 15 pages.
Notice of Allowance, issued by the United States Patent and Trademark Office in connection with U.S. Appl. No. 13/444,149, dated Feb. 3, 2014, 5 pages.
Office Action, issued by the United States Patent and Trademark Office in connection with U.S. Appl. No. 12/113,870, dated Feb. 4, 2014, 12 pages.
Office Action, issued by the United States Patent and Trademark Office in connection with U.S. Appl. No. 12/546,586, dated Feb. 6, 2014, 17 pages.
Office Action, issued by the United States Patent and Trademark Office in connection with U.S. Appl. No. 13/730,564, dated Feb. 10, 2014, 14 pages.
Office Action, issued by the United States Patent and Trademark Office in connection with U.S. Appl. No. 12/884,034, dated Feb. 10, 2014, 18 pages.
Mehta, A. et al., "Reconsidering Recall and Emotion in Advertising", Journal of Advertising Research, (Mar. 2006), 49-56, 9 pages.
Cheung, Kwok-Wai, et al., "Mining Customer Product Ratings for Personalized Marketing," Decision Support Systems 35 (2003) 231-243, 13 pages.
Notice of Allowance, issued by the United States Patent and Trademark Office in connection with U.S. Appl. No. 13/730,550, dated May 27, 2014, 8 pages.
Office Action, issued by the United States Patent and Trademark Office in connection with U.S. Appl. No. 12/608,660, dated Jun. 2, 2014, 13 pages.
Office Action, issued by the United States Patent and Trademark Office in connection with U.S. Appl. No. 12/122,253, dated Jun. 5, 2014, 25 pages.
Final Office Action, issued by the United States Patent and Trademark Office in connection with U.S. Appl. No. 12/113,870, dated Jul. 1, 2014, 16 pages.
Decision to Grant Patent, issued by the Japanese Patent Office in connection with Patent Application No. 2010-523112, dated Apr. 8, 2014, 4 pages (includes English translation).
Darrow, Chester, "Psychological and psychophysiological significance of the electroencephalogram," Psychological Review (May 1947) 157-168, 12 pages.
Stamm, John, "On the Relationship between Reaction Time to Light and Latency of Blocking the Alpha Rhythm," Electroencephalography and Clinical Neurophysiology (Feb. 1952), 61-68, 8 pages.
Mizuki, Yashushi, et al., "Periodic Appearance of the Theta Rhythm in the Frontal Midline Area During Performance of a Mental Task,:" Electroencephalography and Clinical Neurophysiology (Aug. 1980), 345-351, 7 pages.
Decision to Grant Patent, issued by the Korean Patent Office in connection with Patent Application No. 10-2009-7022551, dated Aug. 13, 2014, 3 pages (includes English translation).
Non-Final Office Action, issued by the United States Patent and Trademark Office in connection with U.S. Appl. No. 13/730,541, dated Jul. 23, 2014, 13 pages.
Non-Final Office Action, issued by the United States Patent and Trademark Office in connection with U.S. Appl. No. 13/965,805, dated Aug. 6, 2014, 18 pages.
Non-Final Office Action, issued by the United States Patent and Trademark Office in connection with U.S. Appl. No. 13/730,550, dated Aug. 14, 2014, 4 pages.
Non-Final Office Action, issued by the United States Patent and Trademark Office in connection with U.S. Appl. No. 13/730,564, dated Aug. 15, 2014, 15 pages.
Non-Final Office Action, issued by the United States Patent and Trademark Office in connection with U.S. Appl. No. 12/884,034, dated Aug. 21, 2014, 20 pages.
Non-Final Office Action, issued by the United States Patent and Trademark Office in connection with U.S. Appl. No. 12/608,685, dated Sep. 4, 2014, 16 pages.
Non-Final Office Action, issued by the United States Patent and Trademark Office in connection with U.S. Appl. No. 13/105,774, dated Sep. 18, 2014, 14 pages.
Final Office Action, issued by the United States Patent and Trademark Office in connection with U.S. Appl. No. 12/546,586, dated Sep. 29, 2014, 21 pages.
Ekman, P., Friesen, W., "Measuring Facial Movement," Environmental Psychology and Nonverbal Behavior, 1 (1) (Fall 1976), pp. 56-75, 20 pages.
Ekman, P., Friesen, W.V., *Facial Action Coding System: A Technique for Measurement of Facial Movement*, Consulting Psychologists Press, Palo Alto, Calif. (1978). (Book, copy not provided.).
Ekman, P., Friesen, W., *Unmasking the Face—A Guide to Recognizing Emotions from Facial Clues*, Prentice-Hall, Inc., Englewood Cliffs, N.J. (1979). (Book, copy not provided.).
Ekman, P., Friesen, W., Ancoli, S., "Facial Signs of Emotional Experience," J. Personality & Social Psychology, 39(6) (Dec. 1980), pp. 1125-1134, 10 pages.
Izard, C. E., *The Maximally Discriminative Facial Movement Coding System*, (Rev. ed.), Instructional Resources Center, University of Delaware, Newark, Del. (1983). (Book, copy not provided.).
Izard, C., Dougherty, L., Hembree, E., *A System for Identifying Affect Expressions by Holistic Judgments (AFFEX)*, Instructional Resources Center, University of Delaware, Newark, Del. (1983). (Book, copy not provided.).
Jia, X., Nixon, M.S., Extending the Feature Set for Automatic Face Recognition, International Conference on Image Processing and Its Applications (Apr. 7-9, 1992), 6 pages.
Lisetti, C., Nasoz, F., "Using Noninvasive Wearable Computers to Recognize Human Emotions from Physiological Signals," EURASIP J. Applied Signal Processing, Sep. 11, 2004, pp. 1672-1687, 16 pages.
Non-Final Office Action, issued by the United States Patent and Trademark Office in connection with U.S. Appl. No. 14/177,698, dated Oct. 24, 2014, 13 pages.
Advisory Action, issued by the United States Patent and Trademark Office in connection with U.S. Appl. No. 12/546,586, dated Dec. 22, 2014, 3 pages.
English Translation of Notification of Provisional Rejection, issued by the Korean Patent Office in connection with Patent Application No. 10-2010-7001406, dated Oct. 21, 2014, 1 page.
Non-Final Office Action, issued by the United States Patent and Trademark Office in connection with U.S. Appl. No. 13/730,550, dated Feb. 20, 2015, 12 pages.
Final Office Action, issued by the United States Patent and Trademark Office in connection with U.S. Appl. No. 12/608,660, dated Feb. 20, 2015, 52 pages.
Final Office Action, issued by the United States Patent and Trademark Office in connection with U.S. Appl. No. 13/965,805, dated Mar. 6, 2015, 18 pages.
Non-Final Office Action, issued by the United States Patent and Trademark Office in connection with U.S. Appl. No. 13/708,344, dated Apr. 9, 2015, 12 pages.
Final Office Action, issued by the United States Patent and Trademark Office in connection with U.S. Appl. No. 14/177,698, dated Apr. 24, 2015, 13 pages.
Final Office Action, issued by the United States Patent and Trademark Office in connection with U.S. Appl. No. 12/608,685, dated May 5, 2015, 7 pages.
Final Office Action, issued by the United States Patent and Trademark Office in connection with U.S. Appl. No. 13/105,774, dated May 14, 2015, 15 pages.
Final Office Action, issued by the United States Patent and Trademark Office in connection with U.S. Appl. No. 12/884,034, dated May 14, 2015, 22 pages.

(56) References Cited

OTHER PUBLICATIONS

Final Office Action, issued by the United States Patent and Trademark Office in connection with U.S. Appl. No. 13/730,564, dated May 22, 2015, 6 pages.
Final Office Action, issued by the United States Patent and Trademark Office in connection with U.S. Appl. No. 13/249,512, dated Jun. 30, 2015, 36 pages.
Notification of Provisional Rejection, issued by the Korean Patent Office in connection with Patent Application No. 10-2010-7001406, dated Jun. 24, 2015, 9 pages (includes partial translation).
McClure, Samuel, et al., "Neural Correlates of Behavioral Preference for Culturally Familiar Drinks," Neuron (Oct. 14, 2004), 379-387, 9 pages.
English Translation of Office Action, issued by the Israel Patent Office in connection with Patent Application No. 201187, dated Jun. 22, 2015, 4 pages.
Examiner's Answer, issued by the United States Patent and Trademark Office in connection with U.S. Appl. No. 12/113,870, dated Jul. 30, 2015, 14 pages.
Examiner's Answer, issued by the United States Patent and Trademark Office in connection with U.S. Appl. No. 12/122,253, dated Aug. 4, 2015, 29 pages.
Non-Final Office Action, issued by the United States Patent and Trademark Office in connection with U.S. Appl. No. 14/177,698, dated Aug. 19, 2015, 12 pages.
Examiner's Answer, issued by the United States Patent and Trademark Office in connection with U.S. Appl. No. 12/546,586, dated Sep. 11, 2015, 7 pages.
Final Office Action, issued by the United States Patent and Trademark Office in connection with U.S. Appl. No. 13/730,550, dated Sep. 2, 2015, 6 pages.
Non-Final Office Action, issued by the United States Patent and Trademark Office in connection with U.S. Appl. No. 12/410,380, dated Sep. 10, 2015, 15 pages.
Advisory Action, issued by the United States Patent and Trademark Office in connection with U.S. Appl. No. 12/884,034, dated Sep. 16, 2015, 3 pages.
Non-Final Office Action, issued by the United States Patent and Trademark Office in connection with U.S. Appl. No. 13/705,525, dated Sep. 30, 2015, 12 pages.
Non-Final Office Action, issued by the United States Patent and Trademark Office in connection with U.S. Appl. No. 13/965,805, dated Sep. 30, 2015, 6 pages.
Final Office Action, issued by the United States Patent and Trademark Office in connection with U.S. Appl. No. 13/708,344, dated Nov. 20, 2015, 28 pages.
Translation of Reexamination Decision, issued by the Chinese Patent Office in connection with Patent Application No. 200880017883.X, dated Nov. 13, 2015, 1 page.
Non-Final Office Action, issued by the United States Patent and Trademark Office in connection with U.S. Appl. No. 12/608,685, dated Dec. 17, 2015, 14 pages.
Examiner's Answer, issued by the United States Patent and Trademark Office in connection with U.S. Appl. No. 13/730,541, dated Dec. 18, 2015, 7 pages.
Notice of Allowance, issued by the United States Patent and Trademark Office in connection with U.S. Appl. No. 14/177,698, dated Jan. 14, 2016, 36 pages.
Non-Final Office Action, issued by the United States Patent and Trademark Office in connection with U.S. Appl. No. 12/608,660, dated Jan. 22, 2016, 38 pages.
Final Office Action, issued by the United States Patent and Trademark Office in connection with U.S. Appl. No. 13/708,525, dated Feb. 3, 2016, 22 pages.
Non-Final Office Action, issued by the United States Patent and Trademark Office in connection with U.S. Appl. No. 12/410,372, dated Feb. 23, 2016, 24 pages.
English Translation of Notification of Provisional Rejection, issued by the Korean Patent Office in connection with Patent Application No. 10-2010-7001406, dated Jan. 26, 2016, 1 page.
English Translation of Notification to Grant Patent Right for Invention, issued by the State Intellectual Property Office of P.R. China in connection with Patent Application No. 200880017883.X, dated Feb. 3, 2016, 2 pages.
Final Office Action, issued by the United States Patent and Trademark Office in connection with U.S. Appl. No. 12/410,380, dated Mar. 22, 2016, 27 pages.
Final Office Action, issued by the United States Patent and Trademark Office in connection with U.S. Appl. No. 12/608,685, dated Mar. 30, 2016, 23 pages.
Advisory Action, issued by the United States Patent and Trademark Office in connection with U.S. Appl. No. 13/708,525, dated Apr. 6, 2016, 3 pages.
Examiner's Answer, issued by the United States Patent and Trademark Office in connection with U.S. Appl. No. 13/730,564, dated Apr. 8, 2016, 7 pages.
Final Office Action, issued by the United States Patent and Trademark Office in connection with U.S. Appl. No. 13/965,805, dated Apr. 21, 2016, 33 pages.
Final Office Action, issued by the United States Patent and Trademark Office in connection with U.S. Appl. No. 12/234,372, dated May 12, 2016, 61 pages.
Non-Final Office Action, issued by the United States Patent and Trademark Office in connection with U.S. Appl. No. 12/884,034, dated May 20, 2016, 69 pages.
Non-Final Office Action, issued by the United States Patent and Trademark Office in connection with U.S. Appl. No. 13/945,357, dated May 20, 2016, 22 pages.
M. Corbetta et al., "Control of Goal-Directed and Stimulus-Driven Attention in the Brain," Nature Reviews Neuroscience, vol. 3, pp. 201-215 (Mar. 2002), 15 pages.
Becker, "A Study of Web Usability for Older Adults Seeking Online Health Resources," ACM Transactions on Computer-Human Interaction, vol. 11, No. 4, pp. 387-406 (Dec. 2004), 20 pages.
Non-Final Office Action, issued by the United States Patent and Trademark Office in connection with U.S. Appl. No. 12/410,380, dated Jun. 17, 2016, 20 pages.
Notice of Allowance, issued by the United States Patent and Trademark Office in connection with U.S. Appl. No. 12/608,660, dated Jul. 29, 2016, 67 pages.
Examiner's Answer, issued by the United States Patent and Trademark Office in connection with U.S. Appl. No. 13/730,550, dated Jul. 27, 2016, 20 pages.
Advisory Action, issued by the United States Patent and Trademark Office in connection with U.S. Appl. No. 12/234,372, dated Aug. 8, 2016, 3 pages.
Non-Final Office Action, issued by the United States Patent and Trademark Office in connection with U.S. Appl. No. 12/413,297, dated Aug. 16, 2016, 5 pages.
Final Office Action, issued by the United States Patent and Trademark Office in connection with U.S. Appl. No. 12/410,372, dated Aug. 25, 2016, 61 pages.
Notification of Provisional Rejection, issued by the Korean Patent Office in connection with Patent Application No. 10-2010-7001406, dated Jul. 27, 2016, 4 pages (includes partial translation).
Final Office Action, issued by the United States Patent and Trademark Office in connection with U.S. Appl. No. 13/945,357, dated Nov. 1, 2016, 22 pages.
Advisory Action, issued by the United States Patent and Trademark Office in connection with U.S. Appl. No. 12/410,372, dated Nov. 7, 2016, 3 pages.
Examiner's Answer, issued by the United States Patent and Trademark Office in connection with U.S. Appl. No. 12/234,372, dated Nov. 14, 2016, 18 pages.
Examiner's Answer, issued by the United States Patent and Trademark Office in connection with U.S. Appl. No. 12/608,685, dated Nov. 14, 2016, 10 pages.
Final Office Action, issued by the United States Patent and Trademark Office in connection with U.S. Appl. No. 12/884,034, dated Nov. 29, 2016, 27 pages.
European Patent Office, "Communication Pursuant to Article 94(3) EPC," in connection with European Application No. 08796890.5, dated Sep. 29, 2016, 4 pages.

(56) References Cited

OTHER PUBLICATIONS

Final Office Action, issued by the United States Patent and Trademark Office in connection with U.S. Appl. No. 12/410,380, dated Dec. 15, 2016, 31 pages.
Non-Final Office Action, issued by the United States Patent and Trademark Office in connection with U.S. Appl. No. 13/708,344, dated Jan. 26, 2017, 52 pages.
Examiner's Answer, issued by the United States Patent and Trademark Office in connection with U.S. Appl. No. 13/965,805, dated Jan. 31, 2017, 25 pages.
Final Office Action, issued by the United States Patent and Trademark Office in connection with U.S. Appl. No. 12/413,297, dated Feb. 9, 2017, 7 pages.
Advisory Action, issued by the United States Patent and Trademark Office in connection with U.S. Appl. No. 12/884,034, dated Mar. 2, 2017, 14 pages.
English Translation of Notice Prior to Allowance, issued by the Israeli Patent Office in connection with Patent Application No. 201187, dated Feb. 14, 2017, 1 page.
Decision on Appeal, issued by the United States Patent and Trademark Office in connection with U.S. Appl. No. 12/122,253, on Mar. 31, 2017, 37 pages.
Non-Final Office Action, issued by the United States Patent and Trademark Office in connection with U.S. Appl. No. 13/708,525, dated Apr. 27, 2017, 45 pages.
Examiner's Answer, issued by the United States Patent and Trademark Office in connection with U.S. Appl. No. 12/410,372, dated May 25, 2017, 9 pages.
Decision on Appeal, issued by the United States Patent and Trademark Office in connection with U.S. Appl. No. 12/546,586, on Jun. 5, 2017, 39 pages.
European Patent Office, "Communication Pursuant to Article 94(3) EPC," issued in connection with European Patent Application No. 08 744 383.4, dated Apr. 19, 2017, 6 pages.
Final Office Action, issued by the United States Patent and Trademark Office in connection with U.S. Appl. No. 13/708,344, dated Jun. 29, 2017, 38 pages.
Non-Final Office Action, issued by the United States Patent and Trademark Office in connection with U.S. Appl. No. 13/945,357, dated Jul. 6, 2017, 17 pages.
Decision on Appeal, issued by the United States Patent and Trademark Office in connection with U.S. Appl. No. 12/113,870, on Jul. 13, 2017, 12 pages.
Final Office Action, issued by the United States Patent and Trademark Office in connection with U.S. Appl. No. 13/708,525, dated Aug. 14, 2017, 38 pages.
Examiner's Answer, issued by the United States Patent and Trademark Office in connection with U.S. Appl. No. 12/410,380, dated Aug. 18, 2017, 2017, 11 pages.
Non-Final Office Action, issued by the United States Patent and Trademark Office in connection with U.S. Appl. No. 12/546,586, dated Sep. 19, 2017, 43 pages.
Notice of Allowance, issued by the United States Patent and Trademark Office in connection with U.S. Appl. No. 12/113,870, dated Sep. 26, 2017, 51 pages.
Summons to Attend Oral Proceedings Pursuant to Rule 115(1) EPC, issued by the European Patent Office in connection with European Patent Application No. 08796890.5, on Jul. 3, 2017, 3 pages.
English Translation of First Examination Report, issued by the Indian Patent Office in connection with Indian Patent Application No. 6145/CHENP/2009, dated Aug. 16, 2017, 6 pages.
Advisory Action, issued by the United States Patent and Trademark Office in connection with U.S. Appl. No. 13/708,344, dated Oct. 2, 2017, 5 pages.
Final Office Action, issued by the United States Patent and Trademark Office in connection with U.S. Appl. No. 13/945,357, dated Oct. 20, 2017, 16 pages.
Advisory Action, issued by the United States Patent and Trademark Office in connection with U.S. Appl. No. 13/708,525, dated Oct. 26, 2017, 4 pages.

Examiner's Answer, issued by the United States Patent and Trademark Office in connection with U.S. Appl. No. 12/413,297, dated Oct. 31, 2017, 2017, 68 pages.
Non-Final Office Action, issued by the United States Patent and Trademark Office in connection with U.S. Appl. No. 15/299,752, dated Nov. 3, 2017, 131 pages.
Non-Final Office Action, issued by the United States Patent and Trademark Office in connection with U.S. Appl. No. 12/884,034, dated Nov. 15, 2017, 49 pages.
Decision on Appeal, issued by the United States Patent and Trademark Office in connection with U.S. Appl. No. 13/730,541, on Dec. 6, 2017, 14 pages.
Non-Final Office Action, issued by the United States Patent and Trademark Office in connection with U.S. Appl. No. 12/546,586, dated Dec. 28, 2017, 23 pages.
Decision on Appeal, issued by the United States Patent and Trademark Office in connection with U.S. Appl. No. 12/608,685, on Jan. 29, 2018, 11 pages.
Ganel et al., "The Relationship Between fMRI Adapation and Repetition Priming," NeuroImage, Jul. 18, 2006, pp. 1434-1440, 9 pages.
Non-Final Office Action, issued by the United States Patent and Trademark Office in connection with U.S. Appl. No. 13/730,511, dated Jan. 30, 2014, 67 pages.
Non-Final Office Action, issued by the United States Patent and Trademark Office in connection with U.S. Appl. No. 13/730,511, dated Aug. 13, 2014, 8 pages.
Final Office Action, issued by the United States Patent and Trademark Office in connection with U.S. Appl. No. 13/730,511, dated May 6, 2015, 15 pages.
Examiner's Answer, issued by the United States Patent and Trademark Office in connection with U.S. Appl. No. 13/730,511, dated Feb. 18, 2016, 5 pages.
Decision on Appeal, issued by the United States Patent and Trademark Office in connection with U.S. Appl. No. 13/730,511, on Mar. 1, 2018, 14 pages.
Notice of Allowance, issued by the United States Patent and Trademark Office in connection with U.S. Appl. No. 13/730,511, dated May 29, 2014, 8 pages.
Final Office Action, issued by the United States Patent and Trademark Office in connection with U.S. Appl. No. 13/730,541, dated Feb. 12, 2015, 6 pages.
Decision on Appeal, issued by the United States Patent and Trademark Office in connection with U.S. Appl. No. 12/410,380, on Mar. 30, 2015, 6 pages.
Decision on Appeal, issued by the United States Patent and Trademark Office in connection with U.S. Appl. No. 12/234,372, on Jun. 15, 2015, 5 pages.
Non-Final Office Action, issued by the United States Patent and Trademark Office in connection with U.S. Appl. No. 12/234,372, dated Sep. 23, 2015, 16 pages.
Decision on Appeal, issued by the United States Patent and Trademark Office in connection with U.S. Appl. No. 12/410,372, on Sep. 22, 2015, 6 pages.
Decision on Appeal, issued by the United States Patent and Trademark Office in connection with U.S. Appl. No. 12/413,297, on Nov. 27, 2015, 5 pages.
Decision on Appeal, issued by the United States Patent and Trademark Office in connection with U.S. Appl. No. 13/730,564, on Feb. 2, 2018, 10 pages.
Decision on Appeal, issued by the United States Patent and Trademark Office in connection with U.S. Appl. No. 13/730,550, on Mar. 27, 2018, 13 pages.
Notice of Allowance, issued by the United States Patent and Trademark Office in connection with U.S. Appl. No. 15/299,752, dated Apr. 17, 2017, 21 pages.
Non-Final Office Action, issued by the United States Patent and Trademark Office in connection with U.S. Appl. No. 12/884,034, dated May 3, 2018, 46 pages.
Non-Final Office Action, issued by the United States Patent and Trademark Office in connection with U.S. Appl. No. 13/708,525, dated May 18, 2018, 31 pages.

(56) References Cited

OTHER PUBLICATIONS

Notice of Allowance, issued by the United States Patent and Trademark Office in connection with U.S. Appl. No. 13/730,541, dated Jun. 27, 2018, 62 pages.
Notice of Allowance, issued by the United States Patent and Trademark Office in connection with U.S. Appl. No. 13/730,564, dated Jun. 27, 2018, 69 pages.
Final Office Action, issued by the United States Patent and Trademark Office in connection with U.S. Appl. No. 12/546,586, dated Jun. 28, 2018, 22 pages.
Decision on Request for Rehearing, issued by the United States Patent and Trademark Office in connection with U.S. Appl. No. 12/608,685, on Aug. 10, 2018, 8 pages.
Extended European Search Report, issued by the European Patent Office in connection with European Application No. 08747389.8-1952, dated Sep. 25, 2015, 6 pages.
Communication Under Rule 71(3) EPC, issued by the European Patent Office in connection with European Application No. 08796890.5, dated Mar. 16, 2018, 43 pages.
English Translation of First Examination Report, issued by the Indian Patent Office in connection with Indian Patent Application No. 4441/KOLNP/2009, dated May 21, 2018, 5 pages.
Knutson et al., "Neural Predictors of Purchases," Neuron vol. 53 (Jan. 4, 2007), pp. 147-156, 10 pages.
Schaefer et al., "Neural Correlates of Culturally Familiar Brands of Car Manufacturers," NeuroImage, vol. 31 (2006), pp. 861-865, 5 pages.
Aharon et al., "Beautiful Faces Have Variable Reward Value: fMRI and Behavorial Evidence," Neuron, vol. 32 (2001), pp. 537-551, 15 pages.
Kamba et al., "The Krakatoa Chronicle—An Interactive, Personalized, Newspaper on the Web," available at: http://www.w3.org/Conferences/WWW4/Papers/93/ (last accessed Nov. 2, 2015), 15 pages.
Ehrenberg et al., "Understanding Brand Performance Measures: Using Dirichlet Benchmarks," 2004, Journal of Business Research, vol. 57, pp. 1307-1325, 19 pages.
Leeflang et al., "Building Models for Marketing Decisions," 2000, Springer Science + Business Media, pp. 192-235, 482-521, 86 pages.
Bhattacharya, "Is your brand's loyalty too much, too little, or just right?: Explaining deviations in loyalty from the Dirichlet norm," 1997, International Journal of Research in Marketing, vol. 14, pp. 421-435, 15 pages.
Nikolaeva et al., "The Moderating Role of Consumer and Product Characteristics on the Value of Customized On-Line Recommendations," 2006, International Journal of Electronic Commerce, vol. 11, No. 2, pp. 101-123, 24 pages.
Ehrenberg, "New Brands and the Existing Market," 1991, International Journal of Market Research, vol. 33, No. 4, 10 pages.
Foxall, "The Substitutability of Brands," 1999, Managerial and Decision Economics, vol. 20, pp. 241-257, 17 pages.
Pammer et al., "Forecasting the Penetration of a New Product—A Bayesian Approach," 2000, Journal of Business and Economic Statistics, vol. 18, No. 4, pp. 428-435, 8 pages.
Rungie et al., "Calculation of Theoretical Brand Performance Measures from the Parameters of the Dirichlet Model," 2004, Marketing Bulletin, Massey University, 15, Technical Note 2, pp. 1-19, 20 pages.
Uncles et al., "Patterns of Buyer Behavior: Regularities, Models, and Extensions," 1995, Marketing Science, vol. 14, No. 3, pp. G71-G78, 9 pages.
Boltz, "The cognitive processing of film and musical soundtracks," Haverford College, Haverford, Pennsylvania, 2004, 32 (7), 1194-1205, 12 pages.
Christie et al., "Autonomic specificity of discrete emotion and dimensions of affective space: a multivariate approach," International Journal of Psychophysiology, 51 (2004) 143-153, 11 pages.
Coombes et al., "Emotion and movement: Activation of defensive circuitry alters the magnitude of a sustained muscle contraction," University of Florida, USA, Neuroscience Letters 396 (2006) 192-196, 5 pages.
Cryer et al. "Pull the Plug on Stress," Harvard Business Review, Jul. 2003, 8 pages.
Demaree et al., "Predicting facial valence to negative stimuli from resting RSA: Not a function of active emotion regulation," Cognition and Emotion vol. 20, Issue 2, 2006, pp. 161-176, published on Sep. 9, 2010, http://www.tandfonline.com/doi/abs/10.1080/02699930500260427, 6 pages. (Abstract provided.).
Elkman et al., "Autonomic Nervous System Activity Distinguishes among Emotions," Science, New Series, vol. 221, No. 4616. (Sep. 16, 1983), pp. 1208-1210, http://links.jstor.org/sici?sici=0036-8075%2819830916%293%3A221%3A4616%3C1208%3AANSADA%3E2.0.CO%3B2-H, 5 pages.
Elton, "Measuring emotion at the symphony," The Boston Globe, Apr. 5, 2006, http://www.psych.mcgill.ca/labs/levitin/media/measuring_emotion_boston.html, 3 pages.
Goldberg, "Getting wired could help predict emotions," The Boston Globe, Jun. 13, 2005, http://www.boston.com/yourlife/health/mental/articles/2005/06/13/getting_wired_could_help_predict_emotions/?page=full, 4 pages.
Gomez et al., "Respiratory Responses Associated with Affective Processing of Film Stimuli," Biological Psychology, vol. 68, Issue 3, Mar. 2005, pp. 223-235, 2 pages. (Abstract provided.).
Hall, "Is cognitive processing the right dimension," World Advertising Research Center, Jan. 2003, 3 pages.
Hall, "On Measuring the Power of Communications," Journal of Advertising Research, 44, pp. 1-11, doi:10.1017/S0021849904040139, (2004), 1 page. (Abstract provided.).
Hall, "Research and strategy: a fall from grace," ADMAP, Issue 443, pp. 18-20, 2003, 1 page. (Abstract provided).
Hubert et al., "Autonomic, neuroendocrine, and subjective responses to emotion-inducing film stimuli," Int J Psychophysiol, Aug. 1991, 2 pages. (Abstract provided.).
Levenson et al., "Emotion and Autonomic Nervous System Activity in the Minangkabau of West Sumatra," Department of Psychology, University of California, Berkeley, Journal of Personality and Social Psychology, 1992, 2 pages. (Abstract provided.).
Marci et al., "The effect of emotional distance on psychophysiologic concordance and perceived empathy between patient and interviewer," Applied Psychophysiology and Biofeedback, Jun. 2006, vol. 31, issue 2, 31:115-129, 8 pages. (Abstract provided.).
Mccraty et al., "Analysis of twenty-four hour heart rate variability in patients with panic disorder," Biological Psychology, vol. 56, Issue 2, Jun. 2001, pp. 131-150, 1 page. (Abstract provided.).
Mccraty et al., "Electrophysiological Evidence of Intuition: Part 1. The Surprising Role of the Heart," The Journal of Alternative and Complementary Medicine, vol. 10, No. 1, 2004, pp. 133-143, Mary Ann Liebert, Inc., 12 pages.
Mccraty et al., "Electrophysiological Evidence of Intuition: Part 2. A System-Wide Process?," The Journal of Alternative and Complementary Medicine, vol. 10, No. 2, 2004, pp. 325-336, Mary Ann Liebert, Inc., 12 pages.
Mccraty et al., "The Effects of Different Types of Music on Mood, Tension, and Mental Clarity," Original Research, Alternative Therapies, Jan. 1998, vol. 4., No. 1, pp. 75-84, 10 pages.
Mccraty et al., "The Effects of Emotions on Short-Term Power Spectrum Analysis of Heart Rate Variability," American Journal of Cardiology, vol. 76, No. 14, Nov. 15, 1995, pp. 1089-1093, 6 pages.
Mccraty et al., "The Impact of a New Emotional Self-Management Program on Stress, Emotions, Heart Rate Variability, DHEA and Cortisol," Integrative Physiological and Behavioral Science, Apr.-Jun. 1998, vol. 33, No. 2, 151-170, 20 pages.
Mccraty et al., "The Impact of an Emotional Self-Management Skills Course on Psychosocial Functioning and Autonomic Recovery to Stress in Middle School Children," Integrative Physiological and Behavioral Science, Oct.-Dec. 1999, vol. 34, No. 4, 246-268, 23 pages.

(56) References Cited

OTHER PUBLICATIONS

Melillo, "Inside the Consumer Mind; What Neuroscience Can Tell Us About Marketing," Adweek, Public Citizen's Commercial Alert, Jan. 16, 2006, http://www.adweek.com/news/advertising/inside-consumer-mind-83549, 8 pages.
Miller et al., "Influence of Specific Emotional States on Autonomic Reactivity and Pulmonary Function in Asthmatic Children," Journal of the American Academy of Child & Adolescent Psychiatry, vol. 36, Issue 5, May 1997, pp. 669-677, 3 pages. (Abstract provided).
Murphy et al., "The Heart Reinnervates After Transplantation," Official Journal of the Society of Thoracic Surgeons and the Southern Thoracic Surgical Association, Jun. 2000, vol. 69, Issue 6, pp. 1769-1781, 13 pages.
Rosenberg, "Emotional R.O.I.," The Hub, May/Jun. 2006,pp. 24-25, 2 pages.
Tiller et al., "Cardiac Coherence: A New, Noninvasive Measure of Autonomic Nervous System Order," Alternative Therapies, Jan. 1996, vol. 2, No. 1, 14 pages.
Umetani et al. "Twenty-Four Hour Time Domain Heart Rate Variability and Heart Rate: Relations to Age and Gender Over Nine Decades," J Am Coll Cardiol, Mar. 1, 1998, pp. 593-601, 9 pages.
Von Leupoldt et al., "Emotions in a Body Plethysmograph," Journal of Psychophysiology (2004), 18, pp. 170-176, 1 page. (Abstract provided.).
Kallman, "Effect of Blank Time on Picture Recognition," The American Journal of Psychology, vol. 97, No. 3 (Autumn, 1984), pp. 399-406, 4 pages. (Abstract provided.).
Larose, *Data Mining Methods and Models*, Department of Mathematical Sciences, Central Connecticut State University, www.dbeBooks.com—An Ebook Library,published by John Wiley & Sons, Inc., 2006, 340 pages. (Book).
Han et al., *Data Mining: Concepts and Techniques*, $2^{nd}$ Edition, Elsevier, 2006, 772 pages. (Book).
Liu et al., *Web Data Mining: Exploring Hyperlinks, Contents, and Usage Data*, Springer Science & Business Media, 2007, 532 pages, (Book).
Berry et al., *Data Mining Techniques: For Marketing, Sales, and Customer Support*, Wiley Publishing Inc., Jun. 1997, 464 pages. (Book).
Horovitz, "Watching Ads Is Real Science Research Companies Monitor Physiological Reactions to Commercials to Determine Their Effectiveness," Los Angeles Times, Sep. 1, 1991, 3 pages.
Sung et al., "Wearable feedback systems for rehabilitation," Journal of NeuroEngineering and Rehabilitation, Jun. 29, 2005, 12 pages.
Jaffe, *Casting for Big Ideas*, Adweek Magazine Series, Book 8, 2003, 256 page. (Book).
Hall, "Advertising as a Factor of Production," ADMAP, 2003, pp. 47-49, 1 page. (Abstract provided.).
Ranii, "Adding Science to Gut Check," The News & Observer, D3 (Apr. 6, 2005), 1 page. (Abstract provided.).
Landau et al., "Different Effects of Voluntary and Involuntary Attention on EEG Activity in the Gamma Band," The Journal of Neuroscience, 27(44), Oct. 31, 2007, pp. 11986-11990, 5 pages.
Cohen, "Differentiated product demand analysis with a structured covariance probit: A Bayesian econometric approach," 2009, PhD dissertation, University of Connecticut, pp. 1-184, 197 pages.
Opitz, S. "Neuromarketing: An Introduction" Power Point Presentation (2008), available at http://www.powershow.com/view/94a7b-YzlmN/Neuromarketing_powerpoint_ppt_presentation, (last accessed Oct. 14, 2015), 20 pages.
Jaimes et al., "Multimodal Human-Computer Interaction: A Survey," Computer Vision and Image Understanding 108 (Oct.-Nov. 2007), pp. 116-134, 19 pages.
English Translation of Office Action, issued by the Israeli Patent Office in connection with Patent Application No. 201187, dated Apr. 23, 2014, 2 pages.
Axis Communications, "Improve your merchandising effectiveness. Get the full picture with network video," (2008), available at http://www.axis.com/files/user _scenario slap_ret_merchandising_ 31107 en 0803 lo.pdf, 2 pages.

Brown, M., "Should My Advertising Stimulate an Emotional Response?" (2009), available at http://www.wpp.com/ ~/media/sharedwpp/readingroom/marketing/millward brown_ emotional_ response.pdf, 6 pages.
Cassanello et al., "Neuronal Responses to Moving Targets in Monkey Frontal Eye Fields," Journal of Neurophysiology, (Sep. 2008), 1544-1556, 16 pages.
Advisory action, issued by the United States Patent and Trademark Office in connection with U.S. Appl. No. 12/608,660, dated Oct. 26, 2012, 3 pages.
Decision on Appeal, issued by the United States Patent and Trademark Office in connection with U.S. Appl. No. 13/965,805, on Sep. 10, 2018, 11 pages.
Decision on Appeal, issued by the United States Patent and Trademark Office in connection with U.S. Appl. No. 12/234,372, on Sep. 19, 2018, 8 pages.
Final Office Action, issued by the United States Patent and Trademark Office in connection with U.S. Appl. No. 13/708,525, dated Oct. 5, 2018, 31 pages.
Advisory Action, issued by the United States Patent and Trademark Office in connection with U.S. Appl. No. 12/546,586, dated Oct. 1, 2018, 17 pages.
Non-Final Office Action, issued by the United States Patent and Trademark Office in connection with U.S. Appl. No. 16/037,666, dated Oct. 4, 2018, 37 pages.
Notice of Allowance, issued by the United States Patent and Trademark Office in connection with U.S. Appl. No. 16/037,666, dated Dec. 6, 2018, 96 pages.
Summons to Attend Oral Proceedings Pursuant to Rule 115(1) EPC, issued by the European Patent Office in connection with European Patent Application No. 08744383.4, on Dec. 11, 2018, 6 pages.
Decision on Appeal, issued by the United States Patent and Trademark Office in connection with U.S. Appl. No. 12/410,372, on Dec. 28, 2018, 8 pages.
Decision on Request for Rehearing, issued by the United States Patent and Trademark Office in connection with U.S. Appl. No. 12/410,372, on Mar. 27, 2019, 7 pages.
Decision on Appeal, issued by the United States Patent and Trademark Office in connection with U.S. Appl. No. 12/410,380, on Jul. 8, 2019, 12 pages.
Decision on Appeal, issued by the United States Patent and Trademark Office in connection with U.S. Appl. No. 12/413,297, on Sep. 24, 2019, 15 pages.
Non-Final Office Action, issued by the United States Patent and Trademark Office in connection with U.S. Appl. No. 15/967,939, dated Oct. 4, 2019, 5 pages.
Notice of Allowance, issued by the United States Patent and Trademark Office in connection with U.S. Appl. No. 15/989,987, dated Oct. 17, 2019, 8 pages.
Non-Final Office Action, issued by the United States Patent and Trademark Office in connection with U.S. Appl. No. 16/183,131, dated Nov. 18, 2019, 5 pages.
Notice of Allowance, issued by the United States Patent and Trademark Office in connection with U.S. Appl. No. 15/967,939, dated Jan. 29, 2020, 8 pages.
Non-Final Office Action, issued by the United States Patent and Trademark Office in connection with U.S. Appl. No. 12/546,586, dated Jan. 22, 2020, 12 pages.
English Translation of First Examination Report, issued by the Indian Patent Office in connection with Indian Patent Application No. 4438/KOLNP/2009, dated Sep. 25, 2017, 7 pages.
Intimation of Grant and Recordal of Patent, issued by the Indian Patent Office in connection with Indian Patent Application No. 4438/KOLNP/2009, dated Jul. 3, 2019, 1 page.
Intimation of Grant and Recordal of Patent, issued by the Indian Patent Office in connection with Indian Patent Application No. 4441/KOLNP/2009, dated Sep. 3, 2019, 1 page.
Mccraty et al., "Impact of a Workplace Stress Reduction Program on Blood Pressure and Emotional Health in Hypertensive Employees", the Journal of Alternative and Complementary Medicine, vol. 9, No. 3, 2003, pp. 355-369, Mary Ann Liebert, Inc., 15 pages.

(56) References Cited

OTHER PUBLICATIONS

Hall, Bruce F., "A New Model for Measuring Advertising Effectiveness," Journal of Advertising Research, Mar.-Apr. 2002, 10 pages.
Merriam-Webster Online Dictionary, Definition for "Resonance," available at http://www.merriam-webster.com/dictionary/resonance, 4 pages.
Office Action, issued by the Japanese Patent Office in connection with Patent Application No. 2010-501190, dated Oct. 2, 2012, 10 pages (includes English translation).
Merriam Webster Online Dictionary, Definition of Virtual Reality, available at http://www.merriam-webster.com/dictionary/virtual%20reality, 2 pages.
Lewis et al., "Market Researchers make Increasing use of Brain Imaging," ACNR, vol. 5, No. 3, pp. 36-37, (Jul./Aug. 2005), 2 pages.
Cheng, et al. "Gender Differences in the Mu Rhythm of the Human Mirror-Neuron System," PLos One, vol. 3, Issue 5, www.plosone.org, (May 2008), 7 pages.

\* cited by examiner

NEUROLOGICAL PROFILES FOR MARKET MATCHING AND STIMULUS PRESENTATION

RELATED APPLICATION

This patent arises from a continuation of U.S. patent application Ser. No. 12/410,380, filed on Mar. 24, 2009, entitled "Neurological Profiles for Market Matching and Stimulus Presentation." U.S. patent application Ser. No. 12/410,380 is hereby incorporated by reference in its entity. Priority to U.S. patent application Ser. No. 12/410,380 is hereby claimed.

TECHNICAL FIELD

The present disclosure relates to neurological profiles. More particularly, the present disclosure relates to determining neurological profiles for market matching and stimulus presentation.

DESCRIPTION OF RELATED ART

A variety of conventional systems are available for presenting advertising to a user. In some instances, advertising can be personalized based on demographic information. For example, a web site may identify a user's gender and present product matches directed to that gender. A program having a predominantly wealthier audience may include advertising directed at wealthier individuals. Viewers in a particular local market may be presented with commercials tailored to that local market.

Although a variety of advertising presentation mechanisms are available, the ability to tailor results to a particular user or group are limited. Consequently, it is desirable to provide improved mechanisms for performing market matching and stimulus presentation.

BRIEF DESCRIPTION OF THE DRAWINGS

The disclosure may best be understood by reference to the following description taken in conjunction with the accompanying drawings, which illustrate particular example embodiments.

DESCRIPTION OF PARTICULAR EMBODIMENTS

Figure 1:
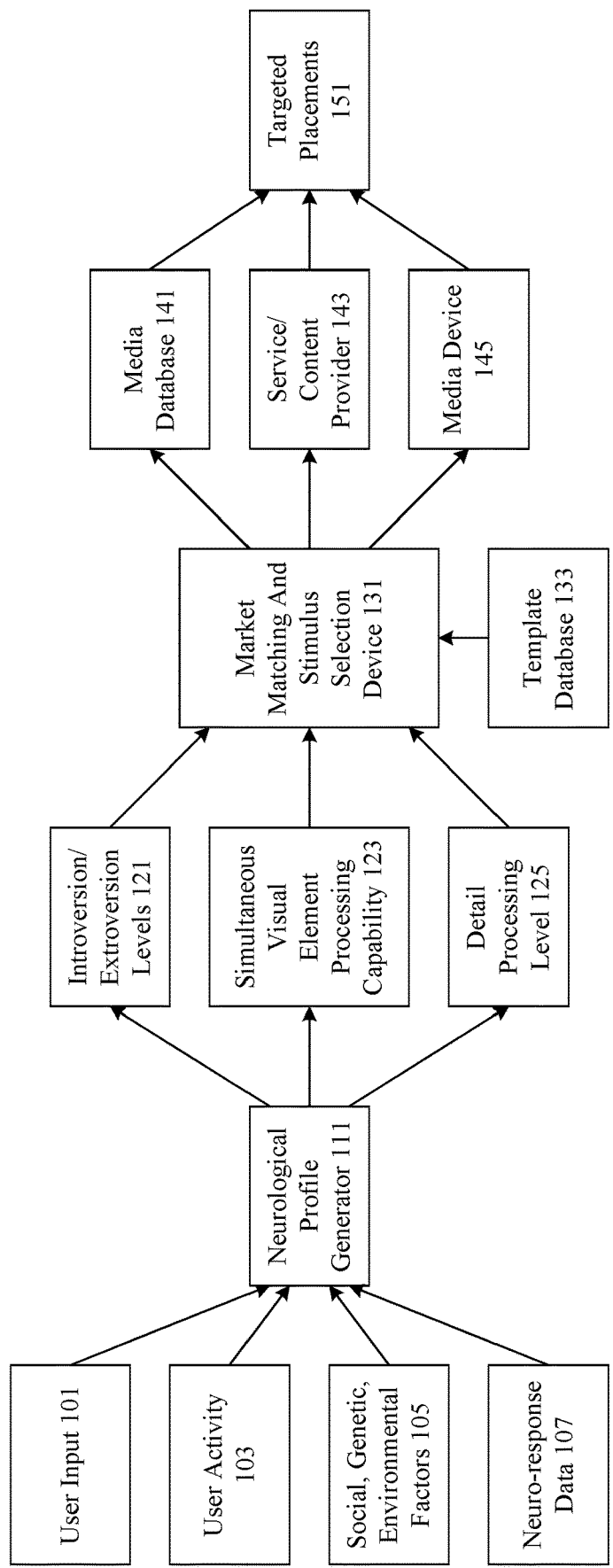
FIG. 1 illustrates one example of a system for performing market matching and stimulus presentation.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

For example, the techniques and mechanisms of the present invention will be described in the context of particular types of media. However, it should be noted that the techniques and mechanisms of the present invention apply to a variety of different types of media. In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors while remaining within the scope of the present invention unless otherwise noted. Furthermore, the techniques and mechanisms of the present invention will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Overview

A neurological profile associated with introversion/extroversion levels, simultaneous visual element processing capability, and/or dynamism processing capability, etc., is determined to select market categories and stimulus material targeted to the particular neurological profile. The neurological profile is determined using information such as user input, user activity, social and environmental factors, genetic and developmental factors, and/or neuro-response data. The neurological profile can be matched with corresponding neurological profile templates to select market categories and stimulus material.

Example Embodiments

A variety of mechanisms for matching particular demographic characteristics associated with a user with particular products, services, and people are available. In one example, a web site recognizes that an individual lives in a particular city and provides services messages associated with that city. In another example, a retailer knows a buyer's purchasing patterns and sends marketing materials tailored to those purchasing patterns. In still another example, a networking site determines a user's interests and makes matches based on those interests.

Providing market matching and stimulus presentation services based on demographic characteristics is effective but limited. Some characteristics associated with a user or buyer may not be easily discernible. In many instances, subjects may not even be aware of their own preferences, capabilities, and behaviors. The techniques and mechanisms of the present invention recognize that cognitive, social, and emotional behavior is influenced by social, environmental, and genetic factors reflected in neurological profiles.

According to various embodiments, neurological profiles associated with users are determined to better perform market matching and stimulus presentation. In particular embodiments, introversion/extroversion levels associated with a user are determined in order to tailor advertising to the user. For example, an extroverted user is presented with an image showing a large group of people while an introverted user is presented with an image showing one or two people. Advertising tailored to particular introversion/extroversion levels may be selected and tailored to the user. The techniques and mechanisms of the present invention recognize that introverted users may be uncomfortable when provided with materials showing large groups. Introversion/extroversion levels may be provided by a user, determined based on user activity, ascertained using social, environmental, and/or genetic factors, or determined using neuro-response data.

According to various embodiments, neurological profiles are generated for users and the neurological profiles are matched with cognitive, social, demographic, and behavioral measures of marketing response. In particular embodiments, extroverted individuals may respond positively to party invitations while introverted individuals may respond positively to book signings. Marketing categories or stimulus materials can be associated with particular neurological profiles or templates.

In another example, the number of visual elements a user can simultaneously process is determined. According to various embodiments, it is recognized that some individuals can simultaneously process three visual elements while others can process five visual elements. In particular embodiments, the three visual elements may be three portions of a webpage. The number of visual elements simultaneously processed can decrease with age. According to various embodiments, the number of simultaneous visual elements can be automatically selected based on demographic information, user selection, social, environmental, and/or genetic factors, and/or neuro-response data.

According to various embodiments, neurological profiles will show increased neuro-response activity up to the maximum number of visual elements a user can process. Advertising, websites, and other stimulus can be tailored to particular individuals based on visual element processing capabilities.

In still other examples, the amount of detail a user is drawn do is determined using neurological profiles. According to various embodiments, it is recognized that particular populations, groups, and subgroups of people are drawn to detail while others generally disregard detail. The amount of detail includes intricacies in the design of a product. According to various embodiments, marketing categories presented to a user can be automatically selected based on demographic information, user selection, social, environmental, and/or genetic factors, and/or neuro-response data.

Although particular neurological profile characteristics are described, it should be noted that a wide variety of characteristics may be evaluated using neurological profiles. According to various embodiments, the amount of dynamism needed in media to elicit a response may be determined using neurological profiles. In particular embodiments, younger individuals growing up in a more media immersed environment may require more constantly dynamism and changing visual elements in order to hold attention. The number of distracters, number of repetitions, or the length of a message may also be varied based on neurological profiles.

The targeted premium placements and advertisement spots can be presented to a user on social networking sites, job placements sites, program commercials, or other media.

FIG. 1 illustrates one example of a system for generating neurological profiles for market matching and stimulus presentation. According to various embodiments, a neurological profile generator 111 receives user information. In particular embodiments, the user information includes user input data 101, user activity 103, social, genetic, and environmental factors 105, and neuro-response data 107. The user input data 101 may be forms or surveys completed by a user. User activity 103 may include user media consumption patterns and purchasing patterns. For example, user activity 103 may indicate that a user prefers highly adorned and detail oriented web content. Social, genetic, and environmental factors 105 may include profiles of friends and family members, cultural and genetic differences, etc.

According to various embodiments, users in a particular country may more likely be introverted than users in other countries. In another example, an individual subscribing to a particular religion may more likely prefer certain types of activities. In particular embodiments, neuro-response data 107 may also be obtained. Neuro-response data 107 may be obtained from the user individually or deduced from other data. Neuro-response data 107 may include user responses collected using Electroencephalography (EEG) or function Magnetic Resonance Imaging (fMRI) when exposed to particular stimulus material such as video showing large groups of people or highly ornate print advertisements.

In particular embodiments, the neurological profile generator 111 receives and user information and generate neurological profiles of users, user subgroups, and user groups. According to various embodiments, the neurological profiles identify introversion/extroversion levels 121, simultaneous visual element processing capability 123, detail processing levels 125, etc. The neurological profile generator 111 may determine that a particular user is introverted, can processing 3 visual elements simultaneously, and does not have an eye for detail. Although on particular types of neurological profile information are described, it should be noted that other neurological profile characteristics can also be determined. For example, levels of optimism/pessimism, thinking/feeling, judging/perceiving, and sensing/intuition can be identified using a neurological profile generator 111. The neurological profile information is passed to a stimulus selection device 131.

According to various embodiments, the stimulus selection device 131 matches neurological profile information to cognitive, social, demographic, and behavioral measures of marketing response. Marketing categories and materials can be matched to particular neurological profiles. In particular embodiments, a template database 133 is accessed to perform matching. The stimulus selection device may indicate that certain types or versions of advertisements are more appropriate for a user with a particular neurological profile.

According to various embodiments, the market matching stimulus selection device 131 provides selection information to entities such as service/content providers 143, media databases 141, and media devices 145. Programming, social network sites, shopping destinations, can place targeted premium placements and advertisement spots 151 as well as provide targeted products and services.

Figure 2:
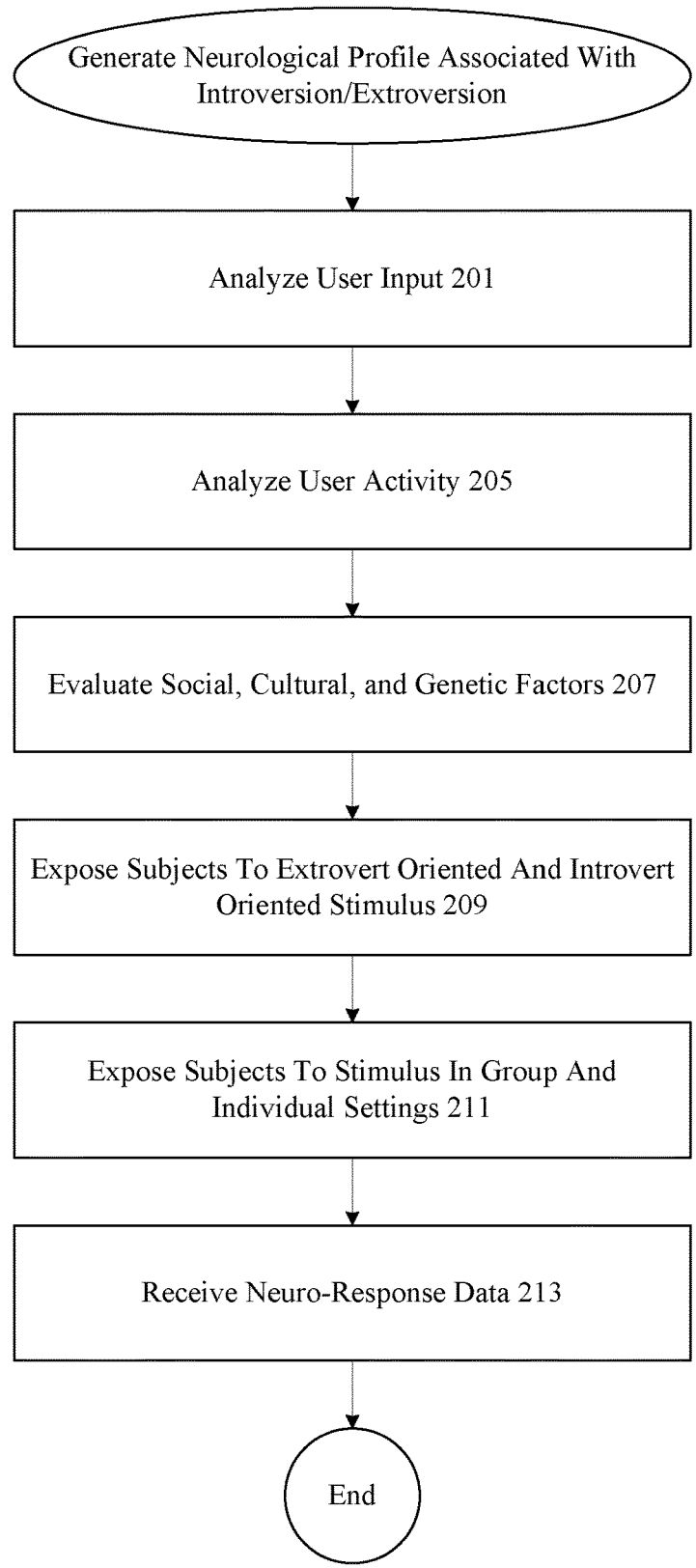
FIG. 2 illustrates one example of a neurological profile associated with determining introversion/extroversion.

FIG. 2 illustrates one example of obtaining a neurological profile associated with introversion/extroversion. According to various embodiments, user input is received at 201. User input may include user submitted forms, surveys, and evaluations. At 205, user activity is analyzed. User activity may include purchasing patterns, activity patterns, etc. Although user input and user activity is described, it should be noted that in various embodiments, user input and user activity may not be used or available. According to various embodiments, social, cultural, and genetic factors are analyzed at 207. Social, cultural, and genetic factors can have significant correlations with user extroversion and introversion levels. In particular embodiments, subjects growing up exposed to a particular culture may tend to be much more introverted than subjects growing up exposed to another culture. It should be noted that other factors such as developmental or neo-natal factors can be evaluated as well.

According to various embodiments, subjects are exposed to extrovert oriented and introvert oriented stimulus at 209. Extrovert oriented stimulus may include video scenes of a large group gathering or social event. Introvert oriented stimulus may include video scenes of reading or relaxing alone. Subjects may also be exposed to stimulus material in group and individual settings at 211 to further gauge introversion/extroversion levels. At 213, neuro-response data is receive and analyzed to determine subject neuro-response activity when exposed to extrovert oriented stimulus and introvert oriented stimulus in group and individual settings. Responses may be compared to responses of known introverts and extroverts and/or analyzed to determine attention, emotional engagement, and memory retention levels in response to the stimulus.

Figure 3:
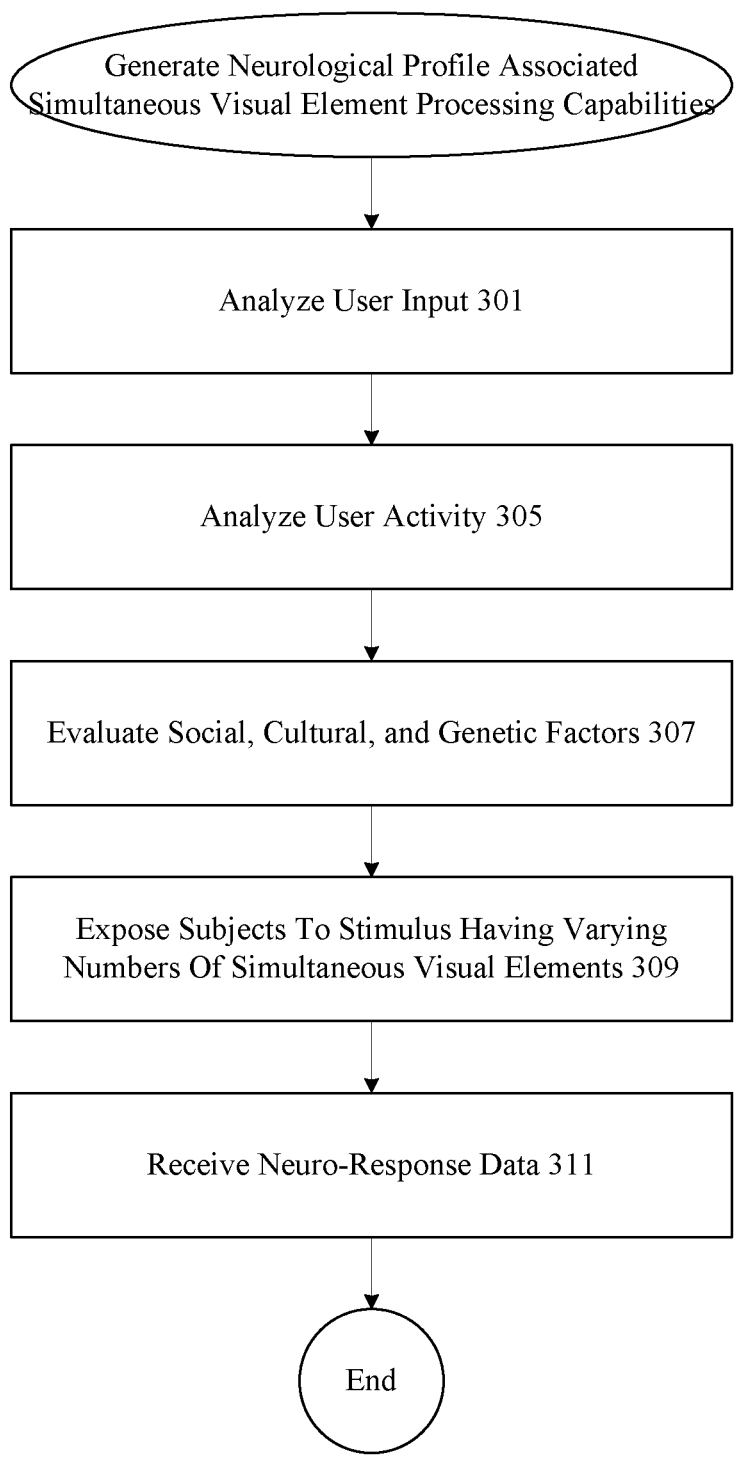
FIG. 3 illustrates one example of a neurological profile associated with determining visual element limitations.

FIG. 3 illustrates one example of determining a neurological profile associated with simultaneous visual element processing capabilities. According to various embodiments, user input is received at 301. User input may include user submitted forms, surveys, and evaluations. At 305, user activity is analyzed. User activity may include purchasing patterns, activity patterns, etc. Although user input and user activity is described, it should be noted that in various embodiments, user input and user activity may not be used or available. According to various embodiments, social, cultural, and genetic factors are analyzed at 307. Social, cultural, and genetic factors can have significant correlations with visual element processing capabilities. In particular embodiments, younger subjects tend to be able to process approximately four or five simultaneous visual elements. The visual elements may be different portions of a web page or different aspects of an image. In particular embodiments, older subjects tend to be able to processing approximately three or four simultaneous visual elements and may be more easily distracted.

According to various embodiments, subjects are exposed to stimulus having varying numbers of simultaneous visual elements at 309. Neuro-response data such as EEG, fMRI, MEG, and Electrooculography (EOG) data is received at 311. Neuro-response data may be measured and analyzed on an individual basis, or on a subgroup and group basis.

Figure 4:
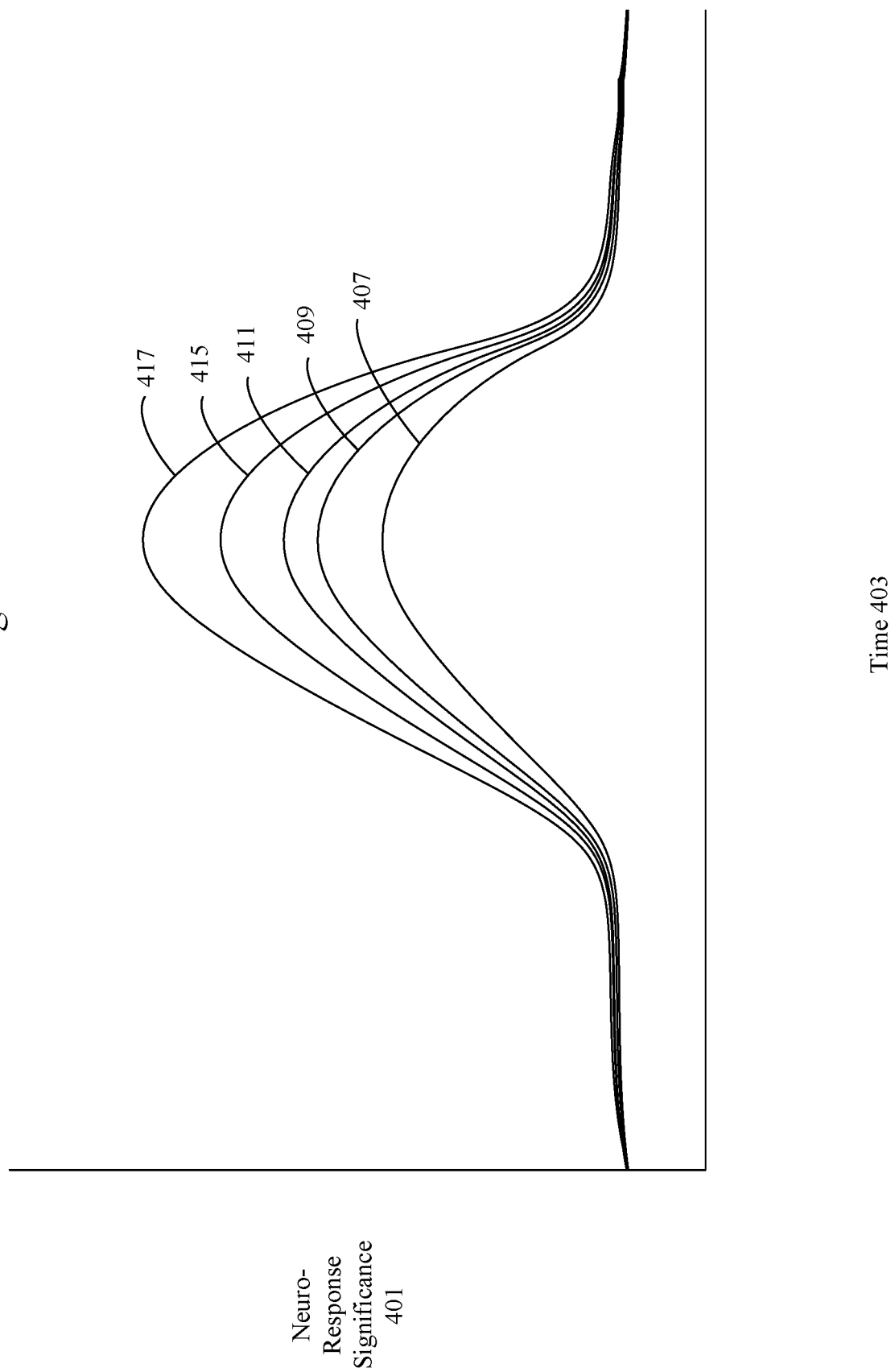
FIG. 4 illustrates one example of neuro-response data associated with evaluating simultaneous visual element processing.

FIG. 4 illustrates one example of response data associated with exposing a subject to simultaneous visual elements. Neuro-response significance 401 is mapped as a function of time 403. According to various embodiments, response 407 corresponds to an EEG response for a subject exposed to one visual element. Response 409 may correspond to an EEG response for a subject exposed to two visual elements. Response 411 may correspond to an EEG response for a subject exposed to three visual elements.

According to various embodiments, a younger subject may exhibit EEG responses corresponding to responses 415 and 417 when exposed to four or five simultaneous visual elements respectively. However, other subjects may exhibit EEG responses corresponding to response 411 when exposed to three, four, or five simultaneous visual elements. No additional neural activity may be measured as elements are added to an image. According to various embodiments, an older subject may show response 411 for a number of simultaneous visual elements greater than or equal to three. In particular embodiments, a younger subject may show response 417 for a number of simultaneous visual elements greater than or equal to five.

Figure 5:
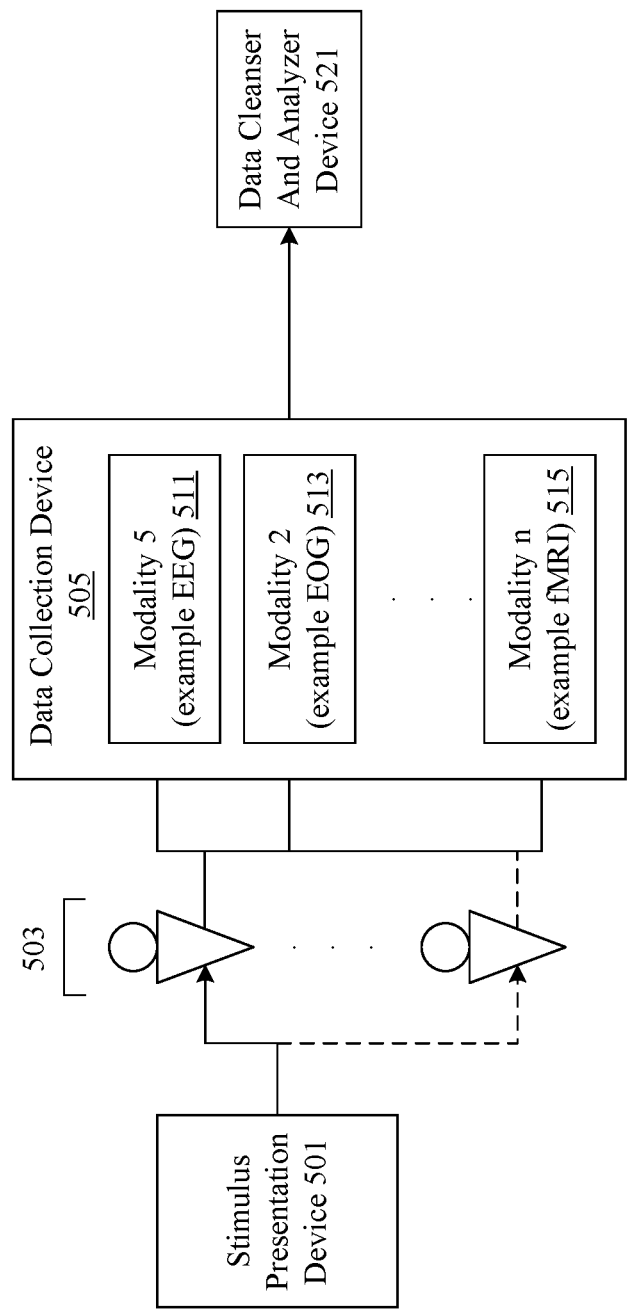
FIG. 5 illustrates one example of a system for analyzing a categorical perception shift boundary and implementing neurologically informed morphing.

FIG. 5 illustrates one example of a system for evaluating neurological profiles. Neuro-response data can be collected and analyzed to determine neurological profile characteristics such as introversion/extroversion, simultaneous visual elements processing capability, attention span, etc. Neuro-response data can also be used to select media appropriate to the neurological profile characteristics of a viewer for presentation to the viewer.

According to various embodiments, a system for evaluating neurological profiles includes a stimulus presentation device 501. In particular embodiments, the stimulus presentation device 501 is merely a display, monitor, screen, speaker, etc., that provides stimulus material to a user. Continuous and discrete modes are supported. According to various embodiments, the stimulus presentation device 501 also has protocol generation capability to allow intelligent customization of stimuli provided to multiple subjects in different markets.

According to various embodiments, stimulus presentation device 501 could include devices such as televisions, cable consoles, computers and monitors, projection systems, display devices, speakers, tactile surfaces, etc., for presenting the video and audio from different networks, local networks, cable channels, syndicated sources, websites, internet content aggregators, portals, service providers, etc.

According to various embodiments, the subjects 503 are connected to data collection devices 505. The data collection devices 505 may include a variety of neuro-response measurement mechanisms including neurological and neurophysiological measurements systems. According to various embodiments, neuro-response data includes central nervous system, autonomic nervous system, and effector data.

Some examples of central nervous system measurement mechanisms include Functional Magnetic Resonance Imaging (fMRI), Magnetoencephalography (MEG), optical imaging, and Electroencephalography (EEG). fMRI measures blood oxygenation in the brain that correlates with increased neural activity. However, current implementations of fMRI have poor temporal resolution of few seconds. MEG measures the magnetic fields produced by electrical activity in the brain via extremely sensitive devices such as superconducting quantum interference devices (SQUIDs). optical imaging measures deflection of light from a laser or infrared source to determine anatomic or chemical properties of a material. EEG measures electrical activity associated with post synaptic currents occurring in the milliseconds range. Subcranial EEG can measure electrical activity with the most accuracy, as the bone and dermal layers weaken transmission of a wide range of frequencies. Nonetheless, surface EEG provides a wealth of electrophysiological information if analyzed properly.

Autonomic nervous system measurement mechanisms include Galvanic Skin Response (GSR), Electrocardiograms (EKG), pupillary dilation, etc. Effector measurement mechanisms include Electrooculography (EOG), eye tracking, facial emotion encoding, reaction time etc.

According to various embodiments, the techniques and mechanisms of the present invention intelligently blend multiple modes and manifestations of precognitive neural signatures with cognitive neural signatures and post cognitive neurophysiological manifestations to more accurately allow assessment of alternate media. In some examples, autonomic nervous system measures are themselves used to validate central nervous system measures. Effector and behavior responses are blended and combined with other measures. According to various embodiments, central nervous system, autonomic nervous system, and effector system measurements are aggregated into a measurement that allows definitive evaluation stimulus material In particular embodiments, the data collection devices 505 include EEG 511, EOG 513, and fMRI 515. In some instances, only a single data collection device is used. Data collection may proceed with or without human supervision.

The data collection device 505 collects neuro-response data from multiple sources. This includes a combination of devices such as central nervous system sources (EEG, MEG, fMRI, optical imaging), autonomic nervous system sources (EKG, pupillary dilation), and effector sources (EOG, eye tracking, facial emotion encoding, reaction time). In particular embodiments, data collected is digitally sampled and stored for later analysis. In particular embodiments, the data collected could be analyzed in real-time. According to particular embodiments, the digital sampling rates are adaptively chosen based on the neurophysiological and neurological data being measured.

In one particular embodiment, the system includes EEG 511 measurements made using scalp level electrodes, EOG 513 measurements made using shielded electrodes to track eye data, functional Magnetic Resonance Imaging (fMRI) 515 measurements made non-invasively to show haemodynamic response related to neural activity, using a differential measurement system, a facial muscular measurement through shielded electrodes placed at specific locations on the face, and a facial affect graphic and video analyzer adaptively derived for each individual.

In particular embodiments, the data collection devices are clock synchronized with a stimulus presentation device 501. In particular embodiments, the data collection devices 505 also include a condition evaluation subsystem that provides auto triggers, alerts and status monitoring and visualization components that continuously monitor the status of the subject, data being collected, and the data collection instruments. The condition evaluation subsystem may also present visual alerts and automatically trigger remedial actions. According to various embodiments, the data collection devices include mechanisms for not only monitoring subject neuro-response to stimulus materials, but also include mechanisms for identifying and monitoring the stimulus materials. For example, data collection devices 505 may be synchronized with a set-top box to monitor channel changes. In other examples, data collection devices 505 may be directionally synchronized to monitor when a subject is no longer paying attention to stimulus material. In still other examples, the data collection devices 505 may receive and store stimulus material generally being viewed by the subject, whether the stimulus is a program, a commercial, printed material, or a scene outside a window. The data collected allows analysis of neuro-response information and correlation of the information to actual stimulus material and not mere subject distractions.

According to various embodiments, the system also includes a data cleanser and analyzer device 521. In particular embodiments, the data cleanser and analyzer device 521 filters the collected data to remove noise, artifacts, and other irrelevant data using fixed and adaptive filtering, weighted averaging, advanced component extraction (like PCA, ICA), vector and component separation methods, etc. This device cleanses the data by removing both exogenous noise (where the source is outside the physiology of the subject, e.g. a phone ringing while a subject is viewing a video) and endogenous artifacts (where the source could be neurophysiological, e.g. muscle movements, eye blinks, etc.).

The artifact removal subsystem includes mechanisms to selectively isolate and review the response data and identify epochs with time domain and/or frequency domain attributes that correspond to artifacts such as line frequency, eye blinks, and muscle movements. The artifact removal subsystem then cleanses the artifacts by either omitting these epochs, or by replacing these epoch data with an estimate based on the other clean data (for example, an EEG nearest neighbor weighted averaging approach).

According to various embodiments, the data cleanser and analyzer device 521 is implemented using hardware, firmware, and/or software.

The data analyzer portion uses a variety of mechanisms to analyze underlying data in the system to determine resonance. According to various embodiments, the data analyzer customizes and extracts the independent neurological and neuro-physiological parameters for each individual in each modality, and blends the estimates within a modality as well as across modalities to elicit an enhanced response to the presented stimulus material. In particular embodiments, the data analyzer aggregates the response measures across subjects in a dataset.

According to various embodiments, neurological and neuro-physiological signatures are measured using time domain analyses and frequency domain analyses. Such analyses use parameters that are common across individuals as well as parameters that are unique to each individual. The analyses could also include statistical parameter extraction and fuzzy logic based attribute estimation from both the time and frequency components of the synthesized response.

In some examples, statistical parameters used in a blended effectiveness estimate include evaluations of skew, peaks, first and second moments, distribution, as well as fuzzy estimates of attention, emotional engagement and memory retention responses.

According to various embodiments, the data analyzer may include an intra-modality response synthesizer and a cross-modality response synthesizer. In particular embodiments, the intra-modality response synthesizer is configured to customize and extract the independent neurological and neurophysiological parameters for each individual in each modality and blend the estimates within a modality analytically to elicit an enhanced response to the presented stimuli. In particular embodiments, the intra-modality response synthesizer also aggregates data from different subjects in a dataset.

According to various embodiments, the cross-modality response synthesizer or fusion device blends different intra-modality responses, including raw signals and signals output. The combination of signals enhances the measures of effectiveness within a modality. The cross-modality response fusion device can also aggregate data from different subjects in a dataset.

According to various embodiments, the data analyzer also includes a composite enhanced effectiveness estimator (CEEE) that combines the enhanced responses and estimates from each modality to provide a blended estimate of the effectiveness. In particular embodiments, blended estimates are provided for each exposure of a subject to stimulus materials. The blended estimates are evaluated over time to assess resonance characteristics. According to various embodiments, numerical values are assigned to each blended estimate. The numerical values may correspond to the intensity of neuro-response measurements, the significance of peaks, the change between peaks, etc. Higher numerical values may correspond to higher significance in neuro-response intensity. Lower numerical values may correspond to lower significance or even insignificant neuro-response activity. In other examples, multiple values are assigned to each blended estimate. In still other examples, blended estimates of neuro-response significance are graphically represented to show changes after repeated exposure.

According to various embodiments, a data analyzer passes data to a resonance estimator that assesses and extracts resonance patterns. In particular embodiments, the resonance estimator determines entity positions in various stimulus segments and matches position information with eye tracking paths while correlating saccades with neural assessments of attention, memory retention, and emotional engagement. In particular embodiments, the resonance estimator stores data in the priming repository system. As with a variety of the components in the system, various repositories can be co-located with the rest of the system and the user, or could be implemented in remote locations.

Figure 6:
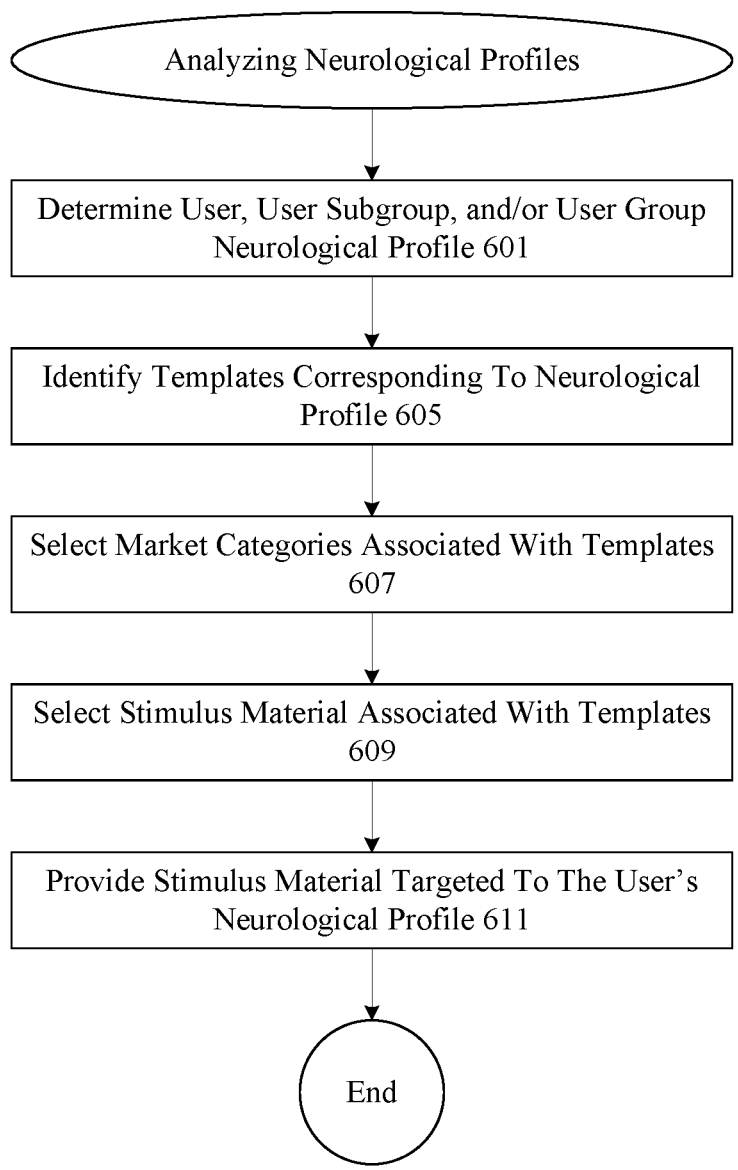
FIG. 6 illustrates one example of a technique for performing market matching and stimulus presentation using a neurological profile.

FIG. 6 illustrates an example of a technique for analyzing neurological profiles. At 601, a neurological profile for a user, user subgroup, and/or a user group is determined. According to various embodiments, the neurological profile may be determined using user input data, user activity, social, genetic, and environmental factors, and neuro-response data. In particular embodiments, the neurological profile may also be derived based on demographic factors associated with the user. According to various embodiments, templates corresponding to the neurological profile are identified at 605. Templates may be identified by finding corresponding EEG and fMRI response data. Templates may be associated with introverts, extroverts, detail oriented individuals, individuals capable of processing numerous simultaneous visual elements, etc.

According to various embodiments, the templates may be generated using neuro-response data. For example, subjects known to be introverts through a variety of measurements may have neuro-response measurements collected and aggregated to create one or more introvert templates.

According to various embodiments, data analysis is performed. Data analysis may include intra-modality response synthesis and cross-modality response synthesis to enhance effectiveness measures. It should be noted that in some particular instances, one type of synthesis may be performed without performing other types of synthesis. For example, cross-modality response synthesis may be performed with or without intra-modality synthesis.

A variety of mechanisms can be used to perform data analysis. In particular embodiments, a stimulus attributes repository is accessed to obtain attributes and characteristics of the stimulus materials, along with purposes, intents, objectives, etc. In particular embodiments, EEG response data is synthesized to provide an enhanced assessment of effectiveness. According to various embodiments, EEG measures electrical activity resulting from thousands of simultaneous neural processes associated with different portions of the brain. EEG data can be classified in various bands. According to various embodiments, brainwave frequencies include delta, theta, alpha, beta, and gamma frequency ranges. Delta waves are classified as those less than 4 Hz and are prominent during deep sleep. Theta waves have frequencies between 3.5 to 7.5 Hz and are associated with memories, attention, emotions, and sensations. Theta waves are typically prominent during states of internal focus.

Alpha frequencies reside between 7.5 and 13 Hz and typically peak around 10 Hz. Alpha waves are prominent during states of relaxation. Beta waves have a frequency range between 14 and 30 Hz. Beta waves are prominent during states of motor control, long range synchronization between brain areas, analytical problem solving, judgment, and decision making. Gamma waves occur between 30 and 60 Hz and are involved in binding of different populations of neurons together into a network for the purpose of carrying out a certain cognitive or motor function, as well as in attention and memory. Because the skull and dermal layers attenuate waves in this frequency range, brain waves above 75-80 Hz are difficult to detect and are often not used for stimuli response assessment.

However, the techniques and mechanisms of the present invention recognize that analyzing high gamma band (kappa-band: Above 60 Hz) measurements, in addition to theta, alpha, beta, and low gamma band measurements, enhances neurological attention, emotional engagement and retention component estimates. In particular embodiments, EEG measurements including difficult to detect high gamma or kappa band measurements are obtained, enhanced, and evaluated. Subject and task specific signature sub-bands in the theta, alpha, beta, gamma and kappa bands are identified to provide enhanced response estimates. According to various embodiments, high gamma waves (kappa-band) above 80 Hz (typically detectable with sub-cranial EEG and/or magnetoencephalograophy) can be used in inverse model-based enhancement of the frequency responses to the stimuli.

Various embodiments of the present invention recognize that particular sub-bands within each frequency range have particular prominence during certain activities. A subset of the frequencies in a particular band is referred to herein as a sub-band. For example, a sub-band may include the 40-45 Hz range within the gamma band. In particular embodiments, multiple sub-bands within the different bands are selected while remaining frequencies are band pass filtered. In particular embodiments, multiple sub-band responses may be enhanced, while the remaining frequency responses may be attenuated.

An information theory based band-weighting model is used for adaptive extraction of selective dataset specific, subject specific, task specific bands to enhance the effectiveness measure. Adaptive extraction may be performed using fuzzy scaling. Stimuli can be presented and enhanced measurements determined multiple times to determine the variation profiles across multiple presentations. Determining various profiles provides an enhanced assessment of the primary responses as well as the longevity (wear-out) of the marketing and entertainment stimuli. The synchronous response of multiple individuals to stimuli presented in concert is measured to determine an enhanced across subject synchrony measure of effectiveness. According to various embodiments, the synchronous response may be determined for multiple subjects residing in separate locations or for multiple subjects residing in the same location.

Although a variety of synthesis mechanisms are described, it should be recognized that any number of mechanisms can be applied—in sequence or in parallel with or without interaction between the mechanisms.

Although intra-modality synthesis mechanisms provide enhanced significance data, additional cross-modality synthesis mechanisms can also be applied. A variety of mechanisms such as EEG, Eye Tracking, fMRI, EOG, and facial emotion encoding are connected to a cross-modality synthesis mechanism. Other mechanisms as well as variations and enhancements on existing mechanisms may also be included. According to various embodiments, data from a specific modality can be enhanced using data from one or more other modalities. In particular embodiments, EEG typically makes frequency measurements in different bands like alpha, beta and gamma to provide estimates of significance. However, the techniques of the present invention recognize that significance measures can be enhanced further using information from other modalities.

For example, facial emotion encoding measures can be used to enhance the valence of the EEG emotional engagement measure. EOG and eye tracking saccadic measures of object entities can be used to enhance the EEG estimates of significance including but not limited to attention, emotional engagement, and memory retention. According to various embodiments, a cross-modality synthesis mechanism performs time and phase shifting of data to allow data from different modalities to align. In some examples, it is recognized that an EEG response will often occur hundreds of milliseconds before a facial emotion measurement changes. Correlations can be drawn and time and phase shifts made on an individual as well as a group basis. In other examples, saccadic eye movements may be determined as occurring before and after particular EEG responses. According to various embodiments, fMRI measures are used to scale and enhance the EEG estimates of significance including attention, emotional engagement and memory retention measures.

Evidence of the occurrence or non-occurrence of specific time domain difference event-related potential components (like the DERP) in specific regions correlates with subject responsiveness to specific stimulus. According to various embodiments, ERP measures are enhanced using EEG time-frequency measures (ERPSP) in response to the presentation of the marketing and entertainment stimuli. Specific portions are extracted and isolated to identify ERP, DERP and ERPSP analyses to perform. In particular embodiments, an EEG frequency estimation of attention, emotion and memory retention (ERPSP) is used as a co-factor in enhancing the ERP, DERP and time-domain response analysis.

EOG measures saccades to determine the presence of attention to specific objects of stimulus. Eye tracking measures the subject's gaze path, location and dwell on specific objects of stimulus. According to various embodiments, EOG and eye tracking is enhanced by measuring the presence of lambda waves (a neurophysiological index of saccade effectiveness) in the ongoing EEG in the occipital and extra striate regions, triggered by the slope of saccade-onset to estimate the significance of the EOG and eye tracking measures. In particular embodiments, specific EEG signatures of activity such as slow potential shifts and measures of coherence in time-frequency responses at the Frontal Eye Field (FEF) regions that preceded saccade-onset are measured to enhance the effectiveness of the saccadic activity data.

According to various embodiments, facial emotion encoding uses templates generated by measuring facial muscle positions and movements of individuals expressing various emotions prior to the testing session. These individual specific facial emotion encoding templates are matched with the individual responses to identify subject emotional response. In particular embodiments, these facial emotion encoding measurements are enhanced by evaluating inter-hemispherical asymmetries in EEG responses in specific frequency bands and measuring frequency band interactions. The techniques of the present invention recognize that not only are particular frequency bands significant in EEG responses, but particular frequency bands used for communication between particular areas of the brain are significant. Consequently, these EEG responses enhance the EMG, graphic and video based facial emotion identification.

According to various embodiments, post-stimulus versus pre-stimulus differential measurements of ERP time domain components in multiple regions of the brain (DERP) are measured. The differential measures give a mechanism for eliciting responses attributable to the stimulus. For example the messaging response attributable to an advertisement or the brand response attributable to multiple brands is determined using pre-resonance and post-resonance estimates Market categories associated with the templates are selected for the user at 607. In particular embodiments, stimulus material associated with templates is selected at 609. For example, advertisements showing large gatherings of people may be selected for individuals having high extroversion levels. Advertisements having a large number of simultaneous visual elements may be selected for individuals having the capability to process a larger number of simultaneous visual elements. At 611, stimulus material targeted to the neurological profile of the user is presented to the user.

According to various embodiments, various mechanisms such as the data collection mechanisms, the intra-modality synthesis mechanisms, cross-modality synthesis mechanisms, etc. are implemented on multiple devices. However, it is also possible that the various mechanisms be implemented in hardware, firmware, and/or software in a single system.

Figure 7:
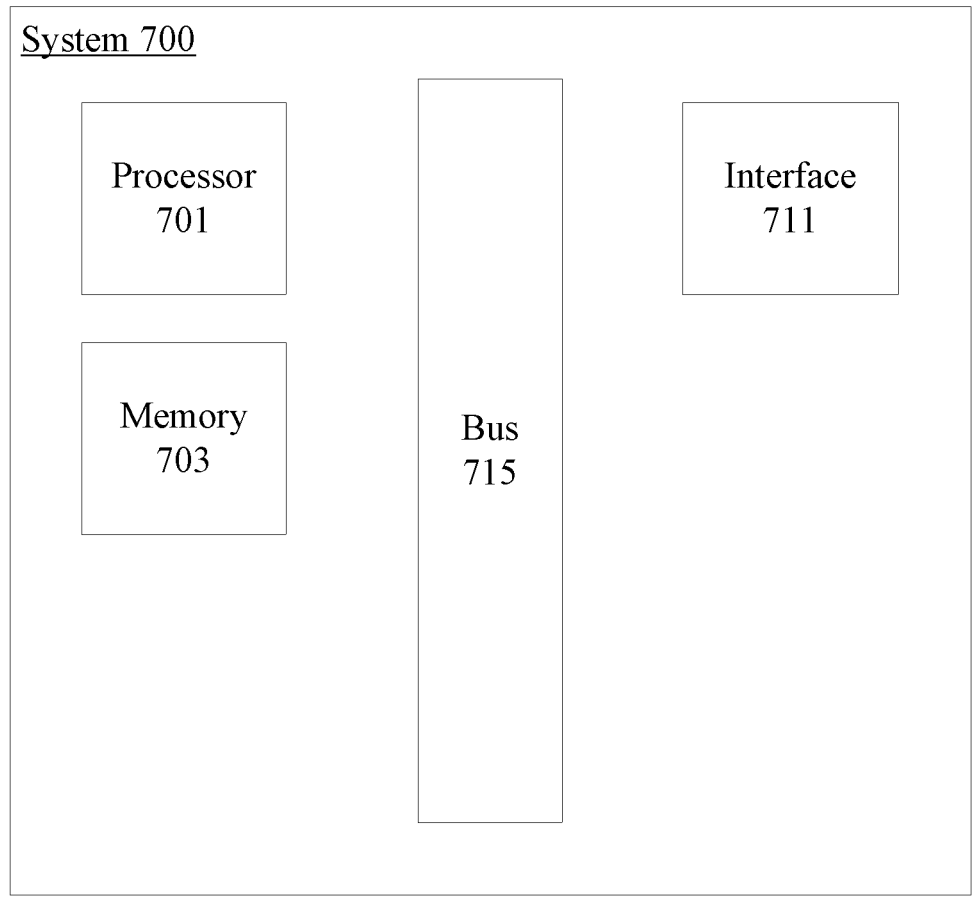
FIG. 7 provides one example of a system that can be used to implement one or more mechanisms.

FIG. 7 provides one example of a system that can be used to implement one or more mechanisms. For example, the system shown in FIG. 7 may be used to implement an alternate media system.

According to particular example embodiments, a system 700 suitable for implementing particular embodiments of the present invention includes a processor 701, a memory 703, an interface 711, and a bus 715 (e.g., a PCI bus). When acting under the control of appropriate software or firmware, the processor 701 is responsible for such tasks such as pattern generation. Various specially configured devices can also be used in place of a processor 701 or in addition to processor 701. The complete implementation can also be done in custom hardware. The interface 711 is typically configured to send and receive data packets or data segments over a network. Particular examples of interfaces the device supports include host bus adapter (HBA) interfaces, Ethernet interfaces, frame relay interfaces, cable interfaces, DSL interfaces, token ring interfaces, and the like.

According to particular example embodiments, the system 700 uses memory 703 to store data, algorithms and program instructions. The program instructions may control the operation of an operating system and/or one or more applications, for example. The memory or memories may also be configured to store received data and process received data.

Because such information and program instructions may be employed to implement the systems/methods described herein, the present invention relates to tangible, machine readable media that include program instructions, state information, etc. for performing various operations described herein. Examples of machine-readable media include, but are not limited to, magnetic media such as hard disks, floppy disks, and magnetic tape; optical media such as CD-ROM disks and DVDs; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Therefore, the present embodiments are to be considered as illustrative and not restrictive and the invention is not to be limited to the details given herein, but may be modified within the scope and equivalents of the appended claims.

What is claimed is:

1. A system for creating media based on a visual processing capability of a user, the system comprising:
 a sensor to obtain first neuro-response data from the user during exposure of the user to first media and to obtain second neuro-response data during exposure of the user to second media, the first media including a first number of simultaneous visual elements and the second media including a second number of simultaneous visual elements, the first number different than the second number;
 memory including instructions; and
 a processor to execute the instructions to:
  determine a maximum number of simultaneously presented visual elements in a stimulus that invokes an increase in a user response in the user based on the first neuro-response data and the second neuro-response data;
  assign a simultaneous visual element processing capability to the user based on the maximum number of simultaneously presented visual elements;
  tailor source media to have the maximum number of simultaneously presented visual elements corresponding to the simultaneous visual element processing capability of the user to generate first tailored media; and
  output the first tailored media for exposure to the user.

2. The system of claim 1, wherein the processor is to:
 determine a first attention level of the user based on the first neuro-response data;
 determine a second attention level of the user based on the second neuro-response data; and
 determine the maximum number of simultaneously presented visual elements based on the first attention level and the second attention level.

3. The system of claim 1, wherein the processor is to:
 identify first neural activity in the first neuro-response data;
 detect an absence of the first neural activity in the second neuro-response data; and
 determine the maximum number of simultaneously presented visual elements based on the absence of the first neural activity in the second neuro-response data.

4. The system of claim 3, wherein the sensor includes an electrode and the first neuro-response data includes electroencephalographic data, the processor to identify the first neural activity based on an interaction of a first frequency band of the electroencephalographic data and a second frequency band of the electroencephalographic data.

5. The system of claim 1, wherein the processor is to generate a neurological profile for the user including the simultaneous visual element processing capability for the user.

6. The system of claim 5, wherein the processor is to:
 determine a detail processing level for the user based on the neurological profile; and
 tailor the source media based on the detail processing level to generate the first tailored media.

7. The system of claim 5, wherein the neurological profile is to further include one or more of demographic data or age data for the user, the processor to tailor the source media based on the one or more of the demographic data or the age data to generate the first tailored media.

8. The system of claim 1, wherein the processor is to:
 access user purchase activity data; and
 tailor the source media based on the user purchase activity data to generate the first tailored, media.

9. The system of claim 1, wherein the user is a first user, the user response is a first user response, the maximum number of simultaneously presented visual elements is a first maximum number of simultaneously presented visual elements, and the simultaneous visual element processing capability is a first simultaneous visual element processing capability, and the processor is to:
 determine a second maximum number of simultaneously presented visual elements in the stimulus that invokes an increase in a second user response in a second user, the second maximum number of simultaneously presented visual elements different than the first maximum number of simultaneously presented visual elements;
 assign a second simultaneous visual element processing capability to the second user based on the second maximum number of simultaneously presented visual elements, the second simultaneous visual element processing capability different than the first simultaneous visual element processing capability; and
 tailor the source media to have the second maximum number of simultaneously presented visual elements corresponding to the second simultaneous visual element processing capability of the second user to generate second tailored media, the second tailored media different than the first tailored media.

10. The system of claim 9, wherein the processor is to:
 determine a detail processing level for the second user; and
 tailor the source media based on the detail processing level for the second user to generate the second tailored media.

11. A tangible machine readable storage disk or storage device comprising instructions that, when executed, cause at least one machine to at least:
 determine a maximum number of simultaneously presented visual elements in a stimulus that invokes an increase in a user response in a user based on first neuro-response data obtained from the user during exposure of the user to first media including a first number of simultaneous visual elements and second neuro-response data obtained from the user during exposure of the user to a second media including a second number of simultaneous visual elements, the first number different from the second number;

assign a simultaneous visual element processing capability to the user based on the maximum number of simultaneously presented visual elements;

tailor source media to have the maximum number of simultaneously presented visual elements corresponding to the simultaneous visual element processing capability of the user to generate first tailored media; and output the first tailored media for exposure to the user.

12. The storage device or storage disk of claim 11, wherein instructions, when executed, cause the at least one machine to:

determine a first attention level of the user based on the first neuro-response data;

determine a second attention level of the user based on the second neuro-response data; and determine the maximum number of simultaneously presented visual elements based on the first attention level and the second attention level.

13. The storage device or storage disk of claim 11, wherein instructions, when executed, cause the at least one machine to:

identify first neural activity in the first neuro-response data;

detect an absence of the first neural activity in the second neuro-response data; and determine the maximum number of simultaneously presented visual elements based on the absence of the first neural activity in the second neuro-response data.

14. The storage device or storage disk of claim 13, wherein the first neuro-response data includes electroencephalographic data and the instructions, when executed, cause the at least one machine to identify the first neural activity based on an interaction of a first frequency band of the electroencephalographic data and a second frequency band of the electroencephalographic data.

15. The storage device or storage disk of claim 11, wherein the instructions, when executed, cause the at least one machine to generate a neurological profile for the user including the simultaneous visual element processing capability for the user.

16. The storage device or storage disk of claim 15, wherein the instructions, when executed, cause the at least one machine:

determine a detail processing level for the user based on the neurological profile; and tailor the source media based on the detail processing level to generate the first tailored media.

17. The storage device or storage disk of claim 15, wherein the neurological profile is to further include one or more of demographic data or age data for the user, and wherein instructions, when executed, cause the at least one machine to tailor the source media based on the one or more of the demographic data or the age data to generate the first tailored media.

18. The storage device or storage disk of claim 11, wherein instructions, when executed, cause the at least one machine to:

access user purchase activity data; and tailor the source media based on the user purchase activity data generate the first tailored media.

19. The storage device or storage disk of claim 11, wherein the user is a first user, the user response is a first user response, the maximum number of simultaneously presented visual elements is a first maximum number of simultaneously presented visual elements, and the simultaneous visual element processing capability is a first simultaneous visual element processing capability, and instructions, when executed, cause the at least one machine to:

determine a second maximum number of simultaneously presented visual elements in the stimulus to invoke an increase in a second user response in a second user, the second maximum number of simultaneously presented visual elements different than the first maximum number of simultaneously presented visual elements;

assign a second simultaneous visual element processing capability to the second user based on the second maximum number of simultaneously presented visual elements, the second simultaneous visual element processing capability different than the first simultaneous visual element processing capability; and tailor the source media to have the second maximum number of simultaneously presented visual elements corresponding to the second simultaneous visual element processing capability of the second user to generate second tailored media, the second tailored media different than the first tailored media.

20. The storage device or storage disk of claim 19, wherein instructions, when executed, cause the at least one machine to:

determine a detail processing level for the second user; and tailor the source media based on the detail processing level for the second user to generate the second tailored media.

* * * * *